(12) United States Patent
Kobashi et al.

(10) Patent No.: US 8,367,843 B2
(45) Date of Patent: Feb. 5, 2013

(54) PHENOL DERIVATIVE

(75) Inventors: Seiichi Kobashi, Saitama (JP); Junichiro Uda, Saitama (JP); Sachiho Miyata, Saitama (JP); Tsutomu Inoue, Saitama (JP); Naoki Ashizawa, Saitama (JP); Koji Matsumoto, Saitama (JP); Tetsuya Taniguchi, Saitama (JP); Takashi Iwanaga, Saitama (JP); Osamu Nagata, Saitama (JP)

(73) Assignee: Fuji Yakuhin Co., Ltd., Saitama (JP)

( * ) Notice: Subject to any disclaimer, the term of this patent is extended or adjusted under 35 U.S.C. 154(b) by 0 days.

(21) Appl. No.: 13/499,190

(22) PCT Filed: Sep. 29, 2010

(86) PCT No.: PCT/JP2010/066925
§ 371 (c)(1),
(2), (4) Date: Mar. 29, 2012

(87) PCT Pub. No.: WO2011/040449
PCT Pub. Date: Apr. 7, 2011

(65) Prior Publication Data
US 2012/0184587 A1 Jul. 19, 2012

(30) Foreign Application Priority Data
Sep. 30, 2009 (JP) ................. 2009-227402

(51) Int. Cl.
*A61K 31/428* (2006.01)
*C07D 277/62* (2006.01)

(52) U.S. Cl. ........................ 548/180; 514/367

(58) Field of Classification Search ............... 548/180
See application file for complete search history.

(56) References Cited

U.S. PATENT DOCUMENTS
3,720,683 A * 3/1973 Brener et al. ................ 548/180

FOREIGN PATENT DOCUMENTS
WO WO 2006/057460 A1 6/2006
WO WO 2007/138998 A1 12/2007

OTHER PUBLICATIONS

Colagiuri et al., American Journal of Public Health, Sep. 2006, vol. 96, No. 9, pp. 1562-1569.*
Bruno et al., Expert Opinion Emerging Drugs, (2005), 10(4), pp. 747-771.*
Park, Diabetes Research and Clinical Practice 66S (2004), S33-S35.*
Curtis et al., The Journal of the American Board of Family Practice, vol. 18, pp. 37-43, (2005).*
Guidelines for the Management of Hyperuricemia and Gout (First Edition), Gout and Nucleic Acid Metabolism, Japanese Society of Gout and Nucleic Acid Metabolism, vol. 26, Supplement 1, 2002, pp. 7-9 and pp. 30-33.
Fang et al., Serum Uric Acid and Cardiovascular Mortality, JAMA, May 10, 2000, vol. 283, No. 18, pp. 2404-2410.
Bos et al., Uric Acid is a Risk Factor for Myocardial Infarction and Stroke: The Rotterdam Study, Stroke, Journal of the American Heart Association, downloaded from http://stroke.ahajournals.org/, Aug. 29, 2012, pp. 1503-1507.
Kanellis et al., Does asymptomatic hyperuricaemia contribute to the development of renal and cardiovascular disease? An old controversy renewed, Nephrology, 2004, 9, pp. 394-399.
Kang et al., Uric Acid and Chronic Renal Disease: Possible Implication of Hyperuricemia on Progression of Renal Disease, WBS, Seminars in Nephrology, 2005, pp. 43-49.
Viazzi et al., Serum Uric Acid as a Risk Factor for Cardiovascular and Renal Disease: An Old Controversy Revived, The Journal of Clinical Hypertension, vol. 8, No. 7, Jul. 2006, pp. 510-518.
Puig et al., Uric acid as a cardiovascular risk factor in arterial hypertension, Journal of Hypertension, 1999, 17, pp. 869-872.
Alderman et al., Uric acid: role in cardiovascular disease and effects of losartan, Current Medical Research and Opinion, vol. 20, No. 3, 2004, pp. 369-379.
Schachter, Uric Acid and Hypertension, Current Pharmaceutical Design, 2005, 11, Bentham Science Publishers Ltd., pp. 4139-4143.
Viazzi et al., Serum Uric Acid and Target Organ Damage in Primary Hypertension, downloaded from hyper.ahajournals.org, Jul. 29, 2009, pp. 991-996.
Hsu et al., Risk Factors for End-Stage Renal Disease, Arch Intern Med., vol. 169, No. 4, Feb. 23, 2009, pp. 342-350.
Tohgi et al., The urate and xanthine concentrations in the cerebrospinal fluid in patients with vascular dementia of the Binswanger type, Alzheimer type dementia, and Parkinson's disease, Journal of Neural Transmission, 6, 1993, pp. 119-126.
Siu et al., Use of Allopurinol in Slowing the Progression of Renal Disease Through its Ability to Lower Serum Uric Acid Level, American Journal of Kidney Diseases, vol. 47, No. 1, Jan. 2006, pp. 51-59.
Hyperuricaemia and Gout, vol. 9, No. 1, 2001, pp. 61-65.
Nakamura et al., Dynamics of uric acid metabolism in hyperuricemia, Internal Medicine I, Fukui Medical School, pp. 3230-3236, 1996.
Nakamura et al., Characteristic features of gouty patients, Department of Medicine, Fukui Medical School, pp. 3248-3255, 1996.
Van Der Klauw et al., Hepatic injury caused by benzbromarone, Journal of Hepatology, 1994, 20, pp. 376-379.
Spaniol et al., Toxicity of amiodarone and amiodarone analogues on isolated rat liver mitochondria, Journal of Hepatology, 35, 2001, pp. 628-636.

(Continued)

*Primary Examiner* — Laura L. Stockton
(74) *Attorney, Agent, or Firm* — Price Heneveld LLP

(57) ABSTRACT

Disclosed are a novel compound and a pharmaceutical product, each having a remarkable uricosuric effect. Specifically disclosed are: a novel phenol derivative represented by general formula (1) that is shown in FIG. 1; a pharmaceutically acceptable salt thereof; a hydrate of the derivative or the salt; and a solvate of the derivative or the salt. (In the formula, $R^1$ and $R^2$ may be the same or different and each represents a lower alkyl group, a lower alkenyl group, a lower alkynyl group, a lower alkoxy group, a haloalkyl group, a haloalkoxy group, an alkylsulfanyl group, an alkylsulfinyl group, an alkylsulfonyl group, a lower alkyl-substituted carbamoyl group, a saturated nitrogen-containing heterocyclic N-carbonyl group, a halogen atom, a cyano group or a hydrogen atom; $R^3$ represents a lower alkyl group, a haloalkyl group, a halogen atom, a hydroxy group or a hydrogen atom; and X represents a sulfur atom, an —S(═O)— group or an —S(═O)$_2$— group.)

13 Claims, 1 Drawing Sheet

OTHER PUBLICATIONS

Kaufmann et al., Mechanisms of Benzarone and Benzbromarone-Induced Hepatic Toxicity, Hepatology, vol. 41, No. 4, 2005, pp. 925-935.
Kunishima et al., Benzbromarone (Urinorm), Fourth Deparment of Internal Medicine, Medical School, The Medical Society of Saitama Medical School, 2003, pp. 187-194.
Locuson II et al., A New Class of CYP2C9 Inhibitors: Probing 2C9 Specificity with High-Affinity Benzbromarone Derivatives, Drug Metabolism and Disposition, vol. 31, No. 7, 2003, pp. 967-971.
Proceedings of the 42nd Annual Meeting of the Japanese Society of Gout and Nucleic Acid Metabolism, 2009, p. 59.
ACR 2008 Annual Scientific Meeting, No. 28, p. 1.

* cited by examiner

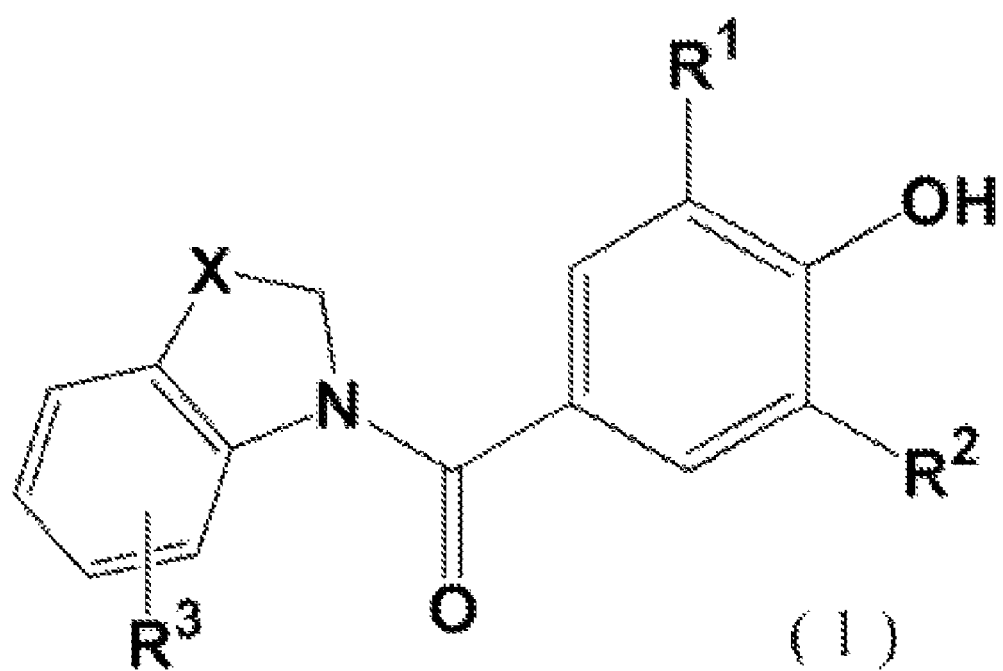
(1)

PHENOL DERIVATIVE

TECHNICAL FIELD

The present invention relates to a novel phenol derivative which exhibits high concentration of an unchanged compound in urine, and also has a remarkable uricosuric action, or a pharmaceutically acceptable salt thereof, or a hydrate thereof or a solvate thereof, and a pharmaceutical containing the same as an active ingredient.

BACKGROUND ART

Uric acid is generated by catabolizing purine, which is formed by decomposition of nucleic acid and adenosine triphosphate (ATP) which is an energy source of the living body, and then by oxidizing the metabolized purine, xanthine, by xanthineoxidase or xanthinedehydrogenase. In case of humans, uric acid (dissociation constant pKa=5.75) is a final metabolite of purine, and is present in the body as a free uric acid or salt.

Uric acid is usually excreted in urine, and hyperuricaemia is caused when uric acid production exceeds its excretion and uric acid in blood is increased. When an excess of uric acid level in blood over upper limit (about 7 mg/dL) of solubility continues for a long period, a crystal of a urate (usually sodium salt) is precipitated.

Urate crystal is deposited on cartilaginous tissues or joints to form a precipitate, and thus leading to gouty node. Whereby, acute gouty arthritis is caused and evolved to chronic gouty arthritis.

When the crystal of the urate is precipitated in urine, renal damage (gouty kidney) such as interstitial nephritis, urinary stone and the like are created. After calming down of stroke of acute gouty arthritis, pharmacotherapy is performed together with the life style improvement support so as to correct hyperuricaemia.

It is important to correct hyperuricaemia and to appropriately manage a uric acid value so as to prevent acute gouty arthritism, gouty kidney, urinary stone and the like.

It is considered that hyperuricaemia is complicated by lifestyle-related diseases such as obesity, hyperlipemia, abnormal glucose tolerance and hypertension at a high rate (see Non-Patent Literature 1 (pp 7-9)). An increase in serum urate concentration exhibits a positive relationship with a death rate due to cardiovascular diseases. Since high serum urate concentration increases death due to cardiovascular diseases, it is suggested that an increase in serum uric acid level is singly and significantly involved in a risk of death due to cardiovascular diseases, (see Non-Patent Literature 2).

It is also suggested that the serum urate concentration is a strong risk factor of myocardial infarction and cerebral haemorrhage (see Non-Patent Literature 3). It has been reported until now that hyperuricaemia is associated with obesity, hyperlipemia, dyslipidemia, abnormal glucose tolerance, diabetes, metabolic syndrome, renal disease (for example, renal insufficiency, urine protein, end stage kidney disease (ESRD), etc.), cardiovascular diseases (for example, hypertension, coronary artery disease, carotid artery disease, endothelial dysfunction, arteriosclerosis, cardiac hypertrophy, cerebrovascular disease, etc.) or a risk factor of these diseases (see Non-Patent Literatures 2 to 11). It has also been reported that the concentration of uric acid in the cerebrospinant increases in vascular dementia (see Non-Patent Literature 12).

Under these circumstances, it is suggested that decrease in blood urate level can delay the proceeding of renal disease, and also can reduce a risk of cardiovascular disease (see Non-Patent Literatures 5, 8, 13 and 14), and it is reported that the treatment should also be applied to asymptomatic hyperuricaemia (see Non-Patent Literature 14).

Accordingly, it is considered that a decrease in blood urate level in the above-mentioned diseases is effective for the treatment or prevention of these diseases, and is also important from the viewpoint of preventing the recurrence of cardiovascular accident and maintaining a renal function.

The main factor of an increase in blood urate level include overproduction and underexcretion of uric acid. It is considered that a method for suppression of the production of uric acid or acceleration of excretion of uric acid is effective as a method for decreasing a blood urate level. It is known that a drug (uric acid production inhibitor) having a mechanism of action of the former includes allopurinol, while a drug (uricosuric drug) having a mechanism of action of the latter includes benzbromarone, probenecid, JP-A-2006-176505 (Patent Literature 1) or the like.

Japanese guidelines for the management of hyperuricemia and gout describes that, in case of a treatment of hyperuricaemia, a uricosuric drug is applied for patients with underexcretion of uric acid and a uric acid production inhibitor is applied against patients with overproduction of uric acid, respectively, as a general Hide (see Non-Patent Literature 1 (pp. 31-32)).

It is said in Japan that patients with underexcretion of uric acid account for about 60% of hyperuricaemia patients and mix type patients with both underexcretion and overproduction of uric acid account for about 25% of hyperuricaemia patients (Non-Patent Literature 15). It is also reported that underexcretion of uric acid is observed in about 85% of gout patients, and even in patients with overproduction of uric acid, an average of uric acid clearance is significantly lower than that of a healthy person, and underexcretion of uric acid as a common phenomenon in all gout patients is suggested (Non-Patent Literature 16).

Accordingly, treatment for patients with underexcretion of uric acid is considered to be important in hyperuricaemia (particularly gout) and significance of the existence of a uricosuric drug is remarkably great.

Among main uricosuric drugs, probenecid is scarcely used since it has a weak action, and gastrointestinal disturbance and an interaction with other drugs are recognized, while serious liver damage is reported in benzbromarone which has a strong uricosuric action and is popularly used as a uricosuric drug in Japan (see Non-Patent Literature 17).

Benzbromarone or an analog thereof exhibits mitochondria toxicity, for example, inhibition of enzyme complex activity of a respiratory chain of mitochondria, uncoupling action, inhibition of respiration, inhibition of fatty acid β oxidation, reduction in mitochondria membrane potential, apoptosis, production of reactive oxygen species and the like, and it is suggested that mitochondria toxicity is involved in the onset of liver damage (see Non-Patent Literatures 18 and 19). An active metabolite of benzbromarone, 6-hydroxy benzbromarone also exhibits toxicity against mitochondria.

Furthermore, benzbromarone has an action of inhibiting cytochrome P450 (CYP) which is a drug metabolizing enzyme and reveals particularly strong inhibition against CYP2C9, and it is suggested to cause a pharmacokinetic drug interaction (see Non-Patent Literatures 20 and 21).

JP-A-2006-176505 (Patent Literature 1) describes a nitrogen-containing fused ring compound, which has an inhibitory action on URAT1 as a kind of urate transporters and also has a structure analogous to that of the compounds of the present invention. However, the compound does not have a sufficient effect and a practicable novel uricosuric drug has not been developed yet.

There has recently been obtained a finding that an uricosuric action depends on the concentration of a drug having the same action in urine, that is, a uricosuric drug exhibits drug effectiveness by being excreted in urine (see Patent Literature 2, Non-Patent Literatures 22 and 23).

Accordingly, more potent, effective uricosuric drug which is excreted in urine in larger quantities is expected. However, the above existing uricosuric drug shows drastically low concentration in urine, and it cannot be said that satisfactory activity is obtained.

With respect to excretion of the drug in urine, the case where the administered drug is excreted as an unchanged compound as it is, and the case where the drug is converted into an active metabolite and then excreted can be estimated. In the latter case, there is a risk that an individual difference in production amount of the active metabolite may increase. In order to obtain stable drug effectiveness and safety, a drug to be excreted as an unchanged compound is more desirable.

[So, it is desired to develop a pharmaceutical which exhibits a high concentration of an unchanged compound in urine, and also has a remarkable uricosuric action and high safety as compared with an existing uricosuric drug.

CITATION LIST

Patent Literature

Patent Literature 1: JP-A-2006-176505
Patent Literature 2: WO 2005/121112

Non-Patent Literatures

Non-Patent Literature 1: Guidelines for the Management of Hyperuricemia and Gout (First Edition) pp. 7-9, and pp. 31-32, Gout and Nucleic Acid Metabolism, Vol. 26, Supplement 1, 2002, Japanese Society of Gout and Nucleic Acid Metabolism
Non-Patent Literature 2: JAMA 283: 2404-2410 (2000)
Non-Patent Literature 3: Stroke 37: 1503-1507 (2006)
Non-Patent Literature 4: Nephrology 9: 394-399 (2004)
Non-Patent Literature 5: Semin. Nephrol. 25: 43-49 (2005)
Non-Patent Literature 6: J. Clin. Hypertens. 8: 510-518 (2006)
Non-Patent Literature 7: J. Hypertens. 17: 869-872 (1999)
Non-Patent Literature 8: Curr. Med. Res. Opin. 20: 369-379 (2004)
Non-Patent Literature 9: Curr. Pharm. Des. 11: 4139-4143 (2005)
Non-Patent Literature 10: Hypertension 45: 991-996 (2005)
Non-Patent Literature 11: Arch. Intern. Med. 169: 342-350 (2009)
Non-Patent Literature 12: J. Neural. Transm. Park Dis. Dement. Sect. 6: 119-126 (1993)
Non-Patent Literature 13: Am. J. Kidney Dis. 47:51-59 (2006)
Non-Patent Literature 14: Hyperuricaemia and Gout 9: 61-65 (2001)
Non-Patent Literature 15: Nippon Rinsho 54: 3230-3236 (1996)
Non-Patent Literature 16: Nippon Rinsho 54: 3248-3255 (1996)
Non-Patent Literature 17: J. Hepatol. 20: 376-379 (1994)
Non-Patent Literature 18: J. HepatoL 35: 628-636 (2001)
Non-Patent Literature 19: Hepatology 41: 925-935 (2005)
Non-Patent Literature 20: Journal of Saitama Medical University (J. Saitama. Med. School) 30: 187-194 (2003)
Non-Patent Literature 21: Drug Metab. Dispos. 31: 967-971 (2003)
Non-Patent Literature 22: Proceedings of the 42nd Annual Meeting of the Japanese Society of Gout and Nucleic Acid Metabolism, p. 59 (2009)
Non-Patent Literature 23: ACR 2008 Annual Scientific Meeting, No. 28

SUMMARY OF INVENTION

Technical Problem

An object of the present invention is to provide novel compounds and pharmaceutical, each having a remarkable uricosuric action.

Solution to Problem

The present inventors have intensively studied so as to achieve the above object and found a novel phenol derivative having high safety and a remarkable uricosuric action, and thus the present invention has been completed.

That is, according to the present invention, there are provided a novel phenol derivative represented by the following general formula (1):

[Chemical Formula 1]

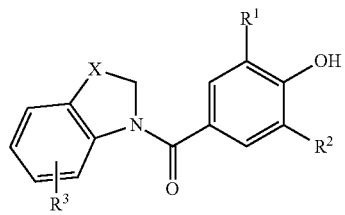

(1)

wherein R1 and R2 are the same or different and represent a lower alkyl group, a lower alkenyl group, a lower alkynyl group, a lower alkoxy group, a haloalkyl group, a haloalkoxy group, an alkylsulfanyl group, an alkylsulfinyl group, an alkylsulfonyl group, a lower alkyl-substituted carbamoyl group, a saturated nitrogen-containing heterocyclic N-carbonyl group, a halogen atom, a cyano group or a hydrogen atom, R3 represents a lower alkyl group, a haloalkyl group, a halogen atom, a hydroxyl group or a hydrogen atom, and X represents a sulfur atom, —S(O)— or —S(O)$_2$—, a pharmaceutically acceptable salt thereof and a hydrate thereof and a solvate thereof and a pharmaceutical composition containing them.

In the present description, the "lower alkyl group" is a C1-6 alkyl group, and may be any of linear, branched and cyclic lower alkyl groups, and an alkyl group consisting of a combination thereof. The same shall apply to alkyl moieties of the substituents having an alkyl moiety [lower alkoxy group, lower alkyl-substituted carbamoyl group, alkylsulfanyl group, etc.]. Examples of the C1-6 alkyl group include a methyl group, an ethyl group, an n-propyl group, an isopropyl group, an n-butyl group, an isobutyl group, an s-butyl group, a t-butyl group, an n-pentyl group, an n-hexyl group, a cyclopropyl group, a cyclobutyl group and the like. Examples of the lower alkoxy group include a methoxy group, an ethoxy group, an n-propoxy group, an isopropoxy group, a cyclopropoxy group, an n-butoxy group, an isobutoxy group, a t-butoxy group, an n-pentoxy group, an n-hexyloxy group and the like. Examples of the lower haloalkoxy group include a trifluoromethoxy group and a trifluoroethoxy group. Examples of the lower haloalkyl group include a trifluoromethyl group, a trifluoroethyl group and the like. Examples of the lower alkylsulfanyl group include a methylsulfanyl group, an ethylsulfanyl group, an isopropylsulfanyl group and the like. Examples of the halogen atom include a fluorine atom, a chlorine atom, a bromine atom and an iodine atom. Examples of the lower alkyl-substituted carbamoyl group include a methylcarbamoyl group, an ethylcarbamoyl group, a dimethylcarbamoyl group, a diethylcarbamoyl group and the like. Examples of the saturated nitrogen-containing heterocyclic N-carbonyl group include a pyrrolidin-1-ylcarbonyl group, a thiazolidin-3-ylcarbonyl group, a 1-oxothiazolidin-3-ylcarbonyl group, a 1,1-dioxothiazolidin-3-ylcarbonyl group and the like. Examples of the lower alkenyl group include a vinyl group, a propenyl group and the like. Examples of the lower alkynyl group include an ethynyl group, a propynyl group and the like. Examples of the lower alkylsulfinyl group include a methylsulfinyl group, an ethylsulfinyl group and the like. Examples of the lower alkylsulfonyl group include a methylsulfonyl group, an ethylsulfonyl group and the like.

The lower alkyl group represented by R1 is preferably an ethyl group, an isopropyl group, an n-butyl group, a t-butyl group, a cyclopropyl group or a cyclobutyl group. The lower haloalkyl group is preferably a trifluoromethyl group. The lower alkoxy group is preferably a methoxy group. The lower haloalkoxy group is preferably a trifluoromethoxy group. The alkylsulfanyl group is preferably a methylsulfanyl group, an ethylsulfanyl group or an isopropylsulfanyl group. The alkylsulfonyl group is preferably a methylsulfonyl group. The halogen atom is preferably a fluorine atom or a chlorine atom. The lower alkyl-substituted carbamoyl group is preferably a dimethylcarbamoyl group. The saturated nitrogen-containing heterocyclic N-carbonyl group is preferably a pyrrolidin-1-ylcarbonyl group, a thiazolidin-3-ylcarbonyl group, a 1-oxothiazolidin-3-ylcarbonyl group or a 1,1-dioxothiazolidin-3-ylcarbonyl group. The lower alkynyl group is preferably an ethynyl group. The lower alkylsulfinyl group is preferably a methylsulfinyl group. R2 is preferably a fluorine atom, a chlorine atom, a cyano group, a methylsulfonyl group or a trifluoromethyl group. X is preferably a sulfur atom or —S(=O)$_2$—. R3 is preferably a hydroxyl group, a trifluoromethyl group or a hydrogen atom.

More preferably, there can be exemplified compounds in which X is —S(=O)$_2$—, R1 is a chlorine atom, a lower alkyl group, a lower alkoxy group, a trifluoromethoxy group, an alkylsulfanyl group or a trifluoromethyl group, R2 is a cyano group, a chlorine, a fluorine atom, a methylsulfonyl group or a trifluoromethyl group, and R3 is a hydrogen atom or a hydroxyl group.

Specifically, the compounds are preferably 3-(3,5-dichloro-4-hydroxybenzoyl)-1,1-dioxo-2,3-dihydro-1,3-benzothiazole, 3-(3-chloro-5-cyano-4-hydroxybenzoyl)-1,1-dioxo-2,3-dihydro-1,3-benzothiazole, 3-(3-cyano-4-hydroxy-5-trifluoromethylbenzoyl)-1,1-dioxo-2,3-dihydro-1,3-benzothiazole, 3-(3-cyano-5-ethyl-4-hydroxybenzoyl)-1,1-dioxo-2,3-dihydro-1,3-benzothiazole, 3-(3-cyano-4-hydroxy-5-methylsulfanylbenzoyl)-1,1-dioxo-2,3-dihydro-1,3-benzothiazole, 3-(3-cyano-5-ethylsulfanyl-4-hydroxybenzoyl)-1,1-dioxo-2,3-dihydro-1,3-benzothiazole, 3-(3-chloro-4-hydroxy-5-methylsulfanylbenzoyl)-1,1-dioxo-2,3-dihydro-1,3-benzothiazole, 3-(3-chloro-4-hydroxy-5-methoxybenzoyl)-1,1-dioxo-2,3-dihydro-1,3-benzothiazole, 3-(3-chloro-5-fluoro-4-hydroxybenzoyl)-1,1-dioxo-2,3-dihydro-1,3-benzothiazole, 3-(3-chloro-4-hydroxy-5-trifluoromethylbenzoyl)-1,1-dioxo-2,3-dihydro-1,3-benzothiazole, 3-(3-chloro-4-hydroxy-5-trifluoromethoxybenzoyl)-1,1-dioxo-2,3-dihydro-1,3-benzothiazole, 3-(5-t-butyl-4-hydroxy-3-methylsulfonylbenzoyl)-1,1-dioxo-2,3-dihydro-1,3-benzothiazole, 3-(3-cyano-5-cyclopropyl-4-hydroxybenzoyl)-1,1-dioxo-2,3-dihydro-1,3-benzothiazole, 3-(3-cyano-5-ethynyl-4-hydroxybenzoyl)-1,1-dioxo-2,3-dihydro-1,3-benzothiazole or a pharmaceutically acceptable salt thereof, or a hydrate thereof or a solvate thereof.

With respect to the compounds of the present invention, isomers may exist. For example, geometric isomers, optical isomers or diastereoisomers may exist. Any of single isomer of these isomers, arbitrary mixtures of isomers, racemates and the like falls within the scope of the present invention.

The compounds of the present invention may form a base addition salt or an acid addition salt depending on a type of the substituent. There is no particular limitation on a type of the salt, and examples thereof include, but are not limited to, metal salts such as sodium salts, potassium salts and calcium salts; base addition salts such as ammonium salts and organic amine salts; mineral acid salts such as hydrochlorides, sulfates and nitrates; organic acid salts such as p-toluenesulfonates, methanesulfonates and tartrates.

The compounds of the present invention and salts thereof may exist as a hydrate or a solvate, and these substances also fall within the scope of the present invention. Examples of the hydrate include ½ hydrates, monohydrates, dihydrates and the like.

A prodrug, as an equivalent compound of a novel phenol derivative represented by the general formula (1) of the present invention, or a pharmaceutically acceptable salt thereof, or a hydrate thereof or a solvate thereof, also falls within the scope of the present invention. The "prodrug" means a compound which is converted into a compound (1) by in vivo metabolism mechanism, that is, a compound which enzymatically causes oxidation, reduction or hydrolysis in vivo, or causes hydrolysis by gastric acid thereby converting into a compound of the general formula (1). Examples of the prodrug of the general formula (1) include compounds in which a phenolic hydroxyl group is modified with an acyl group, an alkyl group and the like, for example, acetylated and pivaloylated compounds.

These compounds can be synthesized from the compound (1) by a known method. The prodrug of the compound (1) may be a prodrug which is converted into the compound (1) under the conditions described in "Soyaku Kagaku", pp. 204-208, published in 2004 by Tokyo Kagaku Dojin Co. Ltd.

There is no particular limitation on the method for the synthesis of the compounds of the present invention and, for example, they can be synthesized in accordance with the following steps. In that case, they can be sometimes produced, effectively from the viewpoint of a synthetic technique, by introducing an appropriate protective group into a functional group in a starting material or an intermediate, depending on the type of the functional group. Examples of such a functional group include an amino group, a hydroxy group, a carboxy group and the like. When the synthesis is performed by introducing a protective group into the functional group, a desired compound can be obtained by appropriately removing the protective group in the respective synthesis stages. Examples of the type of such a protective group and methods for protection and deprotection thereof include those described in, for example, Greene and Wuts, "Protective Groups in Organic Synthesis (Fourth Edition)", and the like.

Advantageous Effects of the Invention

A novel phenol derivative of the present invention, or a pharmaceutically acceptable salt thereof or a hydrate thereof or a solvate thereof exhibits high concentration of an unchanged compound in urine, and also has excellent uricosuric action and are excellent in safety, and is therefore useful as a pharmaceutical for the acceleration of excretion of uric acid; a pharmaceutical for the reduction of the amount of uric acid and/or concentration of uric acid in blood and/or in tissue; a pharmaceutical for use in the prevention and/or treatment of a disease associated with uric acid in blood and/or in tissue; a pharmaceutical for use in the prevention and/or treatment of hyperuricaemia; and a pharmaceutical for use in the prevention and/or treatment of a disease associated with hyperuricaemia and/or a disease accompanied by hyperuricaemia.

BRIEF DESCRIPTION OF DRAWINGS

FIG. 1 is a general formula showing a novel phenol derivative of the present invention.

DESCRIPTION OF EMBODIMENTS

A typical method for the synthesis of novel phenol derivatives represented by the following general formula (1) of the present invention will be described below.
<Production Method>

First step: Acid chloride (3) can be synthesized from a carboxylic acid intermediate (2) as a starting material in an organic solvent, using thionyl chloride, phosphorous pentachloride, phosphorous trichloride, phosphorous oxychloride, oxalyl chloride and the like.

Second step: 2,3-dihydro-1,3-benzothiazole (5) substituted with R3 can be obtained by reacting a 2-aminobenzenethiol (4) substituted with R3 with an aqueous formalin solution, or a formaldehyde equivalent such as paraformaldehyde.

Third step: An amide compound (6) can be synthesized by condensing acid chloride whose phenol is protected, synthesized in the first step, and 2,3-dihydro-1,3-benzothiazole substituted with R3 synthesized in the second step in the presence of a conventional base.

Fourth step: When R1, R2 and R3 of the amide compound (6) are functional groups which are not influenced by oxidation, sulfoxide or sulfone can be obtained by conventional oxidation using an organic acid peroxide such as perchlorobenzoic acid or peracetic acid, hydrogen peroxide and a catalyst. When R1 is a functional group which is influenced by oxidation, for example, an alkylsulfanyl group or the like, a sulfone derivative can be synthesized by simultaneously performing oxidation. In case of synthesizing a derivative in which R1 is an alkylsulfanyl group, the derivative can be obtained from a compound in which R1 is a halogen group such as iodine, using a coupling reaction or the like.

Fifth step: With respect to deprotection of a protected phenolhydroxyl group, for example, the objective product (1) can

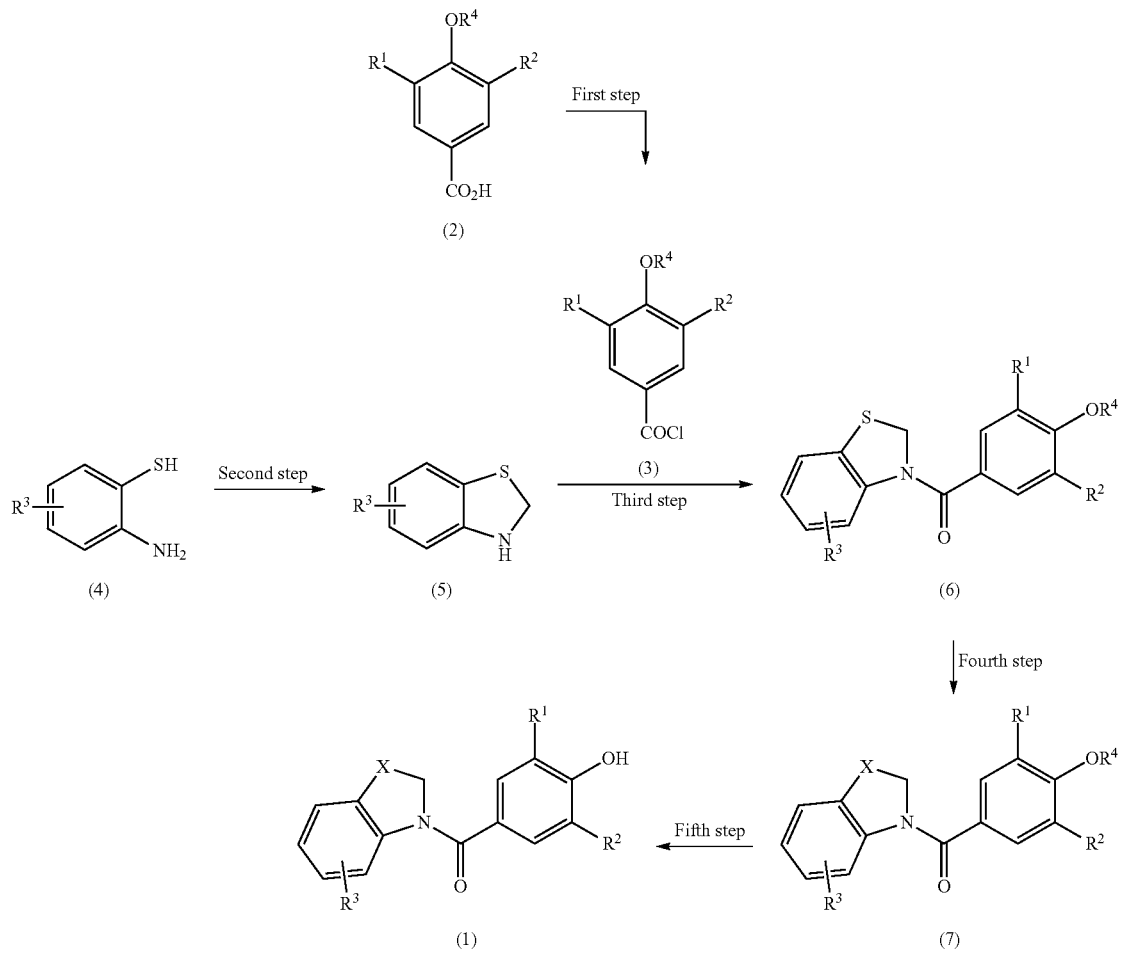

X = S(O)n (n = 0-2)

be synthesized under the deprotection condition described in "Protective Groups in Organic Synthesis (Fourth Edition)" (written by Greene and Wuts). For example, when a protective group is a methyl group, the objective product (1) can be obtained by heating at least equivalent amount of lithium chloride in N,N-dimethylformamide. In case of a benzyl group, the objective product (1) can be obtained by performing catalytic hydrogenation in the presence of a catalyst such as palladium.

The carboxylic acid intermediate (2) to be used in the first step can be synthesized from the respective starting materials by performing the following conventional reaction operation, as shown in the following scheme.

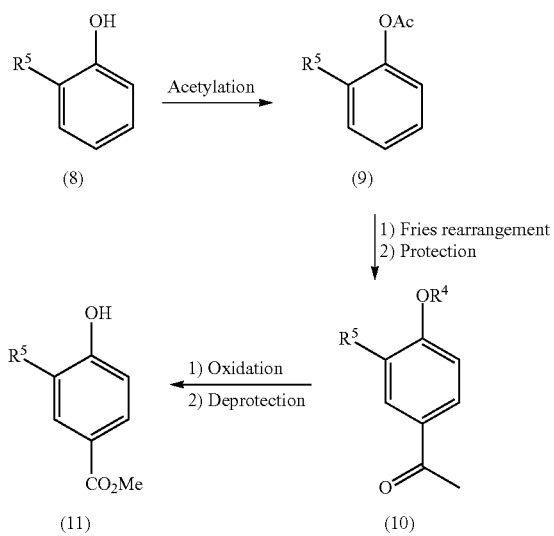

Synthesis method i) Method for the synthesis of a 4-hydroxybenzoic acid ester substituted at the 3-position: For example, with respect to a compound in which R5 is a trifluoromethoxy group, it is possible to synthesize a compound (11) in which R5 is a trifluoromethoxy group, which is a starting material of the synthesis method ii), by acetylating 2-trifluoromethoxyphenol (8) with acetic anhydride or the like, performing Fries rearrangement using trifluoromethanesulfonic acid or the like, and then performing protection of hydroxyl group and esterification by a haloform reaction.

Synthesis method ii) It is possible to synthesize a compound in which R6 is a halogen atom and R5 is a cyano group, a trifluoromethyl group or a trifluoromethoxy group from the 4-hydroxybenzoic acid ester (11) substituted at the 3-position by the following procedure.

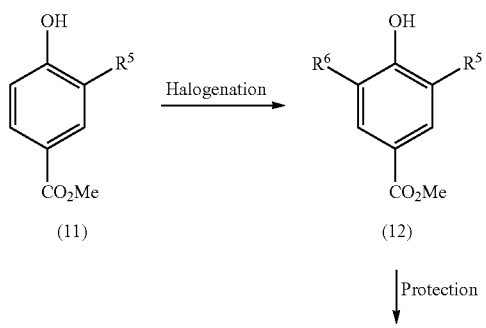

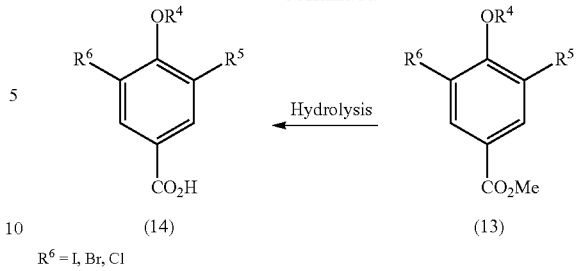

$R^6 = I, Br, Cl$

For example, it is possible to synthesize an ester intermediate (13) in which R6 is a halogen atom and R5 is a cyano group by halogenating the 3-cyano-4-hydroxybenzoic acid ester (11) with a conventional halogenating agent such as N-chlorosuccinimide (NCS), N-bromosuccinimide (NBS) or N-iodosuccinimide (NIS), and then reacting a phenolhydroxyl group with dimethylsulfuric acid, benzylbromide or the like in the presence of a conventional base thereby protecting with R4 (methyl group, benzyl group, etc.). Thus obtained ester intermediate (13) is subjected to a conventional hydrolysis reaction to obtain a carboxylic acid intermediate (14). Under the following hydrolysis condition, for example, the carboxylic acid intermediate can be synthesized by reacting at room temperature or under thermal refluxing in an organic solvent, water, or a mixed solvent with an organic solvent in the presence of the reaction corresponding amount of an acid or a base. Examples of the acid include hydrochloric acid, sulfuric acid, hydrobromic acid, trifluoroacetic acid and the like, and examples of the base include sodium hydroxide, lithium hydroxide and the like.

With respect to an ester intermediate (13-1) in which R6 is an iodine atom, the iodine atom can be converted into a functional group which can be introduced by a general coupling reaction.

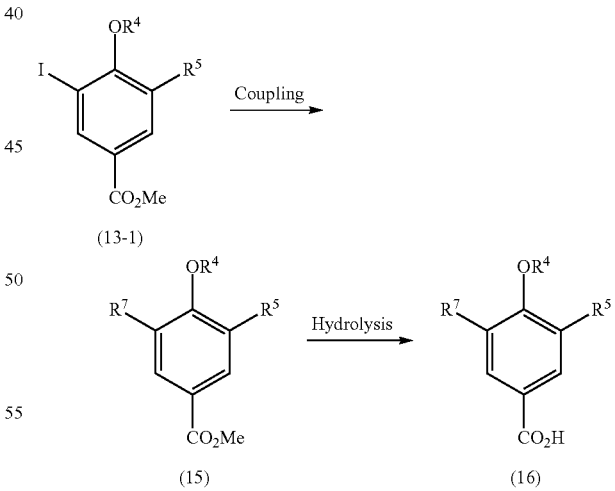

For example, it is possible to synthesize an ester intermediate (15-1) in which R7 is an alkyl group, an alkynyl group or an alkylsulfanyl group from an ester intermediate (13-1-1) in which R5 is a cyano group and R6 is an iodine atom in the presence of a catalyst such as palladium or nickel, using an organoboron compound, alkyne, dialkyl disulfide and the like. It is also possible to convert a derivative of alkyne obtained herein into an alkene derivative, an alkyl derivative and the like by performing a conventional catalytic reduction using a palladium catalyst, hydrogen gas and the like. It is also possible to synthesize an ester intermediate (15-2) in which R5 is a cyano group and R7 is a trifluoromethyl group by reacting the ester intermediate (13-1-1) with methyl fluorosulfonyl difluoroacetate under heating in the presence of copper iodide. It is also possible to perform these coupling reactions in a state (12-1) where a protective group of R4 is absent. An ester intermediate (15) whose phenolhydroxyl group is protected is subjected to a conventional hydrolysis reaction to obtain a carboxylic acid intermediate (16).

Synthesis method iii) When R8 is a functional group which does not exert an influence on the subsequent reaction, for example, an alkyl group, a trifluoromethyl group, an alkoxy group or the like, a carboxylic acid intermediate (23) can be synthesized using, as a starting material, a phenol (17) substituted with R8 at the 2-position.

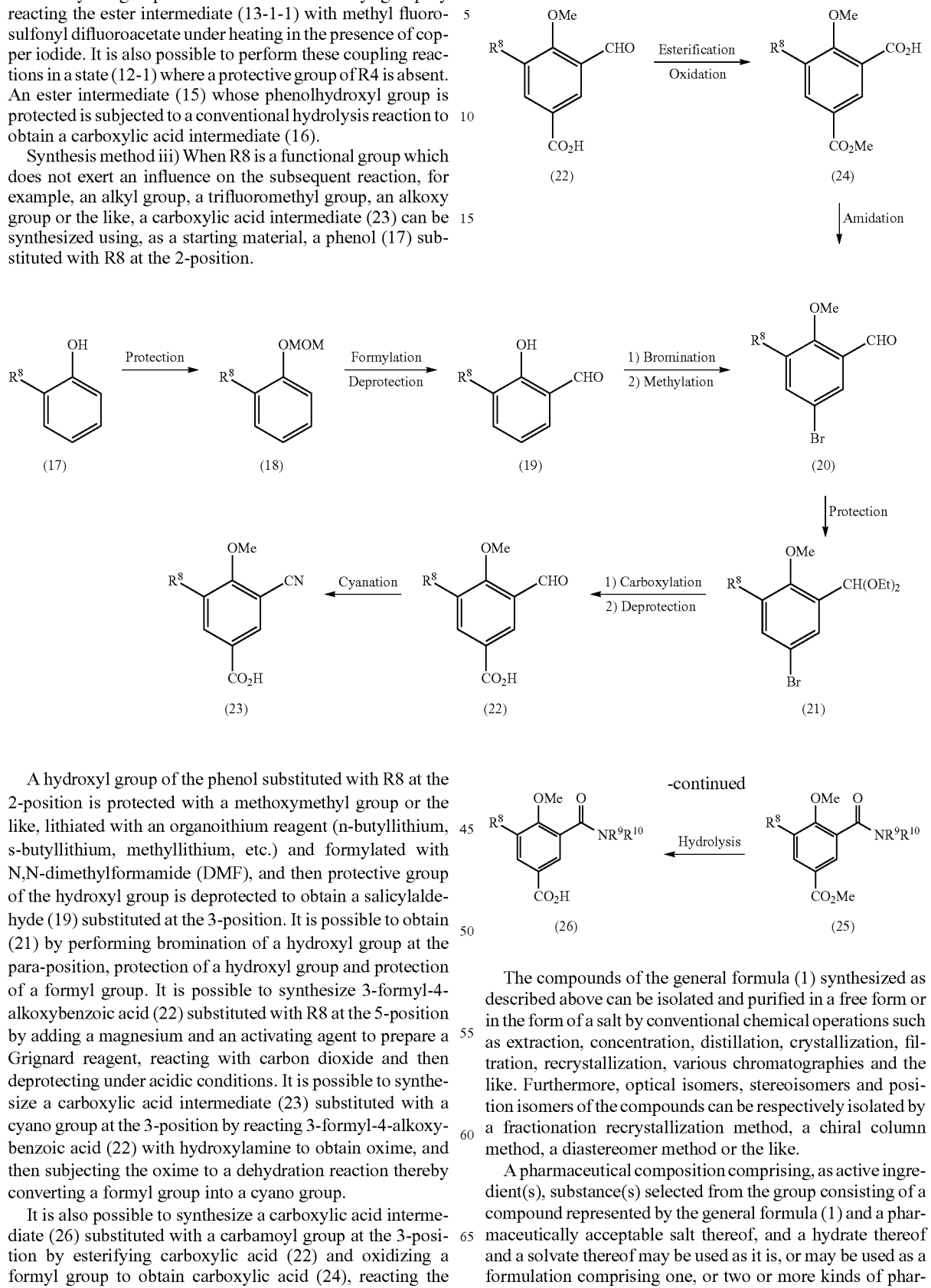

A hydroxyl group of the phenol substituted with R8 at the 2-position is protected with a methoxymethyl group or the like, lithiated with an organolithium reagent (n-butyllithium, s-butyllithium, methyllithium, etc.) and formylated with N,N-dimethylformamide (DMF), and then protective group of the hydroxyl group is deprotected to obtain a salicylaldehyde (19) substituted at the 3-position. It is possible to obtain (21) by performing bromination of a hydroxyl group at the para-position, protection of a hydroxyl group and protection of a formyl group. It is possible to synthesize 3-formyl-4-alkoxybenzoic acid (22) substituted with R8 at the 5-position by adding a magnesium and an activating agent to prepare a Grignard reagent, reacting with carbon dioxide and then deprotecting under acidic conditions. It is possible to synthesize a carboxylic acid intermediate (23) substituted with a cyano group at the 3-position by reacting 3-formyl-4-alkoxy-benzoic acid (22) with hydroxylamine to obtain oxime, and then subjecting the oxime to a dehydration reaction thereby converting a formyl group into a cyano group.

It is also possible to synthesize a carboxylic acid intermediate (26) substituted with a carbamoyl group at the 3-position by esterifying carboxylic acid (22) and oxidizing a formyl group to obtain carboxylic acid (24), reacting the carboxylic acid with amine in the presence of a condensing agent, and then performing an ester hydrolysis.

The compounds of the general formula (1) synthesized as described above can be isolated and purified in a free form or in the form of a salt by conventional chemical operations such as extraction, concentration, distillation, crystallization, filtration, recrystallization, various chromatographies and the like. Furthermore, optical isomers, stereoisomers and position isomers of the compounds can be respectively isolated by a fractionation recrystallization method, a chiral column method, a diastereomer method or the like.

A pharmaceutical composition comprising, as active ingredient(s), substance(s) selected from the group consisting of a compound represented by the general formula (1) and a pharmaceutically acceptable salt thereof, and a hydrate thereof and a solvate thereof may be used as it is, or may be used as a formulation comprising one, or two or more kinds of pharmaceutical additive(s). The pharmaceutical composition may be used in any dosage form and can be used as tablets, pills, capsules, powders, subtilized granules, granules, solutions, suspensions, syrups, injections, external preparations, suppositories and the like.

There is no particular limitation on types of pharmaceutical additives when a pharmaceutical composition comprising, as active ingredients, substance(s) selected from the group consisting of a compound represented by the general formula (1) and a pharmaceutically acceptable salt thereof, and a hydrate thereof and a solvate thereof is used as the above pharmaceutical formulation, and it is possible to use bases, excipients, lubricants, coating agents, sugar coating agents, wetting agents, binders, disintegrating agents, solvents, solubilizers, dissolving agents, dissolving aids, suspending agents, dispersing agents, emulsifiers, surfactants, isotonic agents, buffering agents, pH modifiers, soothing agents, antiseptics, preservatives, stabilizers, antioxidants, colorants, sweeteners and the like alone, or in appropriate combination.

Examples of the bases include kaolin, cacao butter, corn starch, dried aluminum hydroxide gel, crystalline cellulose, methyl cellulose, hydroxypropyl cellulose, macrogol and the like. Examples of the excipients include lactose, sucrose, starch, D-mannitol, corn starch, crystalline cellulose, cellulose derivatives (hydroxypropyl cellulose, carmellose calcium, low substituted hydroxypropyl cellulose, etc.), light anhydrous silicic acid, calcium hydrogen phosphate and the like. Examples of the lubricants include magnesium stearate, calcium stearate, talc, titanium oxide and the like. Examples of the coating agents include carmellose calcium, titanium oxide, aluminum stearate, talc and the like. Examples of the sugar coating agents include sucrose, lactose, gelatin, paraffin, crystalline cellulose and the like. Examples of the wetting agents include glycerol, urine, macrogol and the like. Examples of the binders include crystalline cellulose, sucrose, powdered gum arabic, sodium arginate, carboxymethylethyl cellulose, starch, sucrose, purified gelatin, dextrin, methyl cellulose, carboxymethyl cellulose, sodium carboxymethyl cellulose, carboxymethylethyl cellulose, hydroxyethyl cellulose, hydroxypropyl cellulose, hydroxypropylmethyl cellulose, pullulan, polyvinyl alcohol, polyvinyl pyrrolidone and the like. Examples of the disintegrating agent include sucrose, lactose, starch, agar powder, crospovidone, carboxymethyl cellulose, sodium carboxymethyl starch, carmellose, hydroxypropylmethyl cellulose, citric anhydride, sodium lauryl sulfate, calcium dihydrogen phosphate and the like. Examples of the solvents include purified water, water for injection, ethanol, glycerol, propylene glycol, macrogol, sesame oil, corn oil, hydrochloric acid, acetic acid and the like. Examples of the solubilizers include glycerol, polyoxyl stearate, polysorbate, macrogol and the like. Examples of the dissolving agents include, in addition to those used as the solvents mentioned above, sodium hydroxide, sodium carbonate, meglumine and the like. Examples of the dissolving aids include hydrochloric acid, acetic acid, citric acid, sodium citrate, aspartic acid, sodium hydroxide, ethanol, propylene glycol, D-mannitol, sodium benzoate, benzyl benzoate, urine, triethanolamine, polysorbate, polyvinylpyrrolidone, macrogol and the like. Examples of the suspending agents include gum arabic, benzalkonium chloride, kaolin, carmellose, sodium lauryl sulfate, laurylaminopropionic acid, glyceryl monostearate, polyvinyl alcohol, polyvinyl pyrrolidone, carboxymethyl cellulose sodium, methylcellulose, hydroxymethyl cellulose, hydroxyethyl cellulose, hydroxypropyl cellulose and the like. Examples of the dispersing agents include sodium citrate, light aluminum oxide, titanium oxide, zinc stearate, polysorbate, macrogol, dextrin, low substituted hydroxypropyl cellulose, hydroxypropyl cellulose and the like. Examples of the emulsifiers include benzalkonium chloride, glycerol, propylene glycol, cetanol, lecithin, lanolin, sodium lauryl sulfate and the like. Examples of the surfactant include squalane, cetanol, polyoxyethylene cetyl ether, lauromacrogol and the like. Examples of the isotonic agents include glucose, D-sorbitol, sodium chloride, glycerol, D-mannitol and the like. Examples of the buffering agents include buffer solutions such as phosphate, acetate, carbonate, citrate buffers and the like. Examples of the pH modifiers include inorganic acids such as hydrochloric acid and phosphoric acid, and salts thereof, organic acids such as acetic acid, citric acid, and lactic acid, and salts thereof and the like. Examples of the soothing agents include creatinine, benzyl alcohol and the like. Examples of the antiseptics include p-oxybenzoic acid esters, chlorobutanol, benzyl alcohol, phenethyl alcohol, dehydroacetic acid, sorbic acid and the like. Examples of the preservatives include benzoic acid, p-oxybenzoic acid esters, sorbic acid, and the like. Examples of the stabilizers include taurine, amino acid, p-oxybenzoic acid esters, benzyl alcohol, crystalline cellulose, macrogol and the like. Examples of the antioxidants include sulfite, ascorbic acid and the like. Examples of the colorants include edible dyes, β-carotene, riboflavin and the like. Examples of the sweeteners include aspartame, sucrose, D-sorbitol, maltose and the like. Examples of aromatics include bitter essence, bitter base and the like.

A novel phenol derivative of the present invention exhibits high concentration of an unchanged compound in urine and has a remarkable uricosuric action, and therefore the novel phenol derivative or a pharmaceutically acceptable salt thereof, or a hydrate thereof or a solvate thereof is useful as a pharmaceutical for the control of reabsorption of uric acid and the acceleration of excretion of uric acid; a pharmaceutical for the reduction of the amount of uric acid and/or concentration of uric acid in blood and/or in tissue; a pharmaceutical for use in the prevention and/or treatment of a disease associated with uric acid in blood and/or in tissue; a pharmaceutical for use in the prevention and/or treatment of hyperuricaemia; and a pharmaceutical for use in the prevention and/or treatment of a disease associated with hyperuricaemia and/or a disease accompanied by hyperuricaemia.

There is no particular limitation on the "disease associated with uric acid in blood and/or in tissue" or the "disease associated with hyperuricaemia and/or a disease accompanied by hyperuricaemia" as long as the disease is a disease associated with uric acid regardless of direct or indirect association or a disease suspected to be associated with uric acid and/or a disease complicated by these diseases. Examples thereof include gout, urinary stone, obesity, hyperlipemia, abnormal glucose tolerance, diabetes, metabolic syndrome, renal disease, cerebral haemorrhage and/or cardiovascular disease, and complications of these diseases can also be included.

There is no particular limitation on the subject of gout as long as it has a disease state which meets or conforms to the diagnosis criteria. For example, those having at least one disease state of gouty node, gouty arthritis and gouty kidney are included. Examples of the renal disease include, but are not particularly limited to, renal insufficiency, albuminuria, nephritis, uremia, ESRD and the like. Examples of the cerebrovascular disease include, but are not particularly limited to, cerebrovascular accident, dementia and the like. Examples of the cardiovascular disease include, but are not particularly limited to, hypertension, coronary artery disease, carotid artery disease, arteriosclerosis, cardiac hypertrophy, thrombosis, endothelial dysfunction and/or cardiovascular diseases (stenocardia, myocardial infarction, etc.).

Furthermore, a novel phenol derivative of the present invention can be used in combination with other remedies and/or preventives of the above-mentioned diseases, and is useful for effectively dealing with the diseases. The novel phenol derivative of the present invention is useful in that it can suppress an increase in blood urate level by using in combination with a drug which brings about an increase in blood urate level (for example, antihypertensive diuretic, antituberculosis drug, lipid-lowering drug, antiinflammatory analgesic, asthmaremedy, immunosuppressive drug, antimetabolite, anticancer drug, etc.). It is suggested that the substance capable of decreasing a blood urate level (allopurinol) is effective for neurodegenerative diseases (Alzheimer's disease, Parkinson's disease, Huntington's disease, amyotrophic lateral sclerosis, etc.), pancreatitis and sleep apnea syndrome. Therefore, it is also possible to apply a novel phenol derivative of the present invention or a pharmaceutically acceptable salt thereof, or a hydrate thereof or a solvate thereof for the prevention and/or treatment of neurodegenerative diseases, digestive system diseases such as pancreatitis, and respiratory tract diseases such as sleep apnea syndrome.

Dose and the number of dose of the compounds of the present invention or a pharmaceutical composition containing the compounds can be appropriately selected depending on patient's symptoms, age and sex, dosage form and the type of a drug used in combination and the like. For example, a daily dose for adults can be usually selected from the range of 0.1 to 1,000 mg, preferably 1 to 500 mg, and the aforementioned dose can be administered once a day or several times as divided portions. The pharmaceutical composition of the present invention may be administered alone, or may be administered in combination with other pharmaceuticals having the same and/or different effectiveness.

EXAMPLES

The present invention will be specifically described below by way of Examples, but the present invention is not limited to the following Examples.

The meanings of the abbreviations used in the Examples are as follows:

1H-NMR: proton nuclear magnetic resonance spectrum, CDCl3: deuterium chloroform, DMSO-d6: deuterium dimethyl sulfoxide, CD3OD: deuterium methanol, Hz: hertz, J: coupling constant, m: multiplet, sevent: seventet, quint: quintet, q: quartet, dt: double triplet, dd: double doublet, ddd: double double doublet, t: triplet, d: doublet, s: singlet, brs: broad singlet, M: molar concentration and N: noral. NMR means 270 MHz nuclear magnetic resonance spectrum and tetramethylsilane (TMS) was used as an internal standard substance. MS means mass spectrometry, and an instrument using an electrospray ionization (ESI) method as an ionization method was used.

Example 1

3-(3,5-dichloro-4-hydroxybenzoyl)-1,1-dioxo-2,3-dihydro-1,3-benzothiazole (a) Synthesis of 2,3-dihydro-1,3-benzothiazole 37% formalin (5.2 mL) was diluted with water (80 mL), and diisopropylether (80 mL) and 2-aminobenzenethiol (7.84 g) were added, and then the mixture was stirred at mom temperature for 30 minutes. The organic layer was separated and the aqueous layer was extracted with diisopropylether. The organic layers were combined, washed with saturated brine and then dried over anhydrous sodium sulfate. The solvent was distilled off under reduced pressure and the obtained residue was used for the synthesis of (c).

(b) Synthesis of 3,5-dichloro-4-methoxybenzoyl chloride

To 3,5-dichloro-4-methoxybenzoic acid (8.81 g), toluene (170 mL), N,N-dimethylformamide (5 droplets) and thionyl chloride (6.0 mL) were added, and then the mixture was stirred at 60° C. for 16 hours. The solvent was distilled off under reduced pressure and the obtained residue was azeotroped with toluene and then used for the synthesis of (c).

(c) Synthesis of 3-(3,5-dichloro-4-methoxybenzoyl)-2,3-dihydro-1,3-benzothiazole 2,3-dihydro-1,3-benzothiazole was dissolved in chloroform (50 mL), and triethylamine (17.4 mL) and 3,5-dichloro-4-methoxybenzoyl chloride were added to the solution, and then the mixture was stirred at room temperature for 1 hour. The solvent was distilled off under reduced pressure and water was added, and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was used for the synthesis of (d).

(d) Synthesis of 3-(3,5-dichloro-4-methoxybenzoyl)-1,1-dioxo-2,3-dihydro-1,3-benzothiazole 3-(3,5-dichloro-4-methoxybenzoyl)-2,3-dihydro-1,3-benzothiazole was dissolved in chloroform (230 mL), and 70% metachloroperbenzoic acid (43.25 g) was added to the solution at 0° C., and then the mixture was stirred at room temperature for 20 hours and quenched with 10% sodium thiosulfate. The solvent was distilled off under reduced pressure and 1N sodium hydroxide was added, and then the mixture was extracted with ethyl acetate. The organic layer was washed with 1N sodium hydroxide and saturated brine, and then dried over anhydrous sodium sulfate. The solvent was distilled off under reduced pressure to obtain the title compound (13.25 g) as a colorless crystal.

(e) Synthesis of 3-(3,5-dichloro-4-hydroxybenzoyl)-1,1-dioxo-2,3-dihydro-1,3-benzothiazole 3-(3,5-dichloro-4-methoxybenzoyl)-1,1-dioxo-2,3-dihydro-1,3-benzothiazole (1.00 g) was dissolved in N,N-dimethylformamide (5 mL), and lithium chloride (570 mg) was added, and then the mixture was stirred at 130° C. for 2 hours. To the reaction solution, 1N hydrochloric acid was added, and then the reaction mixture was extracted with ethyl acetate. The organic layer was washed with 1N hydrochloric acid and saturated brine, and then dried over anhydrous sodium sulfate. The solvent was distilled off under reduced pressure and the obtained residue was crystallized from ethanol to obtain the title compound (749 mg) as a colorless crystal.

1H-NMRδ (DMSO-d6): 5.35 (2H, s), 7.44 (1H, dd, J=7.6, 7.6 Hz), 7.74 (2H, s), 7.76 (1H, dd, J=8.4, 7.6 Hz), 7.90 (1H,

Example 2

3-(3,5-dichloro-4-hydroxybenzoyl)-2,3-dihydro-1,3-benzothiazole 3-(3,5-dichloro-4-methoxybenzoyl)-2,3-dihydro-1,3-benzothiazole (300 mg) was dissolved in N,N-dimethylformamide (6 mL), and lithium chloride (374 mg) was added to the solution, and then the mixture was stirred at 120° C. for 16 hours. To the reaction solution, 1N hydrochloric acid was added, and then the reaction mixture was extracted with ethyl acetate. The organic layer was washed with 1N hydrochloric acid and saturated brine, and then dried over anhydrous sodium sulfate. The solvent was distilled off under reduced pressure and the obtained residue was crystallized from n-hexane-ethyl acetate to obtain the title compound (214 mg) as a brown crystal.

1H-NMRδ (DMSO-d6): 5.36 (2H, s), 7.03-7.13 (2H, m), 7.31-7.37 (1H, m), 7.50 (1H, brs), 7.65 (2H, s), 10.89 (1H, brs). MS (m/z): 324 (M-H)-, 326 (M+2-H)-.

Example 3

3-(3,5-dichloro-4-hydroxybenzoyl)-1-oxo-2,3-dihydro-1,3-benzothiazole (a) Synthesis of 3-(3,5-dichloro-4-methoxybenzoyl)-1-oxo-2,3-dihydro-1,3-benzothiazole 3-(3,5-dichloro-4-methoxybenzoyl)-2,3-dihydro-1,3-benzothiazole (500 mg) was dissolved in chloroform (10 mL), and 70% metachloroperbenzoic acid (320 mg) was added to the solution, and the mixture was stirred at 0° C. for 10 minutes. The solvent was distilled off under reduced pressure and water was added, and then the mixture was extracted with ethyl acetate. The organic layer was washed with 1N sodium hydroxide and saturated brine, and then dried over anhydrous sodium sulfate. The solvent was distilled off under reduced pressure and the obtained residue was purified by silica gel column chromatography (n-hexane:ethyl acetate=1:1) to obtain the title compound (336 mg) as a colorless crystal.

(b) Synthesis of 3-(3,5-dichloro-4-hydroxybenzoyl)-1-oxo-2,3-dihydro-1,3-benzothiazole 3-(3,5-dichloro-4-methoxybenzoyl)-1-oxo-2,3-dihydro-1,3-benzothiazole (336 mg) was dissolved in N,N-dimethylformamide (6 mL) and lithium chloride (400 mg) was added to the solution, and then the mixture was stirred at 120° C. for 16 hours. To the reaction solution, 1N hydrochloric acid was added, and then the reaction mixture was extracted with ethyl acetate. The organic layer was washed with 1N hydrochloric acid and saturated brine, and then dried over anhydrous sodium sulfate. The solvent was distilled off under reduced pressure and the obtained residue was crystallized from ethyl acetate-methanol to obtain the title compound (220 mg) as a brown crystal.

1H-NMRδ (DMSO-d6): 5.07 (2H, s), 7.38 (1H, dd, J=7.6, 7.6 Hz), 7.70 (1H, ddd, J=8.3, 7.6, 0.8 Hz), 7.73 (2H, s), 8.00 (1H, d, J=8.3 Hz), 8.07 (1H, d, J=7.6 Hz), 11.06 (1H, brs). MS (m/z): 340 (M-H)-, 342 (M+2-H)-.

d, J=7.6 Hz), 8.04 (1H, d, J=8.4 Hz), 11.04 (1H, brs). MS (m/z): 356 (M-H)-, 358 (M+2-H)-.

Example 4

3-(3-cyano-4-hydroxy-5-trifluoromethylbenzoyl)-1,1-dioxo-2,3-dihydro-1,3-benzothiazole (a) Synthesis of 1-methoxymethoxy-2-trifluoromethylbenzene 2-trifluoromethylphenol (50.00 g) was dissolved in N,N-dimethylformamide (100 mL), and potassium carbonate (85.14 g) and chloromethyl methyl ether (34.7 mL) were added to the solution, and then the mixture was stirred under water cooling for 1 hour. Water was added to the reaction solution, and then the mixture was extracted with n-hexane. The organic layer was washed with water and saturated brine, and then dried over anhydrous sodium sulfate. The solvent was distilled off under reduced pressure to obtain the title compound (64.13 g) as a colorless oily substance.

(b) Synthesis of 2-hydroxy-3-trifluoromethylbenzaldehyde 1-methoxymethoxy-2-trifluoromethylbenzene (64.13 g) was dissolved in tetrahydrofuran (500 mL), and a 2.77M n-butyllithium-n-hexane solution (123 mL) was added to the solution over 45 minutes under an argon gas flow at −70° C., and then the mixture was stirred for 1 hour. N,N-dimethylformamide (28.5 mL) was added, followed by stirring at room temperature for 30 minutes. 4N hydrochloric acid (310 mL) was added, followed by stirring at 60° C. for 19 hours. The organic solvent was distilled off under reduced pressure, and the mixture was extracted with ethyl acetate. The organic layer was washed with saturated brine, and then dried over anhydrous sodium sulfate. The solvent was distilled off under reduced pressure to obtain the title compound (59.16 g) as a yellow crystal.

(c) Synthesis of 5-bromo-2-hydroxy-3-trifluoromethylbenzaldehyde 2-hydroxy-3-trifluoromethylbenzaldehyde (59.16 g) was dissolved in acetonitrile (500 mL), and N-bromosuccinimide (57.56 g) was added to the solution, and then the mixture was stirred at 0° C. for 1 hour. The solvent was distilled off under reduced pressure and water was added, and then the mixture was extracted with ethyl acetate. The organic layer was washed with saturated brine, and then dried over anhydrous sodium sulfate. The solvent was distilled off under reduced pressure and the obtained crystal was washed with n-hexane (50 mL) to obtain the title compound (63.98 g) as a pale yellow crystal.

(d) Synthesis of 5-bromo-2-methoxy-3-trifluoromethylbenzaldehyde 5-bromo-2-hydroxy-3-trifluoromethylbenzaldehyde (63.98 g) was dissolved in N,N-dimethylformamide (130 mL), and potassium carbonate (65.79 g) and dimethylsulfuric acid (31.6 mL) were added to the solution under water cooling, and then the mixture was stirred at room temperature for 3 hours. Water was added to the reaction solution, and then the mixture was extracted with ethyl acetate. The organic layer was washed with 1N hydrochloric acid and saturated brine, and then dried over anhydrous sodium sulfate. The solvent was distilled off under reduced pressure to obtain the title compound (66.19 g) as a brown crystal.

(e) Synthesis of 5-bromo-1-diethoxymethyl-2-methoxy-3-trifluoromethylbenzene 5-bromo-2-methoxy-3-trifluoromethylbenzaldehyde (66.19 g) was dissolved in n-hexane (130 mL) and triethyl orthoformate (51 mL), and Amberlyst-15 (6.62 g) was added to the solution, and then the mixture was refluxed for 3 hours. The reaction solution was filtered, and then the solvent was distilled off under reduced pressure to obtain the title compound (82.81 g) as a brown oily substance.

(f) Synthesis of 3-formyl-4-methoxy-5-trifluoromethylbenzoic acid

To magnesium (5.97 g), tetrahydrofuran (230 mL) and 5-bromo-1-diethoxymethyl-2-methoxy-3-trifluoromethylbenzene (31.55 g) were added, and then the mixture was stirred at room temperature for 90 minutes. The reaction solution was cooled to 0° C. and stirred for 1 hour under a carbon dioxide atmosphere, and then 2N hydrochloric acid (240 mL) was added and the mixture was stirred at room temperature for 16 hours. The organic solvent was distilled off under reduced pressure, and then the mixture was extracted with diisopropylether. The organic layer was extracted with 1N sodium hydroxide (100 mL) added thereto, and then the aqueous layer was washed twice with diisopropylether. The reaction mixture was acidified with 4N hydrochloric acid added thereto, and then extracted with ethyl acetate. The organic layer was washed with saturated brine, and then dried over anhydrous sodium sulfate. The solvent was distilled off under reduced pressure to obtain the title compound (50.05 g) as a brown solid.

(g) Synthesis of 3-cyano-4-methoxy-5-trifluoromethylbenzoic acid 3-formyl-4-methoxy-5-trifluoromethylbenzoic acid (58.04 g) was dissolved in formic acid (290 mL), and hydroxylamine hydrochloride (17.07 g) was added to the solution, and the mixture was refluxed for 19 hours. The solvent was distilled off under reduced pressure and water was added, and then the mixture was extracted with ethyl acetate. The organic layer was washed with saturated brine, and then dried over anhydrous sodium sulfate. The solvent was distilled off under reduced pressure to obtain the title compound (15.62 g) as a brown solid.
1H-NMRδ (DMSO-d6): 4.23 (3H, s), 8.33 (1H, d, J=2.1 Hz), 8.55 (1H, d, J=2.1 Hz). MS (m/z): 244 (M-H)-.

(h) Synthesis of 3-cyano-4-methoxy-5-trifluoromethylbenzoylchloride

To 3-cyano-4-methoxy-5-trifluoromethylbenzoic acid (8.10 g), toluene (160 mL), N,N-dimethylformamide (5 droplets) and thionyl chloride (4.80 mL) were added, and the mixture was stirred at 60° C. for 16 hours. The solvent was distilled off under reduced pressure and the obtained residue was azeotroped with toluene and then used for the synthesis of (i).

(i) Synthesis of 3-(3-cyano-4-methoxy-5-trifluoromethylbenzoyl)-2,3-dihydro-1,3-benzothiazole 2,3-dihydro-1,3-benzothiazole synthesized from 2-aminobenzenethiol (5.00 g) and 37% formalin (3.0 mL) in the same manner as in the synthesis of Example 1 was dissolved in chloroform (50 mL), and triethylamine (11.1 mL) and 3-cyano-4-methoxy-5-trifluoromethylbenzoylchloride were added to the solution, and then the mixture was stirred at room temperature for 1 hour. The solvent was distilled off under reduced pressure and water was added, and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was used for the synthesis of (j).

(j) Synthesis of 3-(3-cyano-4-methoxy-5-trifluoromethylbenzoyl)-1,1-dioxo-2,3-dihydro-1,3-benzothiazole 3-(3-cyano-4-methoxy-5-trifluoromethylbenzoyl)-2,3-dihydro-1,3-benzothiazole was dissolved in chloroform (200 mL), and 70% metachloroperbenzoic acid (21.40 g) was added to the solution, and then the mixture was stirred at room temperature for 20 hours and quenched with 10% sodium thiosulfate. The solvent was distilled off under reduced pressure and 1N sodium hydroxide was added, and then the mixture was extracted with ethyl acetate. The organic layer was washed with 1N sodium hydroxide and saturated brine, and then dried over anhydrous sodium sulfate. The solvent was distilled off under reduced pressure to obtain the title compound (4.08 g) as a pale yellow solid.

(k) Synthesis of 3-(3-cyano-4-hydroxy-5-trifluoromethylbenzoyl)-1,1-dioxo-2,3-dihydro-1,3-benzothiazole 3-(3-cyano-4-methoxy-5-trifluoromethylbenzoyl)-1,1-dioxo-2,3-dihydro-1,3-benzothiazole (4.08 g) was dissolved in N,N-dimethylformamide (40 mL), and lithium chloride (1.74 g) was added to the solution, and then the mixture was stirred at 70° C. for 2 hours. To the reaction solution, 1N hydrochloric acid was added, and then the reaction mixture was extracted with ethyl acetate. The organic layer was washed with 1N hydrochloric acid and saturated brine, and then dried over anhydrous sodium sulfate. The solvent was distilled off under reduced pressure and the obtained residue was crystallized from n-hexane-ethyl acetate to obtain the title compound (222 g) as a colorless crystal.
1H-NMRδ (DMSO-d6): 5.37 (2H, s), 7.44 (1H, dd, J=7.8, 7.8 Hz), 7.77 (1H, ddd, J=7.9, 7.8, 1.3 Hz), 7.91 (1H, dd, J=7.8, 1.3 Hz), 8.09 (1H, d, J=7.9 Hz), 8.10 (1H, d, J=2.1 Hz), 8.27 (1H, d, J=2.1 Hz). MS (m/z): 381 (M-H)-.

Example 5

3-(3-cyano-4-hydroxy-5-trifluoromethylbenzoyl)-2,3-dihydro-1,3-benzothiazole 3-(3-cyano-4-methoxy-5-trifluoromethylbenzoyl)-2,3-dihydro-1,3-benzothiazole (232 mg) was dissolved in N,N-dimethylformamide (3 mL), and lithium chloride (108 mg) was added to the solution, and then the mixture was stirred at 70° C. for 1 hour. To the reaction solution, 1N hydrochloric acid was added, and then the mixture was extracted with ethyl acetate. The organic layer was washed with 1N hydrochloric acid and saturated brine, and then dried over anhydrous sodium sulfate. The solvent was distilled off under reduced pressure and the obtained residue was crystallized from n-hexane-ethyl acetate to obtain the title compound (131 mg) as a brown crystal.

1H-NMRδ (DMSO-d6): 5.38 (2H, s), 7.04-7.14 (2H, m), 7.32-7.38 (1H, m), 7.55 (1H, br), 8.05 (1H, d, J=2.1 Hz), 8.22 (1H, d, J=2.1 Hz). MS (m/z): 349 (M-H)-.

Example 6

3-(3-cyano-4-hydroxy-5-trifluoromethylbenzoyl)-1-oxo-2,3-dihydro-1,3-benzothiazole (a) Synthesis of 3-(3-cyano-4-methoxy-5-trifluoromethylbenzoyl)-1-oxo-2,3-dihydro-1,3-benzothiazole 3-(3-cyano-4-methoxy-5-trifluoromethylbenzoyl)-2,3-dihydro-1,3-benzothiazole (594 mg) was dissolved in chloroform (10 mL), and 70% metachloroperbenzoic acid (433 mg) was added to the solution, and then the mixture was stirred at 0° C. for 5 minutes. The organic solvent was distilled off under reduced pressure, and then 1N sodium hydroxide was added and the precipitated crystal was washed with 1N sodium hydroxide and water to obtain the title compound (619 mg) as a colorless crystal.

(b) Synthesis of 3-(3-cyano-4-hydroxy-5-trifluoromethylbenzoyl)-1-oxo-2,3-dihydro-1,3-benzothiazole 3-(3-cyano-4-methoxy-5-trifluoromethylbenzoyl)-1-oxo-2,3-dihydro-1,3-benzothiazole (619 mg) was dissolved in N,N-dimethylformamide (5 mL), and lithium chloride (276 mg) was added to the solution, and the mixture was stirred at 70° C. for 3 hours. To the reaction solution, 1N hydrochloric acid was added, and then the reaction mixture was extracted with ethyl acetate. The organic layer was washed with 1N hydrochloric acid and saturated brine, and then dried over anhydrous sodium sulfate. The solvent was distilled off under reduced pressure to obtain the title compound (494 mg) as a colorless crystal.

1H-NMRδ (DMSO-d6): 5.09 (1H, d, J=13.0 Hz), 5.15 (1H, d, J=13.0 Hz), 7.40 (1H, dd, J=7.5, 7.5 Hz), 7.72 (1H, ddd, J=7.5, 7.5, 1.0 Hz), 8.06 (1H, d, J=7.5 Hz), 8.09 (1H, d, J=7.5 Hz), 8.12 (1H, d, J=1.8 Hz), 8.30 (1H, d, J=1.8 Hz). MS (m/z): 365 (M-H)-.

Example 7

3-(3-chloro-5-cyano-4-hydroxybenzoyl)-1,1-dioxo-2,3-dihydro-1,3-benzothiazole (a) Synthesis of methyl 3-chloro-5-cyano-4-hydroxybenzoate Methyl 3-cyano-4-hydroxybenzoate (2.00 g) was dissolved in chloroform (15 mL) and methanol (5 mL), and N-chlorosuccinimide (3.62 g) and 4N hydrochloric acid-ethyl acetate (6.8 mL) were added to the solution, and then the mixture was stirred at room temperature for 1 hour. The solvent was distilled off under reduced pressure and a mixture of methanol and water in a mixing ratio of 9:1 was added, and then the precipitated crystal was washed with water and isopropyl alcohol to obtain the title compound (1.27 g) as a colorless crystal.

(b) Synthesis of methyl 3-chloro-5-cyano-4-methoxybenzoate

Methyl 3-chloro-5-cyano-4-hydroxybenzoate (1.27 g) was dissolved in N,N-dimethylformamide (20 mL), and potassium carbonate (5.00 g) and dimethylsulfuric acid (1.70 mL) were added to the solution, and then the mixture was stirred at room temperature for 18 hours. The reaction solution was filtered and water was added, and then the reaction mixture was extracted with ethyl acetate. The organic layer was washed with water and saturated brine, and then dried over anhydrous sodium sulfate. The solvent was distilled off under reduced pressure to obtain the title compound (1.03 g) as a colorless crystal.

(c) Synthesis of 3-chloro-5-cyano-4-methoxybenzoic acid

Methyl 3-chloro-5-cyano-4-methoxybenzoate (1.02 g) was dissolved in tetrahydrofuran (15 mL) and water (6 mL), and lithium hydroxide monohydrate (759 mg) was added to the solution, and then the mixture was stirred at room temperature for 90 minutes. The organic solvent was distilled off and the aqueous layer was washed with n-hexane. The aqueous layer was acidified with 1N hydrochloric acid and then extracted with ethyl acetate. The organic layer was washed with saturated brine, and then dried over anhydrous sodium sulfate. The solvent was distilled off under reduced pressure to obtain the title compound (946 mg) as a colorless crystal.

1H-NMRδ (DMSO-d6): 4.43 (3H, s), 8.55 (2H, s), 14.00 (1H, brs). MS (m/z): 210 (M-H)-, 212 (M+2-H)-.

(d) Synthesis of 3-chloro-5-cyano-4-methoxybenzoyl chloride

To 3-chloro-5-cyano-4-methoxybenzoic acid (932 mg), toluene (9.3 mL), N,N-dimethylformamide (0.03 mL) and thionyl chloride (0.38 mL) were added, and the mixture was stirred at 60° C. for 16 hours. The solvent was distilled off under reduced pressure and then azeotroped with toluene to obtain the title compound (993 mg) as a brown solid.

(e) Synthesis of 3-(3-chloro-5-cyano-4-methoxybenzoyl)-2,3-dihydro-1,3-benzothiazole 2,3-dihydro-1,3-benzothiazole synthesized from 2-aminobenzenethiol (810 mg) and 37% formalin (0.53 mL) in the same manner as in the synthesis of Example 1 was dissolved in dichloromethane (15 mL), and triethylamine (1.90 mL) and 3-chloro-5-cyano-4-methoxybenzoyl chloride (993 mg) were added to the solution, and then the mixture was stirred at room temperature for 1.5 hours. The solvent was distilled off under reduced pressure and water was added, and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was purified by silica gel column chromatography (n-hexane:ethyl acetate=6:1) to obtain the title compound (580 mg) as a yellow oily substance.

(f) Synthesis of 3-(3-chloro-5-cyano-4-methoxybenzoyl)-1,1-dioxo-2,3-dihydro-1,3-benzothiazole 3-(3-chloro-5-cyano-4-methoxybenzoyl)-2,3-dihydro-1,3-benzothiazole (187 mg) was dissolved in dichloromethane (2 mL), and 70% metachloroperbenzoic acid (607 mg) was added to the solution. After stirring the mixture at room temperature for 5 hours, 1N sodium hydroxide was added and then the mixture was extracted with ethyl acetate. The organic layer was washed with 1N sodium hydroxide and saturated brine, and then dried over anhydrous sodium sulfate. The solvent was distilled off under reduced pressure to obtain the title compound (183 mg) as a pale yellow solid.

(g) Synthesis of 3-(3-chloro-5-cyano-4-hydroxybenzoyl)-1,1-dioxo-2,3-dihydro-1,3-benzothiazole 3-(3-chloro-5-cyano-4-methoxybenzoyl)-1,1-dioxo-2,3-dihydro-1,3-benzothiazole (180 mg) was dissolved in N,N-dimethylformamide (2 mL), and lithium chloride (87 mg) was added to the solution, and then the mixture was stirred at 100° C. for 1 hour. To the reaction solution, 1N hydrochloric acid was added, and then reaction mixture was extracted with ethyl acetate. The organic layer was washed with 1N hydrochloric acid and saturated brine, and then dried over anhydrous sodium sulfate. The solvent was distilled off under reduced pressure and the obtained residue was crystallized from n-hexane-chloroform to obtain the title compound (146 mg) as a pale yellow crystal.

1H-NMRδ (DMSO-d6): 5.32 (2H, s), 7.44 (1H, ddd, J=8.4, 7.3, 0.8 Hz), 7.75 (1H, ddd, J=8.6, 7.3, 1.4 Hz), 7.88 (1H, dd, J=8.4, 1.4 Hz), 7.99 (1H, d, J=2.2 Hz), 8.00 (1H, d, J=2.2 Hz), 8.06 (1H, d, J=8.6 Hz). MS (m/z): 347 (M-H)-.

Example 8

3-(3-chloro-5-cyano-4-hydroxybenzoyl)-2,3-dihydro-1,3-benzothiazole 3-(3-chloro-5-cyano-4-methoxybenzoyl)-2,3-dihydro-1,3-benzothiazole (213 mg) was dissolved in N,N-dimethylformamide (2 mL), and lithium chloride (111 mg) was added to the solution, and then the mixture was stiffed at 100° C. for 2 hours. To the reaction solution, 1N hydrochloric acid was added, and then the reaction mixture was extracted with ethyl acetate. The organic layer was washed with 1N hydrochloric acid and saturated brine, and then dried over anhydrous sodium sulfate. The solvent was distilled off under reduced pressure and the obtained residue was purified by silica gel column chromatography (ethyl acetate:methanol=10:1), and then crystallized from n-hexane-chloroform to obtain the title compound (68 mg) as a pale yellow crystal.

1H-NMRδ (DMSO-d6): 5.37 (2H, s), 7.01-7.16 (2H, m), 7.33 (1H, dd, J=6.5, 2.2 Hz), 7.45 (1H, d, J=7.0 Hz), 7.79 (1H, s), 7.81 (1H, s). MS (m/z): 315 (M-H)-.

Example 9

3-(3-t-butyl-5-cyano-4-hydroxybenzoyl)-1,1-dioxo-2,3-dihydro-1,3-benzothiazole

(a) Synthesis of methyl 3-t-butyl-4-hydroxybenzoate

Methyl 4-hydroxybenzoate (3.00 g) was dissolved in methanesulfonic acid (15 mL), and 2-bromo-2-methylpropane (11.1 mL) was added to the solution, and then the mixture was stirred at 70° C. for 16 hours. To the reaction solution, methanol (20 mL) was added, and then the reaction mixture was stirred at 50° C. for 3 hours. 1N potassium hydroxide was added, and then the mixture was extracted with ethyl acetate. The organic layer was washed with an aqueous 10% potassium carbonate solution and saturated brine, and then dried over anhydrous sodium sulfate. The solvent was distilled off under reduced pressure and the obtained residue was purified by silica gel column chromatography (n-hexane:ethyl acetate=3:1) to obtain the title compound (1.83 g) as a pale yellow crystal.

(b) Synthesis of methyl 3-t-butyl-4-hydroxy-5-iodobenzoate

Methyl 3-t-butyl-4-hydroxybenzoate (1.83 g) was dissolved in dichloromethane (24 mL) and methanol (3 mL), and N-iodosuccinimide (2.08 g) and trifluoromethanesulfonic acid (3 mL) were added to the solution, and then the mixture was stirred at room temperature for 15 minutes. Water was added to the reaction solution, and then the organic layer was separated. The organic layer was washed with 10% sodium thiosulfate and saturated brine, and then dried over anhydrous sodium sulfate. The solvent was distilled off under reduced pressure to obtain the title compound (2.77 g) as a brown crystal.

(c) Synthesis of methyl 3-t-butyl-5-iodo-4-methoxybenzoate

Methyl 3-t-butyl-4-hydroxy-5-iodobenzoate (2.77 g) was dissolved in N,N-dimethylformamide (50 mL), and potassium carbonate (12.0 g) and dimethylsulfuric acid (4.1 mL) were added to the solution, and then the mixture was stirred at room temperature for 16 hours. Water was added to the reaction solution, and then the reaction mixture was extracted with ethyl acetate. The organic layer was washed with water and saturated brine, and then dried over anhydrous sodium sulfate. The solvent was distilled off under reduced pressure to obtain the title compound (2.77 g) as a brown crystal.

(d) Synthesis of methyl 3-t-butyl-5-cyano-4-methoxybenzoate

Methyl 3-t-butyl-5-iodo-4-methoxybenzoate (2.77 g) was dissolved in N,N-dimethylformamide (30 mL), and copper cyanide (965 mg) was added to the solution, and then the mixture was stirred at 150° C. for 2.5 hours. To the reaction solution, 10% potassium carbonate was added, and then the mixture was extracted with ethyl acetate. The organic layer was washed with water and saturated brine, and then dried over anhydrous sodium sulfate. The solvent was distilled off under reduced pressure and the obtained residue was purified by silica gel column chromatography (n-hexane:ethyl acetate=3:1) to obtain the title compound (1.48 g) as a yellow oily substance.

(e) Synthesis of 3-t-butyl-5-cyano-4-methoxybenzoic acid

Methyl 3-t-butyl-5-cyano-4-methoxybenzoate (1.48 g) was dissolved in methanol (20 ml), tetrahydrofuran (5 mL) and water (5 mL), and lithium hydroxide monohydrate (753 mg) was added to the solution, and then the mixture was stirred at room temperature for 2 hours. To the reaction solution, 10% hydrochloric acid was added, and then the mixture was extracted with ethyl acetate. The organic layer was washed with saturated brine, and then dried over anhydrous sodium sulfate. The solvent was distilled off under reduced pressure to obtain the title compound (1.18 g) as a pale yellow crystal.

1H-NMRδ (CDCl3): 1.41 (9H, s), 4.26 (3H, s), 8.23 (1H, d, J=2.2 Hz), 8.25 (1H, d, J=2.2 Hz).

(f) Synthesis of 3-t-butyl-5-cyano-4-methoxybenzoyl chloride

To 3-t-butyl-5-cyano-4-methoxybenzoic acid (586 mg), toluene (10 mL), N,N-dimethylformamide (2 droplets) and thionyl chloride (0.27 mL) was added, and the mixture was stirred at 60° C. for 16 hours. The solvent was distilled off under reduced pressure and then azeotroped with toluene to obtain the title compound (630 mg) as a brown oily substance.

(g) Synthesis of 3-(3-t-butyl-5-cyano-4-methoxybenzoyl)-2,3-dihydro-1,3-benzothiazole 2,3-dihydro-1,3-benzothiazole synthesized from 2-aminobenzenethiol (943 mg) and 37% formalin (0.57 mL) in the same manner as in Example 1 was dissolved in chloroform (15 mL), and triethylamine (1.04 mL) and 3-t-butyl-5-cyano-4-methoxybenzoyl chloride (630 mg) was added to the solution, and then the mixture was stirred at room temperature for 1 hour. The solvent was distilled off under reduced pressure and water was added, and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was purified by silica gel column chromatography (n-hexane:ethyl acetate=6:1) to obtain the title compound (904 mg) as a yellow oily substance.

(h) Synthesis of 3-(3-t-butyl-5-cyano-4-methoxybenzoyl)-1,1-dioxo-2,3-dihydro-1,3-benzothiazole 3-(3-t-butyl-5-cyano-4-methoxybenzoyl)-2,3-dihydro-1,3-benzothiazole (452 mg) was dissolved in chloroform (9 mL), and 70% metachloroperbenzoic acid (1.02 g) was added to the solution, and then the mixture was stirred at room temperature for 16 hours and quenched with 10% sodium thiosulfate. The solvent was distilled off under reduced pressure and 1N sodium hydroxide was added, and then the mixture was extracted with ethyl acetate. The organic layer was washed with 1N sodium hydroxide and saturated brine, and then dried over anhydrous sodium sulfate. The solvent was distilled off under reduced pressure to obtain the title compound (439 mg) as a pale yellow oily substance.

1H-NMRδ (CDCl3): 1.36 (9H, s), 4.27 (3H, s), 4.93 (2H, s), 7.37 (1H, ddd, J=7.8, 7.1, 1.3 Hz), 7.58 (1H, ddd, J=8.2, 7.1, 1.3 Hz), 7.65 (1H, d, J=2.3 Hz), 7.70 (1H, d, J=2.3 Hz), 7.72 (1H, d, J=2.3 Hz), 7.76-7.80 (1H, m).

(i) Synthesis of 3-(3-t-butyl-5-cyano-4-hydroxybenzoyl)-1,1-dioxo-2,3-dihydro-1,3-benzothiazole 3-(3-t-butyl-5-cyano-4-methoxybenzoyl)-1,1-dioxo-2,3-dihydro-1,3-benzothiazole (364 mg) was dissolved in N,N-dimethylformamide (4 mL), and lithium chloride (401 mg) was added to the solution, and then the mixture was stirred at 120° C. for 16 hours. To the reaction solution, 1N hydrochloric acid was added, and then the mixture was extracted with ethyl acetate. The organic layer was washed with 1N hydrochloric acid and saturated brine, and then dried over anhydrous sodium sulfate. The solvent was distilled off under reduced pressure and the obtained residue was crystallized from n-hexane-ethyl acetate to obtain the title compound (299 mg) as a colorless crystal.

1H-NMRδ (DMSO-d6): 1.37 (9H, s), 5.35 (2H, s), 7.43 (1H, dd, J=7.4, 7.4 Hz), 7.73 (1H, d, J=2.1 Hz), 7.75 (1H, ddd, J=7.4, 7.4, 1.2 Hz), 7.88-7.93 (2H, m), 8.01 (1H, d, J=8.2 Hz), 11.23 (1H, brs). MS (m/z): 369 (M-H)-.

Example 10

3-(3-cyano-4-hydroxy-5-isopropylbenzoyl)-1,1-dioxo-2,3-dihydro-1,3-benzothiazole (a) Synthesis of 5-bromo-2-hydroxy-3-isopropylbenzaldehyde 2-hydroxy-3-isopropylbenzaldehyde (20.19 g) was dissolved in acetonitrile (160 mL), and N-bromosuccinimide (17.80 g) was added to the solution at 0° C., and then the mixture was stirred at room temperature for 4 hours. The solvent was distilled off under reduced pressure and water was added, and then the mixture was extracted with ethyl acetate. The organic layer was washed with saturated brine, and then dried over anhydrous sodium sulfate. The solvent was distilled off under reduced pressure to obtain the title compound (25.88 g) as a yellow oily substance.

(b) Synthesis of 5-bromo-3-isopropyl-2-methoxybenzaldehyde 5-bromo-2-hydroxy-3-isopropylbenzaldehyde (25.88 g) was dissolved in N,N-dimethylformamide (100 mL), and potassium carbonate (27.64 g) and dimethylsulfuric acid (9.5 mL) were added to the solution under water cooling, and the mixture was stirred at room temperature for 2 hours. Water was added to the reaction solution, and then the reaction mixture was extracted with ethyl acetate. The organic layer was washed with water and saturated brine, and then dried over anhydrous sodium sulfate. The solvent was distilled off under reduced pressure to obtain the title compound (26.76 g) as a brown oily substance.

(c) Synthesis of 5-bromo-1-diethoxymethyl-3-isopropyl-2-methoxybenzene 5-bromo-3-isopropyl-2-methoxybenzaldehyde (26.76 g) was dissolved in n-hexane (50 mL) and triethyl orthoformate (22 mL), and Amberlyst-15 (2.68 g) was added to the solution, and then the mixture was refluxed for 4 hours. The reaction solution was filtered, and then the solvent was distilled off under reduced pressure to obtain the title compound (31.55 g) as a brown oily substance.

(d) Synthesis of 3-formyl-5-isopropyl-4-methoxybenzoic acid

To magnesium (2.43 g), tetrahydrofuran (100 mL), 5-bromo-1-diethoxymethyl-3-isopropyl-2-methoxybenzene (31.55 g) and a 0.97M methylmagnesium bromide-tetrahydrofuran solution (15 mL) were added, and then the mixture was stirred at room temperature for 2 hours. The reaction solution was cooled to 0° C. and stirred under a carbon dioxide atmosphere for 30 minutes, and then 2N hydrochloric acid (100 mL) was added and the reaction mixture was stirred at room temperature for 16 hours. The organic solvent was distilled off under reduced pressure, and then the mixture was extracted with diisopropylether. The organic layer was extracted with 1N sodium hydroxide (100 mL) added thereto, and then the aqueous layer was washed twice with diisopropylether. The aqueous layer was acidified with 4N hydrochloric acid added thereto, and then extracted with ethyl acetate. The organic layer was washed with saturated brine, and then dried over anhydrous sodium sulfate. The solvent was distilled off under reduced pressure to obtain the title compound (15.85 g) as a brown solid.

(e) Synthesis of 3-cyano-5-isopropyl-4-methoxybenzoic acid 3-formyl-5-isopropyl-4-methoxybenzoic acid (15.85 g) was dissolved in formic acid (80 mL), and hydroxylamine hydrochloride (5.45 g) was added to the solution, and the mixture was refluxed for 19 hours. The solvent was distilled off under reduced pressure and water was added, and then the mixture was extracted with ethyl acetate. The organic layer was washed with saturated brine, and then dried over anhydrous sodium sulfate. The solvent was distilled off under reduced pressure to obtain the title compound (15.62 g) as a brown solid.

1H-NMRδ (DMSO-d6): 1.21 (6H, d, J=6.9 Hz), 3.29 (1H, sevent, J=6.9 Hz), 4.04 (3H, s), 8.10 (1H, s). MS (m/z): 218 (M-H)-.

(f) Synthesis of 3-cyano-5-isopropyl-4-methoxybenzoyl chloride

To 3-cyano-5-isopropyl-4-methoxybenzoic acid (658 mg), toluene (7 mL), N,N-dimethylformamide (2 droplets) and thionyl chloride (0.33 mL) were added, and the mixture was stirred at 60° C. for 16 hours. The solvent was distilled off under reduced pressure and then azeotroped with toluene to obtain the title compound (710 mg) as a brown oily substance.

(g) Synthesis of 3-(3-cyano-5-isopropyl-4-methoxybenzoyl)-2,3-dihydro-1,3-benzothiazole 2,3-dihydro-1,3-benzothiazole synthesized from 2-aminobenzenethiol (1.25 g) and 37% formalin (0.83 mL) in the same manner as in Example 1 was dissolved in chloroform (7 mL), and triethylamine (1.25 mL) and 3-cyano-5-isopropyl-4-methoxybenzoyl chloride (710 mg) were added to the solution, and then the mixture was stirred at room temperature for 2 hours. The solvent was distilled off under reduced pressure and water was added, and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was purified by silica gel column chromatography (n-hexane:ethyl acetate=6:1) to obtain the title compound (1.02 g) as a yellow oily substance.

(h) Synthesis of 3-(3-cyano-5-isopropyl-4-methoxybenzoyl)-1,1-dioxo-2,3-dihydro-1,3-benzothiazole 3-(3-cyano-5-isopropyl-4-methoxybenzoyl)-2,3-dihydro-1,3-benzothiazole (501 mg) was dissolved in chloroform (5 mL), and 70% metachloroperbenzoic acid (996 mg) was added to the solution, and then the mixture was stirred at room temperature for 18 hours and quenched with 10% sodium thio sulfate. The solvent was distilled off under reduced pressure and 1N sodium hydroxide was added, and then the mixture was extracted with ethyl acetate. The organic layer was washed with 1N sodium hydroxide and saturated brine, and then dried over anhydrous sodium sulfate. The solvent was distilled off under reduced pressure and the obtained residue was purified by silica gel column chromatography (n-hexane:ethyl acetate=3:1) to obtain the title compound (439 mg) as a brown amorphous product.

(i) Synthesis of 3-(3-cyano-4-hydroxy-5-isopropylbenzoyl)-1,1-dioxo-2,3-dihydro-1,3-benzothiazole 3-(3-cyano-5-isopropyl-4-methoxybenzoyl)-1,1-dioxo-2,3-dihydro-1,3-benzothiazole (434 mg) was dissolved in N,N-dimethylformamide (5 mL), and lithium chloride (496 mg) was added to the solution, and then the mixture was stirred at 100° C. for 20 hours. To the reaction solution, 1N hydrochloric acid was added, and then the reaction mixture was extracted with ethyl acetate. The organic layer was washed with 1N hydrochloric acid and saturated brine, and then dried over anhydrous sodium sulfate. The solvent was distilled off under reduced pressure and the obtained residue was crystallized from n-hexane-chloroform to obtain the title compound (351 mg) as a colorless crystal.

1H-NMRδ (DMSO-d6): 1.18 (6H, d, J=6.8 Hz), 3.35 (1H, sevent, J=6.8 Hz), 5.34 (2H, s), 7.43 (1H, ddd, J=7.8, 7.8, 0.8 Hz), 7.75 (1H, ddd, J=8.4, 7.8, 1.3 Hz), 7.76 (1H, d, J=2.3 Hz), 7.87 (1H, d, J=2.3 Hz), 7.90 (1H, dd, J=7.8, 0.8 Hz), 8.00 (1H, d, J=8.4 Hz). MS (m/z): 355 (M-H)-.

Example 11

3-(3-cyano-5-cyclobutyl-4-hydroxybenzoyl)-1,1-dioxo-2,3-dihydro-1,3-benzothiazole

(a) Synthesis of 1-cyclobutyl-2-methoxymethoxybenzene 2-cyclobutylphenol (871 mg) was dissolved in N,N-dimethylformamide (5 mL), and 60% sodium hydride (1.30 g) was added to the solution at 0° C. After stirring the mixture for 30 minutes, chloromethyl methyl ether (2.1 mL) was added and the mixture was stirred for 14 hours. Water was added to the reaction solution, and then the reaction mixture was extracted with ethyl acetate. The organic layer was washed with water and saturated brine, and then dried over anhydrous sodium sulfate. The solvent was distilled off under reduced pressure and the obtained residue was purified by silica gel column chromatography (n-hexane:ethyl acetate=10:1) to obtain the title compound (1.13 g) as a colorless oily substance.

(b) Synthesis of 3-cyclobutyl-2-hydroxybenzaldehyde 1-cyclobutyl-2-methoxymethoxybenzene (1.18 g) was dissolved in tetrahydrofuran (11 mL), and a 1.01M s-butyl-lithium-cyclohexane solution (8.7 mL) was added to the solution at −60° C. over 15 minutes under an argon gas flow, and then the mixture was stirred for 2 hours. N,N-dimethylformamide (0.90 mL) was added and the mixture was stirred at the same temperature for 2 hours. 4N hydrochloric acid (15 mL) was added at room temperature, and then the mixture was stirred at 60° C. for 20 hours. The solvent was distilled off under reduced pressure and water was added, and then the mixture was extracted with ethyl acetate. The organic layer was washed with saturated brine, and then dried over anhydrous sodium sulfate. The solvent was distilled off under reduced pressure and the obtained residue was purified by silica gel column chromatography (n-hexane:ethyl acetate=20:1) to obtain the title compound (0.95 g) as a colorless oily substance.

(c) Synthesis of 5-bromo-3-cyclobutyl-2-hydroxybenzaldehyde 3-cyclobutyl-2-hydroxybenzaldehyde (2.29 g) was dissolved in acetonitrile (30 mL), and N-bromosuccinimide (5.10 g) was added to the solution at 0° C., and then the mixture was stirred at room temperature for 4 hours. The solvent was distilled off under reduced pressure and water was added, and then the mixture was extracted with ethyl acetate. The organic layer was washed with water and saturated brine, and then dried over anhydrous sodium sulfate. The solvent was distilled off under reduced pressure and the obtained residue was used for the synthesis of (d).

(d) Synthesis of 5-bromo-3-cyclobutyl-2-methoxybenzaldehyde 5-bromo-3-cyclobutyl-2-hydroxybenzaldehyde was dissolved in N,N-dimethylformamide (30 mL), and potassium carbonate (10.79 g) and dimethylsulfuric acid (3.7 mL) were added to the solution under water cooling, and then the mixture was stirred at room temperature for 14 hours. The reaction solution was filtered and water was added, and then the reaction mixture was extracted with ethyl acetate. The organic layer was washed with saturated brine, and then dried over anhydrous sodium sulfate. The solvent was distilled off under reduced pressure and the obtained residue was purified by silica gel column chromatography (n-hexane:ethyl acetate=20:1) to obtain the title compound (1.27 g) as a yellow oily substance.

(e) Synthesis of 5-bromo-3-cyclobutyl-1-diethoxymethyl-2-methoxybenzene 5-bromo-3-cyclobutyl-2-methoxybenzaldehyde (1.15 g) was dissolved in n-hexane (5 mL) and triethyl orthoformate (0.93 mL), and Amberlyst-15 (115 mg) was added to the solution, and then the mixture was refluxed for 3 hours. The reaction solution was filtered, and then the solvent was distilled off under reduced pressure to obtain the title compound (1.33 g) as a yellow oily substance.

(f) Synthesis of 3-cyclobutyl-5-formyl-4-methoxybenzoic acid

To magnesium (106 mg), tetrahydrofuran (3.5 mL), 5-bromo-3-cyclobutyl-1-diethoxymethyl-2-methoxybenzene (1.33 g) and a 0.97M methylmagnesium bromide-tetrahydrofuran solution (1.32 mL) was added, and then the mixture was stirred at room temperature for 1.5 hours. The reaction solution was cooled to 0° C. and stirred under a carbon dioxide atmosphere for 15 hours, and then 2N hydrochloric acid (10 mL) was added and the mixture was stirred at mom temperature for 1 hour. The organic solvent was distilled off under reduced pressure and then extracted with diisopropylether. The organic layer was extracted with 1N sodium hydroxide added thereto, and then the aqueous layer was washed twice with diisopropylether. The aqueous layer was acidified with 4N hydrochloric acid added thereto, and then extracted with ethyl acetate. The organic layer was washed with saturated brine, and then dried over anhydrous sodium sulfate. The solvent was distilled off under reduced pressure to obtain the title compound (458 mg) as a brown solid.

(g) Synthesis of 3-cyano-5-cyclobutyl-4-methoxybenzoic acid 3-cyclobutyl-5-formyl-4-methoxybenzoic acid (458 mg) was dissolved in formic acid (2.5 mL), and hydroxylamine hydrochloride (163 mg) was added to the solution, and then the mixture was refluxed for 19 hours. The solvent was distilled off under reduced pressure and water was added, and then the mixture was extracted with ethyl acetate. The organic layer was washed with saturated brine, and then dried over anhydrous sodium sulfate. The solvent was distilled off under reduced pressure to obtain the title compound (404 mg) as a brown solid.

1H-NMRδ (CDCl3): 1.82-2.48 (6H, m), 3.76 (1H, quint, J=8.7 Hz), 4.15 (3H, s), 8.18 (1H, d, J=2.2 Hz), 8.20 (1H, d, J=2.2 Hz). MS (m/z): 230 (M-H)-.

(h) Synthesis of 3-cyano-5-cyclobutyl-4-methoxybenzoyl chloride

To 3-cyano-5-cyclobutyl-4-methoxybenzoic acid (190 mg), toluene (2.0 mL), N,N-dimethylformamide (1 droplet) and thionyl chloride (0.07 mL) were added, and the mixture was stirred at 60° C. for 3 hours. The solvent was distilled off under reduced pressure and then azeotroped with toluene to obtain the title compound (204 mg) as a brown oily substance.

(i) Synthesis of 3-(3-cyano-5-cyclobutyl-4-methoxybenzoyl)-2,3-dihydro-1,3-benzothiazole 2,3-dihydro-1,3-benzothiazole synthesized from 2-aminobenzenethiol (153 mg) and 37% formalin (0.10 mL) in the same manner as in Example 1 was dissolved in dichloromethane (3 mL), and triethylamine (0.34 mL) and 3-cyano-5-cyclobutyl-4-methoxybenzoyl chloride (204 mg) were added to the solution, and then the mixture was stirred at room temperature for 1 hour. The solvent was distilled off under reduced pressure and water was added, and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was used for the synthesis of (j).

(j) Synthesis of 3-(3-cyano-5-cyclobutyl-4-methoxybenzoyl)-1,1-dioxo-2,3-dihydro-1,3-benzothiazole 3-(3-cyano-5-cyclobutyl-4-methoxybenzoyl)-2,3-dihydro-1,3-benzothiazole was dissolved in dichloromethane (4 mL), and 70% metachloroperbenzoic acid (1.62 g) was added to the solution. After stirring the mixture at room temperature for 28 hours, 1N sodium hydroxide was added and then the mixture was extracted with ethyl acetate. The organic layer was washed with 1N sodium hydroxide and saturated brine, and then dried over anhydrous sodium sulfate. The solvent was distilled off under reduced pressure to obtain the title compound (156 mg) as a yellow solid.

(k) Synthesis of 3-(3-cyano-5-cyclobutyl-4-hydroxybenzoyl)-1,1-dioxo-2-dihydro-1,3-benzothiazole 3-(5-cyano-3-cyclobutyl-4-methoxybenzoyl)-1,1-dioxo-2,3-dihydro-1,3-benzothiazole (150 mg) was dissolved in N,N-dimethylformamide (1.5 mL), and lithium chloride (248 mg) was added to the solution, and then the mixture was stirred at 120° C. for 2.5 hours. To the reaction solution, 1N hydrochloric acid was added, and then the mixture was extracted with ethyl acetate. The organic layer was washed with 1N hydrochloric acid and saturated brine, and then dried over anhydrous sodium sulfate. The solvent was distilled off under reduced pressure and the obtained residue was crystallized from n-hexane-chloroform to obtain the title compound (95 mg) as a brown crystal.

1H-NMRδ (DMSO-d6): 1.72-2.18 (4H, m), 2.25-2.39 (2H, m), 3.77 (1H, quint, J=8.7 Hz), 5.35 (2H, s), 7.44 (1H, dd, J=7.6, 7.6 Hz), 7.77 (1H, dd, J=8.4, 7.6 Hz), 7.79 (1H, d, J=2.2 Hz), 7.87 (1H, d, J=2.2 Hz), 7.91 (1H, d, J=7.6 Hz), 8.04 (1H, d, J=8.4 Hz). MS (m/z): 367 (M-H)-.

Example 12

3-(3-cyano-5-ethyl-4-hydroxybenzoyl)-1,1-dioxo-2,3-dihydro-1,3-benzothiazole (a) Synthesis of methyl 3-cyano-4-methoxy-5-trimethylsilanylethynyl benzoate Methyl 3-cyano-5-iodo-4-methoxybenzoate (2.13 g) was dissolved in tetrahydrofuran (30 mL), and triethylamine (10 mL), copper iodide (256 mg), tetrakistriphenylphosphine palladium (777 mg) and trimethylsilylacetylene (858 mg) were added to the solution, and then the mixture was stirred at room temperature for 1 hour. The solvent was distilled off under reduced pressure and the obtained residue was purified by silica gel column chromatography (n-hexane:ethyl acetate=4:1) to obtain the title compound (2.03 g) as a brown oily substance.

(b) Synthesis of methyl 3-cyano-5-ethynyl-4-methoxybenzoate

Methyl 3-cyano-4-methoxy-5-trimethylsilanylethynyl benzoate (2.03 g) was dissolved in tetrahydrofuran (20 mL), and an aqueous 1N sodium hydroxide solution (8 mL) was added to the solution, and then the mixture was stirred at room temperature for 10 minutes. The solvent was distilled off under reduced pressure and 1N hydrochloric acid was added, and the mixture was extracted with ethyl acetate. The organic layer was washed with saturated brine, and then dried over anhydrous sodium sulfate. The solvent was distilled off under reduced pressure to obtain the title compound (1.37 g) as a colorless crystal.

(c) Synthesis of methyl 3-cyano-5-ethyl-4-methoxybenzoate

Methyl 3-cyano-5-ethynyl-4-methoxybenzoate (475 mg) was dissolved in tetrahydrofuran (10 mL), and 5% palladium-carbon (150 mg) was added to the solution, and then the mixture was stirred under a hydrogen atmosphere at room temperature for 30 minutes. The reaction solution was filtered, and then the solvent was distilled off under reduced pressure and the obtained residue was purified by silica gel column chromatography (n-hexane:ethyl acetate=5:1) to obtain the title compound (480 mg) as a colorless crystal.

(d) Synthesis of 3-cyano-5-ethyl-4-methoxybenzoic acid

Methyl 3-cyano-5-ethyl-4-methoxybenzoate (480 mg) was dissolved in tetrahydrofuran (6 mL) and water (2 mL), and lithium hydroxide monohydrate (370 mg) was added to the solution, and then the mixture was stirred at room temperature for 5 hours. The solvent was distilled off under reduced pressure and 1N hydrochloric acid was added, and then the mixture was extracted with ethyl acetate. The organic layer was washed with saturated brine, and then dried over anhydrous sodium sulfate. The solvent was distilled off under reduced pressure to obtain the title compound (403 mg) as a colorless crystal.

1H-NMRδ (DMSO-d6): 1.50 (3H, t, J=7.5 Hz), 3.01 (2H, q, J=7.5 Hz), 4.36 (3H, s), 8.40 (1H, d, J=2.1 Hz), 8.41 (1H, d, J=2.1 Hz). MS (m/z): 204 (M-H)-.

(e) Synthesis of 3-cyano-5-ethyl-4-methoxybenzoyl chloride

To 3-cyano-5-ethyl-4-methoxybenzoic acid (347 mg), toluene (3.5 mL), N,N-dimethylformamide (0.01 mL) and thionyl chloride (0.15 mL) were added, and then the mixture was stirred at 60° C. for 14 hours. The solvent was distilled off under reduced pressure and then azeotroped with toluene to obtain the title compound (387 mg) as a brown oily substance.

(f) Synthesis of 3-(3-cyano-5-ethyl-4-methoxybenzoyl)-2,3-dihydro-1,3-benzothiazole 2,3-dihydro-1,3-benzothiazole synthesized from 2-aminobenzenethiol (318 mg) and 37% formalin (0.21 mL) in the same manner as in Example 1 was dissolved in dichloromethane (6 mL), and triethylamine (0.71 mL) and 3-cyano-5-ethyl-4-methoxybenzoyl chloride (387 mg) were added to the solution, and then the mixture was stirred at room temperature for 1.5 hours. The solvent was distilled off under reduced pressure and water was added, and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was purified by silica gel column chromatography (n-hexane:ethyl acetate=6:1) to obtain the title compound (498 mg) as a yellow oily substance.

(g) Synthesis of 3-(3-cyano-5-ethyl-4-methoxybenzoyl)-1,1-dioxo-2,3-dihydro-1,3-benzothiazole 3-(3-cyano-5-ethyl-4-methoxybenzoyl)-2,3-dihydro-1,3-benzothiazole (366 mg) was dissolved in dichloromethane (7 mL), and 70% metachloroperbenzoic acid (1.20 g) was added to the solution. After stirring the mixture at room temperature for 14 hours, 1N sodium hydroxide was added and the mixture was extracted with ethyl acetate. The organic layer was washed with 1N sodium hydroxide and saturated brine, and then dried over anhydrous sodium sulfate. The solvent was distilled off under reduced pressure to obtain the title compound (309 mg) as a colorless solid.

(h) Synthesis of 3-(3-cyano-5-ethyl-4-hydroxybenzoyl)-1,1-dioxo-2,3-dihydro-1,3-benzothiazole 3-(3-cyano-5-ethyl-4-methoxybenzoyl)-1,1-dioxo-2,3-dihydro-1,3-benzothiazole (309 mg) was dissolved in N,N-dimethylformamide (3 mL), and lithium chloride (443 mg) was added to the solution, and then the mixture was stirred at 120° C. for 2.5 hours. To the reaction solution, 1N hydrochloric acid was added, and then the mixture was extracted with ethyl acetate. The organic layer was washed with 1N hydrochloric acid and saturated brine, and then dried over anhydrous sodium sulfate. The solvent was distilled off under reduced pressure and the obtained residue was crystallized from n-hexane-chloroform to obtain the title compound (257 mg) as a brown crystal.

1H-NMRδ (DMSO-d6): 1.15 (3H, t, J=7.6 Hz), 2.68 (2H, q, J=7.6 Hz), 5.34 (2H, s), 7.43 (1H, dd, J=7.6, 7.6 Hz), 7.74 (1H, d, J=2.2 Hz), 7.75 (1H, dd, J=8.4, 7.6 Hz), 7.88 (1H, d,

J=2.2 Hz), 7.90 (1H, d, J=7.6 Hz), 8.00 (1H, d, J=8.4 Hz), 11.01 (1H, brs). MS (m/z): 341 (M-H)-.

Example 13

3-(3-cyano-5-cyclopropyl-4-hydroxybenzoyl)-1,1-dioxo-2,3-dihydro-1,3-benzothiazole

(a) Synthesis of methyl 3-cyano-5-cyclopropyl-4-methoxybenzoate

Methyl 3-cyano-4-hydroxy-5-iodobenzoate (1.00 g) was dissolved in 1,4-dioxane (15 mL), and potassium carbonate (1.31 g), cyclopropylboronic acid (325 mg) and [1,3-bis-(2,6-diisopropylphenyl)imidazol-2-ylidene](3-chloropyridyl)palladium dichloride (108 mg) were added to the solution, and then the mixture was stirred under an argon gas flow at 95° C. for 22 hours. The reaction solution was filtered and the solvent was distilled off under reduced pressure, and then the obtained residue was purified by silica gel column chromatography (n-hexane:ethyl acetate=4:1) to obtain the title compound (348 mg) as a pale yellow crystal.

(b) Synthesis of 3-cyano-5-cyclopropyl-4-methoxybenzoic acid

Methyl 3-cyano-5-cyclopropyl-4-methoxybenzoate (491 mg) was dissolved in tetrahydrofuran (7.5 mL) and water (2.5 mL), and lithium hydroxide monohydrate (359 mg) was added to the solution, and then the mixture was stirred at mom temperature for 20 hours. The organic solvent was distilled off under reduced pressure and the aqueous layer was washed with n-hexane. To the aqueous layer, 1N hydrochloric acid was added, and the mixture was extracted with ethyl acetate under acidic conditions. The organic layer was washed with saturated brine, and then dried over anhydrous sodium sulfate. The solvent was distilled off under reduced pressure to obtain the title compound (394 mg) as a pale brown crystal.

1H-NMRδ (DMSO-d6): 0.74-0.79 (2H, m), 1.03-1.10 (2H, m), 2.13-2.23 (1H, m), 4.06 (3H, s), 7.65 (1H, d, J=2.0 Hz), 8.04 (1H, d, J=2.0 Hz). MS (m/z): 216 (M-H)-.

(c) Synthesis of 3-cyano-5-cyclopropyl-4-methoxybenzoyl chloride

To 3-cyano-5-cyclopropyl-4-methoxybenzoic acid (200 mg), toluene (2 mL), N,N-dimethylformamide (1 droplet) and thionyl chloride (0.10 mL) were added, and the mixture was stirred at 60° C. for 16 hours. The solvent was distilled off under reduced pressure and the obtained resiue was azeotroped with toluene and used for the synthesis of (d).

(d) Synthesis of 3-(3-cyano-5-cyclopropyl-4-methoxybenzoyl)-2,3-dihydro-1,3-benzothiazole 2,3-dihydro-1,3-benzothiazole synthesized from 2-aminobenzenethiol (346 mg) and 37% formalin (0.23 mL) in the same manner as in Example 1 was dissolved in chloroform (3 mL), and triethylamine (0.38 mL) and 3-cyano-5-cyclopropyl-4-methoxybenzoyl chloride were added to the solution, and then stirred at room temperature for 2 hours. The solvent was distilled off under reduced pressure and water was added, and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was used for the synthesis of (e).

(e) Synthesis of 3-(3-cyano-5-cyclopropyl-4-methoxybenzoyl)-1,1-dioxo-2,3-dihydro-1,3-benzothiazole 3-(3-cyano-5-cyclopropyl-4-methoxybenzoyl)-2,3-dihydro-1,3-benzothiazole was dissolved in chloroform (5 mL), and 70% metachloroperbenzoic acid (422 mg) was added to the solution, and then the mixture was stirred at room temperature for 16 hours and quenched with 10% sodium thiosulfate. The solvent was distilled off under reduced pressure and 1N sodium hydroxide was added, and then the mixture was extracted with ethyl acetate. The organic layer was washed with 1N sodium hydroxide and saturated brine, and then dried over anhydrous sodium sulfate. The solvent was distilled off under reduced pressure and the obtained residue was crystallized from n-hexane-ethyl acetate-methanol to obtain the title compound (147 mg) as a colorless crystal.

(f) Synthesis of 3-(3-cyano-5-cyclopropyl-4-hydroxybenzoyl)-1,1-dioxo-2,3-dihydro-1,3-benzothiazole 3-(3-cyano-5-cyclopropyl-4-methoxybenzoyl)-1,1-dioxo-2,3-dihydro-1,3-benzothiazole (142 mg) was dissolved in N,N-dimethylformamide (2 mL), and lithium chloride (163 mg) was added to the solution, and then the mixture was stirred at 100° C. for 23 hours. To the reaction solution, 1N hydrochloric acid was added, and then the mixture was extracted with ethyl acetate. The organic layer was washed with 1N hydrochloric acid and saturated brine, and then dried over anhydrous sodium sulfate. The solvent was distilled off under reduced pressure and the obtained residue was crystallized from n-hexane-ethyl acetate to obtain the title compound (115 mg) as a colorless crystal.

1H-NMRδ (DMSO-d6): 0.69-0.75 (2H, m), 0.94-1.01 (2H, m), 2.05-2.15 (1H, m), 5.30 (2H, s), 7.41 (1H, d, J=2.1 Hz), 7.43 (1H, dd, J=7.8, 7.8 Hz), 7.75 (1H, ddd, J=8.4, 7.8, 1.2 Hz), 7.84 (1H, d, J=2.1 Hz), 7.90 (1H, d, J=7.8 Hz), 8.02 (1H, d, J=8.4 Hz). MS (m/z): 353 (M-H)-.

Example 14

3-(3-cyano-5-ethynyl-4-hydroxybenzoyl)-1,1-dioxo-2,3-dihydro-1,3-benzothiazole

(a) Synthesis of 3-cyano-5-ethynyl-4-methoxybenzoic acid

Methyl 3-cyano-5-ethynyl-4-methoxybenzoate (640 mg) was dissolved in tetrahydrofuran (6 mL) and water (3 mL), and lithium hydroxide monohydrate (495 mg) was added to the solution, and then the mixture was stirred at room temperature for 3 hours. The solvent was distilled off under reduced pressure and 1N hydrochloric acid was added, and then the mixture was extracted with ethyl acetate. The organic layer was washed with saturated brine, and then dried over anhydrous sodium sulfate. The solvent was distilled off under reduced pressure to obtain the title compound (610 mg) as a brown crystal.

1H-NMRδ (DMSO-d6): 4.20 (3H, s), 4.72 (1H, s), 8.17 (1H, d, J=2.1 Hz), 8.24 (1H, d, J=2.1 Hz). MS (m/z): 200 (M-H)-.

(b) Synthesis of
3-cyano-5-ethynyl-4-methoxybenzoyl chloride

To 3-cyano-5-ethynyl-4-methoxybenzoic acid (610 mg), toluene (6 mL), N,N-dimethylformamide (1 droplet) and oxalyl chloride (0.32 mL) were added to the solution under ice cooling, and the mixture was stirred at room temperature for 1.5 hours. The solvent was distilled off under reduced pressure and the obtained residue was azeotroped with toluene and used for the synthesis of (c).

(c) Synthesis of 3-(3-cyano-5-ethynyl-4-methoxy-benzoyl)-2,3-dihydro-1,3-benzothiazole 2,3-dihydro-1,3-benzothiazole synthesized from 2-aminobenzenethiol (570 mg) and 37% formalin (0.38 mL) in the same manner as in Example 1 was dissolved in dichloromethane (10 mL), and triethylamine (1.2 mL) and 3-cyano-5-ethynyl-4-methoxybenzoyl chloride were added to the solution, and then the mixture was stirred at mom temperature for 2.5 hours. The solvent was distilled off under reduced pressure and water was added, and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was purified by silica gel column chromatography (n-hexane:ethyl acetate=5:1) to obtain the title compound (283 mg) as a yellow oily substance.

(d) Synthesis of 3-(3-cyano-5-ethynyl-4-methoxy-benzoyl)-1,1-dioxo-2,3-dihydro-1,3-benzothiazole 3-(3-cyano-5-ethynyl-4-methoxybenzoyl)-2,3-dihydro-1,3-benzothiazole (344 mg) was dissolved in dichloromethane (5 mL), and 70% metachloroperbenzoic acid (1.94 g) was added to the solution. After stirring the mixture at room temperature for 16 hours, 1N sodium hydroxide was added, and then the mixture was extracted with ethyl acetate. The organic layer was washed with 1N sodium hydroxide and saturated brine, and then dried over anhydrous sodium sulfate. The solvent was distilled off under reduced pressure to obtain the title compound (199 mg) as a yellow oily substance.

(e) Synthesis of 3-(3-cyano-5-ethynyl-4-hydroxyben-zoyl)-1,1-dioxo-2,3-dihydro-1,3-benzothiazole 3-(3-cyano-5-ethynyl-4-methoxybenzoyl)-1,1-dioxo-2,3-dihydro-1,3-benzothiazole (197 mg) was dissolved in N,N-dimethylformamide (2 mL), and lithium chloride (239 mg) was added to the solution, and then the mixture was stirred at 100° C. for 1 hour. To the reaction solution, 1N hydrochloric acid was added, and then the mixture was extracted with ethyl acetate. The organic layer was washed with 1N hydrochloric acid and saturated brine, and then dried over anhydrous sodium sulfate. The solvent was distilled off under reduced pressure and the obtained residue was purified by silica gel column chromatography (n-hexane:ethyl acetate=1:1), and then crystallized from n-hexane-acetone to obtain the title compound (102 mg) as a pale yellow crystal.
1H-NMRδ (DMSO-d6): 4.58 (1H, s), 5.35 (2H, s), 7.44 (1H, dd, J=7.6, 7.6 Hz), 7.76 (1H, dd, J=8.4, 7.6 Hz), 7.91 (1H, d, J=8.4 Hz), 7.93 (1H, d, J=2.4 Hz), 8.04 (1H, d, J=2.4 Hz), 8.05 (1H, d, J=7.6 Hz). MS (m/z): 337 (M-H)-.

Example 15

3-(3-cyano-4-hydroxy-5-methylsulfanylbenzoyl)-1,1-dioxo-2,3-dihydro-1,3-benzothiazole (a) Synthesis of methyl 3-bromo-4-hydroxybenzoate Methyl 4-hydroxybenzoate (25.00 g) was dissolved in chloroform (225 mL) and methanol (25 mL), and a chloroform (30 mL) solution of bromine (8.5 mL) was added dropwise to the solution, and then the mixture was stirred for 2 hours. The reaction solution was diluted with chloroform, washed with water, an aqueous 10% sodium thiosulfate solution and saturated brine and then dried over anhydrous sodium sulfate. The solvent was distilled off under reduced pressure to obtain the title compound (37.81 g) as a colorless crystal.

(b) Synthesis of methyl 3-cyano-4-hydroxybenzoate

Methyl 3-bromo-4-hydroxybenzoate (37.81 g) was dissolved in N,N-dimethylformamide (250 mL), and copper cyanide (22.03 g) was added to the solution. After stirring the mixture at 150° C. for 16 hours, potassium carbonate (68.00 g) and chloromethyl methyl ether (14.8 mL) were added to the solution under ice cooling, and then the mixture was stirred for 2 hours. The reaction solution was filtered and water was added, and then the reaction mixture was extracted with ethyl acetate. After the operation of adding water to the organic layer, stirring the mixture, filtering the mixture and separating the organic layer was repeated three times, the organic layer was washed with saturated brine and then dried over anhydrous sodium sulfate. The solvent was distilled off under reduced pressure and the obtained residue was dissolved in chloroform (30 mL). Trifluoroacetic acid (30 mL) was added to the solution, and then the mixture was stirred at room temperature for 2 hours. The solvent was distilled off under reduced pressure and the obtained residue was washed with a mixture of n-hexane and ethyl acetate in a mixing ratio of 2:1 to obtain the title compound (6.53 g) as a pale yellow crystal.

(c) Synthesis of methyl
3-cyano-4-hydroxy-5-iodobenzoate

Methyl 3-cyano-4-hydroxybenzoate (6.47 g) was dissolved in chloroform (80 mL) and methanol (10 mL), and N-iodosuccinimide (8.63 g) and trifluoromethanesulfonic acid (2.5 mL) were added to the solution, and then the mixture was stirred at room temperature for 1 hour. The solvent was distilled off under reduced pressure and the obtained residue was washed with water to obtain the title compound (11.29 g) as a pale yellow crystal.

(d) Synthesis of methyl
3-cyano-5-iodo-4-methoxybenzoate

Methyl 3-cyano-4-hydroxy-5-iodobenzoate (11.29 g) was dissolved in N,N-dimethylformamide (230 mL), and potassium carbonate (49.20 g) and dimethylsulfuric acid (17.0 mL) were added to the solution, and then the mixture was stirred at room temperature for 18 hours. After the reaction solution was filtered, water was added and the precipitated crystal was collected by filtration to obtain the title compound (8.99 g) as a pale yellow crystal.

(e) Synthesis of 3-cyano-5-iodo-4-methoxybenzoic acid

Methyl 3-cyano-5-iodo-4-methoxybenzoate (8.00 g) was dissolved in tetrahydrofuran (100 mL) and water (50 mL), and lithium hydroxide monohydrate (423 g) was added to the solution, and then the mixture was stirred at room temperature for 4 hours. The organic solvent was distilled off under reduced pressure and the aqueous layer was washed with n-hexane. The aqueous layer was acidified with 2N hydrochloric acid and then extracted with ethyl acetate. The organic layer was washed with saturated brine, and then dried over anhydrous sodium sulfate. The solvent was distilled off under reduced pressure to obtain the title compound (7.26 g) as a colorless crystal.

1H-NMRδ (DMSO-d6): 4.38 (3H, s), 8.58 (1H, d, J=2.0 Hz), 8.86 (1H, d, J=2.0 Hz), 13.89 (1H, brs). MS (m/z): 302 (M-1)-.

(f) Synthesis of 3-cyano-5-iodo-4-methoxybenzoyl chloride

To 3-cyano-5-iodo-4-methoxybenzoic acid (512 mg), toluene (5 mL), N,N-dimethylformamide (1 droplet) and thionyl chloride (0.15 mL) were added, and the mixture was stirred at 60° C. for 15 hours. The solvent was distilled off under reduced pressure and then azeotroped with toluene to obtain the title compound (527 mg) as a pale yellow solid.

(g) Synthesis of 3-(3-cyano-5-iodo-4-methoxybenzoyl)-2,3-dihydro-1,3-benzothiazole 2,3-dihydro-1,3-benzothiazole synthesized from 2-aminobenzenethiol (317 mg) and 37% formalin (0.21 mL) in the same manner as in Example 1 was dissolved in dichloromethane (6 mL), and triethylamine (0.70 mL) and 3-cyano-5-iodo-4-methoxybenzoyl chloride (527 mg) were added to the solution, and then the mixture was stirred at room temperature for 14 hours. The solvent was distilled off under reduced pressure and water was added, and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was purified by silica gel column chromatography (n-hexane:ethyl acetate=5:1) to obtain the title compound (435 mg) as a yellow oily substance.

(h) Synthesis of 3-(3-cyano-5-iodo-4-methoxybenzoyl)-1,1-dioxo-2,3-dihydro-1,3-benzothiazole 3-(3-cyano-5-iodo-4-methoxybenzoyl)-2,3-dihydro-1,3-benzothiazole (196 mg) was dissolved in dichloromethane (4 mL), and 70% metachloroperbenzoic acid (495 mg) was added to the solution. After stirring the mixture at room temperature for 2 hours, 1N sodium hydroxide was added, and then the mixture was extracted with ethyl acetate. The organic layer was washed with 1N sodium hydroxide and saturated brine, and then dried over anhydrous sodium sulfate. The solvent was distilled off under reduced pressure and then the obtained residue was purified by silica gel column chromatography (n-hexane:ethyl acetate=2:1) to obtain the title compound (106 mg) as a pale yellow oily substance.

(i) Synthesis of 3-(3-cyano-4-hydroxy-5-iodobenzoyl)-1,1-dioxo-2,3-dihydro-1,3-benzothiazole 3-(3-cyano-5-iodo-4-methoxybenzoyl)-1,1-dioxo-2,3-dihydro-1,3-benzothiazole (106 mg) was dissolved in N,N-dimethylformamide (1 mL), and lithium chloride (40 mg) was added to the solution, and then the mixture was stirred at 100° C. for 2 hours. To the reaction solution, 1N hydrochloric acid was added, and then the mixture was extracted with ethyl acetate. The organic layer was washed with 1N hydrochloric acid and saturated brine, and then dried over anhydrous sodium sulfate. The solvent was distilled off under reduced pressure to obtain the title compound (100 mg) as a yellow oily substance.

1H-NMRδ (DMSO-d6): 5.35 (2H, s), 7.43 (1H, dd, J=7.8, 7.3 Hz), 7.76 (1H, dd, J=8.4, 7.3 Hz), 7.90 (1H, d, J=7.8 Hz), 8.02 (1H, d, J=2.2 Hz), 8.04 (1H, d, J=8.4 Hz), 827 (1H, d, J=2.2 Hz).

(j) Synthesis of 3-(3-cyano-4-methoxy-5-methylsulfanylbenzoyl)-1,1-dioxo-2,3-dihydro-1,3-benzothiazole 3-(3-cyano-4-hydroxy-5-iodobenzoyl)-1,1-dioxo-2,3-dihydro-1,3-benzothiazole (334 mg) was dissolved in N,N-dimethylformamide (3.5 mL), and 2,2'-bipyridine (11 mg), zinc powder (95 mg), nickel bromide (16 mg) and dimethyl disulfide (0.04 mL) were added to the solution, and then the mixture was stirred at 80° C. for 1 hour. After the reaction solution was filtered, 1N hydrochloric acid was added and the reaction mixture was extracted with ethyl acetate. The organic layer was washed with saturated brine, and then dried over anhydrous sodium sulfate. The solvent was distilled off under reduced pressure and the obtained residue was dissolved in N,N-dimethylformamide (3 mL). Potassium carbonate (298 mg) and dimethylsulfuric acid (0.13 mL) was added to the solution, and then the mixture was stirred at room temperature for 1 hour. Water was added to the reaction solution, and then the reaction mixture was extracted with ethyl acetate. The organic layer was washed with water and saturated brine, and then dried over anhydrous sodium sulfate. The solvent was distilled off under reduced pressure and the obtained residue was purified by silica gel column chromatography (n-hexane:ethyl acetate=2:1) to obtain the title compound (142 mg) as a pale yellow oily substance.

(k) Synthesis of 3-(3-cyano-4-hydroxy-5-methylsulfanylbenzoyl)-1,1-dioxo-2,3-dihydro-1,3-benzothiazole 3-(3-cyano-4-methoxy-5-methylsulfanylbenzoyl)-1,1-dioxo-2,3-dihydro-1,3-benzothiazole (142 mg) was dissolved in N,N-dimethylformamide (1 mL), and lithium chloride (64 mg) was added to the solution, and then the mixture was stirred at 100° C. for 1.5 hours. To the reaction solution, 1N hydrochloric acid was added, and then the mixture was extracted with ethyl acetate. The organic layer was washed with 1N hydrochloric acid and saturated brine, and then dried over anhydrous sodium sulfate. The solvent was distilled off under reduced pressure and the obtained residue was crystallized from n-hexane-chloroform to obtain the title compound (95 mg) as a yellow crystal.

1H-NMRδ (DMSO-d6): 2.46 (3H, s), 5.34 (2H, s), 7.45 (1H, dd, J=7.6, 7.3 Hz), 7.68 (1H, d, J=2.2 Hz), 7.77 (1H, dd, J=8.4, 7.6 Hz), 7.82 (1H, d, J=2.2 Hz), 7.91 (1H, d, J=7.3 Hz), 8.08 (1H, d, J=8.4 Hz). MS (m/z): 359 (M-H)-.

Example 16

3-(3-cyano-4-hydroxy-5-methylsulfonylbenzoyl)-1,1-dioxo-2,3-dihydro-1,3-benzothiazole (a) Synthesis of 3-(3-cyano-4-methoxy-5-methylsulfonylbenzoyl)-1,1-dioxo-2,3-dihydro-1,3-benzothiazole 3-(3-cyano-4-methoxy-5-methylsulfanylbenzoyl)-1,1-dioxo-2,3-dihydro-1,3-benzothiazole (163 mg) was dissolved in dichloromethane (4 mL), and 70% metachloroperbenzoic acid (480 mg) was added to the solution. After stirring the mixture at room temperature for 18 hours, 1N sodium hydroxide was added to the solution and then the mixture was extracted with ethyl acetate. The organic layer was washed with 1N sodium hydroxide and saturated brine, and then dried over anhydrous sodium sulfate. The solvent was distilled off under reduced pressure to obtain the title compound (142 mg) as a pale yellow solid.

(b) Synthesis of 3-(3-cyano-4-hydroxy-5-methylsulfonylbenzoyl)-1,1-dioxo-2,3-dihydro-1,3-benzothiazole 3-(3-cyano-4-methoxy-5-methylsulfonylbenzoyl)-1,1-dioxo-2,3-dihydro-1,3-benzothiazole (138 mg) was dissolved in N,N-dimethylformamide (1 mL), and lithium chloride (58 mg) was added to the solution, and then the mixture was stirred at 70° C. for 3 hours. To the reaction solution, 1N hydrochloric acid was added, and then the mixture was extracted with ethyl acetate. The organic layer was washed with 1N hydrochloric acid and saturated brine, and then dried over anhydrous sodium sulfate. The solvent was distilled off under reduced pressure and the obtained residue was crystallized from n-hexane-chloroform to obtain the title compound (69 mg) as a brown crystal.

1H-NMRδ (DMSO-d6): 3.26 (3H, s), 5.36 (2H, s), 7.40 (1H, dd, J=7.6 Hz, 7.6 Hz), 7.73 (1H, dd, J=8.1, 7.6 Hz), 7.88 (1H, d, J=8.1 Hz), 7.92 (1H, d, J=7.6 Hz), 8.11 (2H, s). MS (m/z): 391 (M-H)-.

Example 17

3-(3-cyano-4-hydroxy-5-methylsulfonylbenzoyl)-1,1-dioxo-2,3-dihydro-1,3-benzothiazole 3-(3-cyano-4-hydroxy-5-methylsulfanylbenzoyl)-1,1-dioxo-2,3-dihydro-1,3-benzothiazole (7 mg) was dissolved in tetrahydrofuran (0.5 mL) and water (0.5 mL), and oxone (6 mg) was added to the solution, and then the mixture was stirred at room temperature for 1 hour. To the reaction solution, 1N hydrochloric acid was added, and then the mixture was extracted with ethyl acetate. The organic layer was washed with water and saturated brine, and then dried over anhydrous sodium sulfate. The solvent was distilled off under reduced pressure and the obtained residue was crystallized from n-hexane-chloroform to obtain the title compound (6 mg) as a pale yellow crystal.

1H-NMRδ (CDCl3): 2.88 (3H, s), 4.96 (2H, s), 7.33 (1H, dd, J=7.6, 7.4 Hz), 7.57 (1H, dd, J=8.0, 7.4 Hz), 7.67 (1H, d, J=8.0 Hz), 7.72 (1H, d, J=7.6 Hz), 7.89 (1H, s), 7.94 (1H, s). MS (m/z): 375 (M-H)-.

Example 18

3-(3-chloro-4-hydroxy-5-trifluoromethylbenzoyl)-1,1-dioxo-2,3-dihydro-1,3-benzothiazole (a) Synthesis of methyl 3-chloro-4-hydroxy-5-trifluoromethyl benzoate Methyl 4-hydroxy-3-trifluoromethyl benzoate (1.40 g) was dissolved in chloroform (14 mL) and methanol (3 mL), and N-chlorosuccinimide (1.70 g) and trifluoromethanesulfonic acid (40 μL) were added to the solution, and then the mixture was stirred at room temperature for 16 hours. The solvent was distilled off under reduced pressure and 10% sodium thiosulfate was added, and then the mixture was extracted with ethyl acetate. The organic layer was washed with water and saturated brine, and then dried over anhydrous sodium sulfate. The solvent was distilled off under reduced pressure to obtain the title compound (1.26 g) as a brown solid.

(b) Synthesis of methyl 3-chloro-4-methoxy-5-trifluoromethyl benzoate

Methyl 3-chloro-4-hydroxy-5-trifluoromethyl benzoate (1.26 g) was dissolved in N,N-dimethylformamide (6 mL), and potassium carbonate (3.42 g) and dimethylsulfuric acid (1.40 mL) were added to the solution, and then the mixture was stirred at room temperature for 2 hours. Water was added to the reaction solution, and then the reaction mixture was extracted with ethyl acetate. The organic layer was washed with saturated brine, and then dried over anhydrous sodium sulfate. The solvent was distilled off under reduced pressure and the obtained residue was purified by silica gel column chromatography (n-hexane:ethyl acetate=6:1) to obtain the title compound (639 mg) as a colorless oily substance.

(c) Synthesis of 3-chloro-4-methoxy-5-trifluoromethylbenzoic acid

Methyl 3-chloro-4-methoxy-5-trifluoromethyl benzoate (634 mg) was dissolved in tetrahydrofuran (4 mL) and water (4 mL), and lithium hydroxide monohydrate (396 mg) was added to the solution, and then the mixture was stirred at room temperature for 2 hours. The organic solvent was distilled off under reduced pressure and then the aqueous layer was washed with n-hexane. The aqueous layer was acidified with 1N hydrochloric acid and then extracted with ethyl acetate. The organic layer was washed with saturated brine, and then dried over anhydrous sodium sulfate. The solvent was distilled off under reduced pressure to obtain the title compound (579 mg) as a colorless crystal.

1H-NMRδ (DMSO-d6): 3.97 (3H, s), 8.08 (1H, d, J=2.1 Hz), 8.26 (1H, d, J=2.1 Hz), 13.69 (1H, br). MS (m/z): 253 (M-H)-, 255 (M+2-H)-.

(d) Synthesis of 3-chloro-4-methoxy-5-trifluoromethylbenzoyl chloride

To 3-chloro-4-methoxy-5-trifluoromethylbenzoic acid (300 mg), toluene (3 mL), N,N-dimethylformamide (1 droplet) and thionyl chloride (0.13 mL) were added, and the mixture was stirred at 60° C. for 16 hours. The solvent was distilled off under reduced pressure and the obtained residue was azeotroped with toluene and used for the synthesis of (e).

(e) Synthesis of 3-(3-chloro-4-methoxy-5-trifluoromethylbenzoyl)-2,3-dihydro-1,3-benzothiazole 2,3-dihydro-1,3-benzothiazole synthesized from 2-aminobenzenethiol (442 mg) and 37% formalin (0.29 mL) in the same manner as in Example 1 was dissolved in chloroform (8 mL), and triethylamine (0.49 mL) and 3-chloro-4-methoxy-5-trifluoromethylbenzoyl chloride were added to the solution, and then the mixture was stirred at room temperature for 1 hour. The solvent was distilled off under reduced pressure and water was added, and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was used for the synthesis of (f).

(f) Synthesis of 3-(3-chloro-4-methoxy-5-trifluoromethylbenzoyl)-1,1-dioxo-2,3-dihydro-1,3-benzothiazole 3-(3-chloro-4-methoxy-5-trifluoromethylbenzoyl)-2,3-dthydro-1,3-benzothiazole was dissolved in chloroform (5 mL), and 70% metachloroperbenzoic acid (726 mg) was added to the solution, and then the mixture was stirred at room temperature for 18 hours and quenched with 10% sodium thiosulfate. The solvent was distilled off under reduced pressure and 1N sodium hydroxide was added, and then the mixture was extracted with ethyl acetate. The organic layer was washed with 1N sodium hydroxide and saturated brine, and then dried over anhydrous sodium sulfate. The solvent was distilled off under reduced pressure and the obtained residue was purified by silica gel column chromatography (n-hexane:ethyl acetate=3:1) to obtain the title compound (74 mg) as a colorless crystal.

(g) Synthesis of 3-(3-chloro-4-hydroxy-5-trifluoromethylbenzoyl)-1,1-dioxo-2,3-dihydro-1,3-benzothiazole 3-(3-chloro-4-methoxy-5-trifluoromethylbenzoyl)-1,1-dioxo-2,3-dihydro-1,3-benzothiazole (74 mg) was dissolved in N,N-dimethylformamide (2 mL), lithium chloride (77 mg) was added to the solution, and then the mixture was stirred at 70° C. for 22 hours. To the reaction solution, 1N hydrochloric acid was added, and then the mixture was extracted with ethyl acetate. The organic layer was washed with 1N hydrochloric acid and saturated brine, and then dried over anhydrous sodium sulfate. The solvent was distilled off under reduced pressure and the obtained residue was crystallized from diethylether to obtain the title compound (65 mg) as a colorless crystal.

1H-NMRδ (DMSO-d6): 5.36 (2H, s), 7.44 (1H, ddd, J=7.8, 7.8, 0.8 Hz), 7.77 (1H, ddd, J=8.2, 7.8, 1.3 Hz), 7.86 (1H, d, J=2.1 Hz), 7.91 (1H, dd, J=7.8, 0.8 Hz), 8.06 (1H, d, J=2.1 Hz), 8.07 (1H, d, J=8.2 Hz). MS (m/z): 390 (M-H)-.

Example 19

3-(3-chloro-5-fluoro-4-hydroxybenzoyl)-1,1-dioxo-2,3-dihydro-1,3-benzothiazole (a) Synthesis of 3-chloro-5-fluoro-4-methoxybenzoyl chloride To 3-chloro-5-fluoro-4-methoxybenzoic acid (295 mg), toluene (3 mL), N,N-dimethylformamide (1 droplet) and thionyl chloride (0.15 mL) were added, and then the mixture was stirred at 60° C. for 16 hours. The solvent was distilled off under reduced pressure and the obtained residue was azeotroped with toluene and used for the synthesis of (b).

(b) Synthesis of 3-(3-chloro-5-fluoro-4-methoxybenzoyl)-2,3-dihydro-1,3-benzothiazole 2,3-dihydro-1,3-benzothiazole synthesized from 2-aminobenzenethiol (346 mg) and 37% formalin (0.23 mL) in the same manner as in Example 1 was dissolved in chloroform (3 mL), and triethylamine (0.38 mL) and 3-chloro-5-fluoro-4-methoxybenzoyl chloride were added to the solution, and then the mixture was stirred at room temperature for 90 minutes. The solvent was distilled off under reduced pressure and water was added, and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was purified by silica gel column chromatography (n-hexane:ethyl acetate=8:1) to obtain the title compound (356 mg) as a pale yellow oily substance.

(c) Synthesis of 3-(3-chloro-5-fluoro-4-methoxybenzoyl)-1,1-dioxo-2,3-dihydro-1,3-benzothiazole 3-(3-chloro-5-fluoro-4-methoxybenzoyl)-2,3-dihydro-1,3-benzothiazole (348 mg) was dissolved in chloroform (7 mL), and 70% metachloroperbenzoic acid (739 mg) was added to the solution, and then the mixture was stirred at room temperature for 16 hours and quenched with 10% sodium thio sulfate. The solvent was distilled off under reduced pressure and 1N sodium hydroxide was added, and then the mixture was extracted with ethyl acetate. The organic layer was washed with 1N sodium hydroxide and saturated brine, and then dried over anhydrous sodium sulfate. The solvent was distilled off under reduced pressure to obtain the title compound (313 mg) as a colorless crystal.

(d) Synthesis of 3-(3-chloro-5-fluoro-4-hydroxybenzoyl)-1,1-dioxo-2,3-dihydro-1,3-benzothiazole 3-(3-chloro-5-fluoro-4-methoxybenzoyl)-1,1-dioxo-2,3-dihydro-1,3-benzothiazole (307 mg) was dissolved in N,N-dimethylformamide (6 mL), and lithium chloride (163 mg) was added to the solution, and then the mixture was stirred at 100° C. for 16 hours. To the reaction solution, 1N hydrochloric acid was added, and then the mixture was extracted with ethyl acetate. The organic layer was washed with 1N hydrochloric acid and saturated brine, and then dried over anhydrous sodium sulfate. The solvent was distilled off under reduced pressure and the obtained residue was purified by silica gel column chromatography (n-hexane:ethyl acetate=1:1) to obtain the title compound (296 mg) as a pale yellow amorphous product.

1H-NMRδ (DMSO-d6): 5.35 (2H, s), 7.43 (1H, dd, J=7.4, 7.4 Hz), 3.59 (1H, dd, J=11.1, 1.8 Hz), 7.61 (1H, s), 7.76 (1H, ddd, J=8.4, 7.4, 1.2 Hz), 7.90 (1H, d, J=7.4 Hz), 8.02 (1H, d, J=8.4 Hz), 11.35 (1H, brs). MS (m/z): 340 (M-H)-, 342 (M+2-H)-.

Example 20

3-(3,5-difluoro-4-hydroxybenzoyl)-1,1-dioxo-2,3-dihydro-1,3-benzothiazole (a) Synthesis of 3,5-difluoro-4-methoxybenzoyl chloride To 3,5-difluoro-4-methoxybenzoic acid (310 mg), toluene (3 mL), N,N-dimethylformamide (1 droplet) and thionyl chloride (0.14 mL) were added to the solution, and then the mixture was stirred at 60° C. for 16 hours. The solvent was distilled off under reduced pressure and then azeotroped with toluene to obtain the title compound (347 mg) as a brown oily substance.

(b) Synthesis of 3-(3,5-difluoro-4-methoxybenzoyl)-2,3-dihydro-1,3-benzothiazole 2,3-dihydro-1,3-benzothiazole synthesized from 2-aminobenzenethiol (316 mg) and 37% formalin (0.21 mL) in the same manner as in Example 1 was dissolved in dichloromethane (3 mL), and diisopropylethylamine (0.56 mL) and 3,5-difluoro-4-methoxybenzoyl chloride (347 mg) were added to the solution, and then the mixture was stirred at room temperature for 1 hour. The solvent was distilled off under reduced pressure and water was added, and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was used for the synthesis of (c).

(c) Synthesis of 3-(3,5-difluoro-4-methoxybenzoyl)-2,3-dihydro-1,1-dioxo-1,3-benzothiazole 3-(3,5-difluoro-4-methoxybenzoyl)-2,3-dihydro-1,3-benzothiazole was dissolved in dichloromethane (8 mL), and 70% metachloroperbenzoic acid (2.01 g) was added to the solution. After stirring the mixture at room temperature for 5 hours, 1N sodium hydroxide was added and the mixture was extracted with ethyl acetate. The organic layer was washed with 1N sodium hydroxide and saturated brine, and then dried over anhydrous sodium sulfate. The solvent was distilled off under reduced pressure to obtain the title compound (453 mg) as a colorless solid.

(d) Synthesis of 3-(3,5-difluoro-4-hydroxybenzoyl)-1,1-dioxo-2,3-dihydro-1,3-benzothiazole 3-(3,5-difluoro-4-methoxybenzoyl)-1,1-dioxo-2,3-dihydro-1,3-benzothiazole (453 mg) was dissolved in N,N-dimethylformamide (4 mL), and lithium chloride (559 mg) was added to the solution, and then the mixture was stirred at 100° C. for 16 hours. To the reaction solution, 1N hydrochloric acid was added, and then the mixture was extracted with ethyl acetate. The organic layer was washed with water and saturated brine, and then dried over anhydrous sodium sulfate. The solvent was distilled off under reduced pressure and the obtained residue was purified by silica gel column chromatography (n-hexane:ethyl acetate=1:1) and then crystallized from diethyl ether to obtain the title compound (270 mg) as a colorless crystal.

1H-NMRδ (CD3OD): 5.14 (2H, s), 7.32 (2H, d, J=8.3 Hz), 7.40 (1H, dd, J=7.8, 7.3 Hz), 7.66 (1H, dd, J=8.4, 7.3 Hz), 7.77 (1H, d, J=7.8 Hz), 7.83 (1H, d, J=8.4 Hz). MS (m/z): 324 (M-H)-.

Example 21

3-(3-chloro-4-hydroxy-5-methylsulfanylbenzoyl)-1,1-dioxo-2,3-dihydro-1,3-benzothiazole (a) Synthesis of methyl 3-chloro-4-hydroxy-5-iodobenzoate Methyl 3-chloro-4-hydroxybenzoate (12.31 g) was dissolved in dichloromethane (100 mL) and methanol (12 mL), and N-iodosuccinimide (15.59 g) and trifluoromethanesulfonic acid (2 mL) were added to the solution, and then the mixture was stirred at room temperature for 2 hours. The solvent was distilled off under reduced pressure and the obtained residue was'washed with water (100 mL) to obtain the title compound (20.52 g) as a colorless crystal.

(b) Synthesis of methyl 3-chloro-5-iodo-4-methoxybenzoate

Methyl 3-chloro-4-hydroxy-5-iodobenzoate (3.00 g) was dissolved in N,N-dimethylformamide (20 mL), and potassium carbonate (3.98 g) and dimethylsulfuric acid (1.82 mL) were added to the solution, and then the mixture was stirred at room temperature for 5 hours. The reaction solution was filtered and water was added, and then the reaction mixture was extracted with ethyl acetate. The organic layer was washed with water and saturated brine, and then dried over anhydrous sodium sulfate. The solvent was distilled off under reduced pressure to obtain the title compound (2.96 g) as a pale yellow crystal.

(c) Synthesis of 3-chloro-5-iodo-4-methoxybenzoic acid

Methyl 3-chloro-5-iodo-4-methoxybenzoate (2.96 g) was dissolved in tetrahydrofuran (23 mL) and water (7 mL), and lithium hydroxide monohydrate (1.52 g) was added to the solution, and then the mixture was stirred at room temperature for 19 hours. After the organic solvent was distilled off, the mixture was acidified with 1N hydrochloric acid and extracted with ethyl acetate. The organic layer was washed with saturated brine, and then dried over anhydrous sodium sulfate. The solvent was distilled off under reduced pressure to obtain the title compound (2.74 g) as a colorless crystal.

1H-NMRδ (CDCl3): 3.95 (3H, s), 8.11 (1H, dd, J=2.2 Hz, 0.5 Hz), 8.42 (1H, dd, J=2.2 Hz, 0.5 Hz). MS (m/z): 311 (M-H)-.

(d) Synthesis of 3-chloro-5-iodo-4-methoxybenzoyl chloride

To 3-chloro-5-iodo-4-methoxybenzoic acid (2.74 g), toluene (27 mL), N,N-dimethylformamide (1 droplet) and thionyl chloride (0.76 mL) were added to the solution, and then the mixture was stirred at 60° C. for 15 hours. The solvent was distilled off under reduced pressure and then azeotroped with toluene to obtain the title compound (3.05 g) as a yellow solid.

(e) Synthesis of 3-(3-chloro-5-iodo-4-methoxybenzoyl)-2,3-dihydro-1,3-benzothiazole 2,3-dihydro-1,3-benzothiazole synthesized from 2-aminobenzenethiol (1.65 g) and 37% formalin (1.09 mL) in the same manner as in Example 1 was dissolved in dichloromethane (15 mL), and diisopropylethylamine (3.0 mL) and 3-chloro-5-iodo-4-methoxybenzoyl chloride (3.05 g) were added to the solution, and then the mixture was stirred at room temperature for 1 hour. The solvent was distilled off under reduced pressure and water was added, and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was crystallized from a mixture of n-hexane and ethyl acetate in a mixing ratio of 1:1 to obtain the title compound (2.44 g) as a pale yellow solid.

(f) Synthesis of 3-(3-chloro-5-iodo-4-methoxybenzoyl)-1,1-dioxo-2,3-dihydro-1,3-benzothiazole 3-(3-chloro-5-iodo-4-methoxybenzoyl)-2,3-dihydro-1,3-benzothiazole (200 mg) was dissolved in tetrahydrofuran (5 mL), and 70% metachloroperbenzoic acid (462 mg) was added to the solution. After stirring the mixture at room temperature for 1.5 hours, 1N sodium hydroxide was added and then the mixture was extracted with ethyl acetate. The organic layer was washed with 1N sodium hydroxide and saturated brine, and then dried over anhydrous sodium sulfate. The solvent was distilled off under reduced pressure to obtain the title compound (96 mg) as a colorless oily substance.

(g) Synthesis of 3-(3-chloro-4-hydroxy-5-iodobenzoyl)-1,1-dioxo-2,3-dihydro-1,3-benzothiazole 3-(3-chloro-5-iodo-4-methoxybenzoyl)-1,1-dioxo-2,3-dihydro-1,3-benzothiazole (922 mg) was dissolved in N,N-dimethylformamide (6 mL), and lithium chloride (421 mg) was added to the solution, and then the mixture was stirred at 120° C. for 2.5 hours. To the reaction solution, 1N hydrochloric acid was added, and then the mixture was extracted with ethyl acetate. The organic layer was washed with 1N hydrochloric acid and saturated brine, and then dried over anhydrous sodium sulfate. The solvent was distilled off under reduced pressure to obtain the title compound (1.19 g) as a brown oily substance.

1H-NMRδ (CDCl3): 4.98 (2H, s), 7.30-7.92 (6H, m).

(h) Synthesis of 3-(3-chloro-4-methoxy-5-methylsulfanylbenzoyl)-1,1-dioxo-2,3-dihydro-1,3-benzothiazole 3-(3-chloro-4-hydroxy-5-iodobenzoyl)-1,1-dioxo-2,3-dihydro-1,3-benzothiazole (1.19 g) was dissolved in N,N-dimethylformamide (9 mL), and 2,2'-bipyridine (32 mg), a zinc powder (262 mg), nickel bromide (45 mg) and dimethyl disulfide (0.09 mL) were added to the solution, and then the mixture was stirred at 80° C. for 1.5 hours. After the reaction solution was filtered, 1N hydrochloric acid was added and the reaction mixture was extracted with ethyl acetate. The organic layer was washed with saturated brine, and then dried over anhydrous sodium sulfate. The solvent was distilled off under reduced pressure and the obtained residue was dissolved in N,N-dimethylformamide (6 mL). Potassium carbonate (828 mg) and dimethylsulfuric acid (0.38 mL) was added to the solution, and then the mixture was stirred at room temperature for 14 hours. Water was added to the reaction solution, and then the reaction mixture was extracted with ethyl acetate. The organic layer was washed with saturated brine, and then dried over anhydrous sodium sulfate. The solvent was distilled off under reduced pressure and the obtained residue was purified by silica gel column chromatography (n-hexane:ethyl acetate=3:1) to obtain the title compound (203 mg) as a yellow crystal.

(i) Synthesis of 3-(3-chloro-4-hydroxy-5-methylsulfanylbenzoyl)-1,1-dioxo-2,3-dihydro-1,3-benzothiazole 3-(3-chloro-4-methoxy-5-methylsulfanylbenzoyl)-1,1-dioxo-2,3-dihydro-1,3-benzothiazole (203 mg) was dissolved in N,N-dimethylformamide (2 mL), and lithium chloride (258 mg) was added to the solution, and then the mixture was stirred at 120° C. for 20 hours. To the reaction solution, 1N hydrochloric acid was added, and then the mixture was extracted with ethyl acetate. The organic layer was washed with 1N hydrochloric acid and saturated brine, and then dried over anhydrous sodium sulfate. The solvent was distilled off under reduced pressure and the obtained residue was crystallized from n-hexane-diethylether to obtain the title compound (169 mg) as a brown crystal.

1H-NMRδ (DMSO-d6): 2.44 (3H, s), 5.34 (2H, s), 7.38 (1H, s), 7.43 (1H, dd, J=7.8, 7.6 Hz), 7.54 (1H, s), 7.76 (1H, dd, J=8.6, 7.8 Hz), 7.90 (1H, d, J=7.6 Hz), 8.02 (1H, d, J=8.6 Hz), 10.54 (1H, s). MS (m/z): 368 (M-H)-.

Example 22

3-(3-chloro-4-hydroxy-5-methylsulfonylbenzoyl)-1,1-dioxo-2,3-dihydro-1,3-benzothiazole

(a) Synthesis of 3-(3-chloro-4-methoxy-5-methylsulfonylbenzoyl)-1,1-dioxo-2,3-dihydro-1,3-benzothiazole 3-(3-chloro-4-methoxy-5-methylsulfanylbenzoyl)-1,1-dioxo-2,3-dihydro-1,3-benzothiazole (828 mg) was dissolved in dichloromethane (10 mL), and 70% metachloroperbenzoic acid (2.13 g) was added to the solution, and then the mixture was stirred at room temperature for 16 hours. 1N sodium hydroxide was added and the precipitated crystal was washed with 1N sodium hydroxide, water and methanol to obtain the title compound (589 mg) as a colorless solid.

(b) Synthesis of 3-(3-chloro-4-hydroxy-5-methylsulfonylbenzoyl)-1,1-dioxo-2,3-dihydro-1,3-benzothiazole 3-(3-chloro-4-methoxy-5-methylsulfonylbenzoyl)-1,1-dioxo-2,3-dihydro-1,3-benzothiazole (586 mg) was dissolved in N,N-dimethylformamide (4 mL), and lithium chloride (241 mg) was added to the solution, and then the mixture was stirred at 120° C. for 2 hours. To the reaction solution, 1N hydrochloric acid was added, and the precipitated crystal was washed with water and then crystallized from n-hexane-chloroform to obtain the title compound (310 mg) as a colorless crystal.

1H-NMRδ (DMSO-d6): 3.34 (3H, s), 5.35 (2H, s), 7.44 (1H, dd, J=7.6, 7.3 Hz), 7.76 (1H, dd, J=8.4, 7.3 Hz), 7.91 (1H, d, J=7.6 Hz), 7.99 (1H, d, J=2.2 Hz), 8.03 (1H, d, J=8.4 Hz), 8.09 (1H, d, J=2.2 Hz). MS (m/z): 400 (M-H)-.

Example 23

3-(3-chloro-4-hydroxy-5-methylsulfinylbenzoyl)-1,1-dioxo-2,3-dihydro-1,3-benzothiazole 3-(3-chloro-4-hydroxy-5-methylsulfanylbenzoyl)-1,1-dioxo-2,3-dihydro-1,3-benzothiazole (51 mg) was dissolved in tetrahydrofuran (0.5 mL) and water (0.5 mL), and oxone (43 mg) was added to the solution, and then the mixture was stirred at room temperature for 1 hour. To the reaction solution, 1N hydrochloric acid was added, and then the mixture was extracted with ethyl acetate. The organic layer was washed with water and saturated brine, and then dried over anhydrous sodium sulfate. The solvent was distilled off under reduced pressure and the obtained residue was crystallized from n-hexane-diethylether to obtain the title compound (45 mg) as a brown crystal.

1H-NMRδ (DMSO-d6): 2.82 (3H, s), 5.35 (2H, s), 7.43 (1H, dd, J=7.6, 7.3 Hz), 7.75 (1H, dd, J=7.8, 7.6 Hz), 7.81 (1H, d, J=1.6 Hz), 7.86-8.02 (2H, m), 7.93 (1H, d, J=1.6 Hz). MS (m/z): 384 (M-H)-.

Example 24

3-(4-hydroxy-3-methylsulfonyl-5-trifluoromethyl-benzoyl)-1,1-dioxo-2,3-dihydro-1,3-benzothiazole

(a) Synthesis of methyl 4-hydroxy-3-iodo-5-trifluoromethyl benzoate

Methyl 4-hydroxy-3-trifluoromethyl benzoate (916 mg) was dissolved in dichloromethane (15 mL), and N-iodosuccinimide (1.06 g) and trifluoroacetic acid (5 mL) were added to the solution, and then the mixture was stirred at room temperature for 1 hour. After the solvent was distilled off under reduced pressure, 10% sodium thiosulfate was added and the mixture was extracted with ethyl acetate. The organic layer was washed with water and saturated brine, and then dried over anhydrous sodium sulfate. The solvent was distilled off under reduced pressure to obtain the title compound (1.44 g) as a brown solid.

(b) Synthesis of methyl 4-hydroxy-3-methylsulfanyl-5-trifluoromethyl benzoate Methyl 4-hydroxy-3-iodo-5-trifluoromethyl benzoate (126 g) was dissolved in N,N-dimethylformamide (12 mL), and 2,2'-bipyridine (57 mg), zinc powder (476 mg), nickel bromide (80 mg) and dimethyl disulfide (172 mg) were added to the solution, and then the mixture was stirred at 130° C. for 1 hour. After the reaction solution was filtered, 1N hydrochloric acid was added and the reaction mixture was extracted with ethyl acetate. The organic layer was washed with saturated brine, and then dried over anhydrous sodium sulfate. The solvent was distilled off under reduced pressure and the obtained residue was purified by silica gel column chromatography (n-hexane:ethyl acetate=4:1) to obtain the title compound (276 mg) as a colorless crystal.

(c) Synthesis of methyl 4-methoxy-3-methylsulfanyl-5-trifluoromethyl benzoate Methyl 4-hydroxy-3-methylsulfanyl-5-trifluoromethyl benzoate (327 mg) was dissolved in N,N-dimethylformamide (6 mL), and potassium carbonate (1.70 g) and dimethylsulfuric acid (0.35 mL) were added to the solution, and then the mixture was stirred at room temperature for 1 hour. After the reaction solution was filtered, 1N hydrochloric acid was added and the reaction mixture was extracted with ethyl acetate. The organic layer was washed with saturated brine, and then dried over anhydrous sodium sulfate. The solvent was distilled off under reduced pressure to obtain the title compound (344 mg) as a colorless oily substance.

(d) Synthesis of 4-methoxy-3-methylsulfanyl-5-trifluoromethylbenzoic acid

Methyl 4-methoxy-3-methylsulfanyl-5-trifluoromethyl benzoate (303 mg) was dissolved in tetrahydrofuran (3 mL) and water (1.5 mL), and lithium hydroxide monohydrate (215 mg) was added to the solution, and then the mixture was stirred at room temperature for 1 hour. After the organic solvent was distilled off, the aqueous layer was acidified with 1N hydrochloric acid and extracted with ethyl acetate. The organic layer was washed with saturated brine, dried over anhydrous sodium sulfate and then concentrated under reduced pressure to obtain the title compound (277 mg) as a colorless crystal.

1H-NMRδ (DMSO-d6): 2.56 (3H, s), 3.89 (3H, s), 7.90 (1H, d, J=1.7 Hz), 8.00 (1H, d, J=1.7 Hz), 13.49 (1H, brs). MS (m/z): 265 (M-H)-.

(e) Synthesis of 4-methoxy-3-methylsulfanyl-5-trifluoromethylbenzoyl chloride To 4-methoxy-3-methylsulfanyl-5-trifluoromethylbenzoic acid (277 mg), toluene (7 mL), N,N-dimethylformamide (1 droplet) and thionyl chloride (0.12 mL) were added, and then the mixture was stirred at 60° C. for 16 hours. The solvent was distilled off under reduced pressure and the obtained residue was azeotroped with toluene and used for the synthesis of (f).

(f) Synthesis of 3-(4-methoxy-3-methylsulfanyl-5-trifluoromethylbenzoyl)-2,3-dihydro-1,3-benzothiazole 2,3-dihydro-1,3-benzothiazole synthesized from 2-aminobenzenethiol (346 mg) and 37% formalin (0.23 mL) in the same manner as in Example 1 was dissolved in chloroform (4 mL), and triethylamine (0.43 mL) and 4-methoxy-3-methylsulfanyl-5-trifluoromethylbenzoyl chloride were added to the solution, and then the mixture was stirred at room temperature for 1 hour. After the solvent was distilled off under reduced pressure, water was added and the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was used for the synthesis of (g).

(g) Synthesis of 3-(4-methoxy-3-methylsulfonyl-5-trifluoromethylbenzoyl)-1,1-dioxo-2,3-dihydro-1,3-benzothiazole 3-(4-methoxy-3-methylsulfanyl-5-trifluoromethylbenzoyl)-2,3-dihydro-1,3-benzothiazole synthesized in (f) was dissolved in chloroform (8 mL), and 70% metachloroperbenzoic acid (1.34 g) was added to the solution, and then the mixture was stirred at room temperature for 20 hours and quenched with 10% sodium thiosulfate. After the solvent was distilled off under reduced pressure, 1N sodium hydroxide was added and the mixture was extracted with ethyl acetate. The organic layer was washed with 1N sodium hydroxide and saturated brine, and then dried over anhydrous sodium sulfate. The solvent was distilled off under reduced pressure and the obtained residue was purified by silica gel column chromatography (n-hexane:ethyl acetate=2:1) to obtain the title compound (310 mg) as a colorless crystal.

(h) Synthesis of 3-(4-hydroxy-3-methylsulfonyl-5-trifluoromethylbenzoyl)-1,1-dioxo-2,3-dihydro-1,3-benzothiazole 3-(4-methoxy-3-methylsulfonyl-5-trifluoromethylbenzoyl)-1,1-dioxo-2,3-dihydro-1,3-benzothiazole (305 mg) was dissolved in N,N-dimethylformamide (3 mL), and lithium chloride (288 mg) was added to the solution, and then the mixture was stirred at 70° C. for 1 hour. To the reaction solution, 1N hydrochloric acid was added, and then the mixture was extracted with ethyl acetate. The organic layer was washed with water, 1N hydrochloric acid and saturated brine, and then dried over anhydrous sodium sulfate. The solvent was distilled off under reduced pressure to obtain the title compound (288 mg) as a colorless crystal.

1H-NMRδ (DMSO-d6): 5.34 (2H, s), 5.71 (3H, brs), 7.43 (1H, dd, J=7.6, 7.6 Hz), 7.75 (1H, dd, J=8.4, 7.6 Hz), 7.90 (1H, d, J=7.6 Hz), 8.02 (1H, d, J=8.4 Hz), 8.14 (1H, d, J=1.9 Hz), 825 (1H, d, J=1.9 Hz). MS (m/z): 434 (M-H)-.

Example 25

3-(5-t-butyl-4-hydroxy-3-methylsulfonylbenzoyl)-1,1-dioxo-2,3-dihydro-1,3-benzothiazole (a) Synthesis of methyl 3-t-butyl-4-hydroxy-5-methylsulfanylbenzoate Methyl 3-t-butyl-4-hydroxy-5-iodobenzoate (1.00 g) was dissolved in N,N-dimethylformamide (10 mL), and 2,2'-bipyridine (47 mg), zinc powder (391 mg), nickel bromide (66 mg) and dimethyl disulfide (142 mg) were added to the solution, and then the mixture was stirred at 130° C. for 1 hour. After the reaction solution was filtered, 1N hydrochloric acid was added and the reaction mixture was extracted with ethyl acetate. The organic layer was washed with saturated brine, and then dried over anhydrous sodium sulfate. The solvent was distilled off under reduced pressure and the obtained residue was purified by silica gel column chromatography (n-hexane:ethyl acetate=12:1) to obtain the title compound (382 mg) as a pale yellow oily substance.

(b) Synthesis of methyl 3-t-butyl-4-methoxy-5-methylsulfanylbenzoate

Methyl 3-t-butyl-4-hydroxy-5-methylsulfanylbenzoate (377 mg) was dissolved in N,N-dimethylformamide (7 mL), and potassium carbonate (818 mg) and dimethylsulfuric acid (0.32 mL) were added to the solution, and then the mixture was stirred at room temperature for 20 hours. Water was added to the reaction solution, and then the reaction mixture was extracted with ethyl acetate. The organic layer was washed with saturated brine, and then dried over anhydrous sodium sulfate. The solvent was distilled off under reduced pressure to obtain the title compound (344 mg) as a pale yellow oily substance.

(c) Synthesis of methyl 3-t-butyl-4-methoxy-5-methylsulfonyl benzoate

Methyl 3-t-butyl-4-methoxy-5-methylsulfanylbenzoate (344 mg) was dissolved in chloroform (7 mL), and 70% metachloroperbenzoic acid (884 mg) was added to the solution, and then the mixture was stirred at room temperature for 3 hours. After the solvent was distilled off under reduced pressure, 1N sodium hydroxide was added and the mixture was extracted with ethyl acetate. The organic layer was washed with 1N sodium hydroxide and saturated brine, and then dried over anhydrous sodium sulfate. The solvent was distilled off under reduced pressure to obtain the title compound (387 mg) as a colorless crystal.

(d) Synthesis of 3-t-butyl-4-methoxy-5-methylsulfonyl benzoic acid

Methyl 3-t-butyl-4-methoxy-5-methylsulfonyl benzoate (382 mg) was dissolved in tetrahydrofuran (4 mL) and water (2 mL), and lithium hydroxide monohydrate (320 mg) was added to the solution, and then the mixture was stirred at room temperature for 5 hours. After the organic solvent was distilled off, the aqueous layer was acidified with 1N hydrochloric acid and then extracted with ethyl acetate. The organic layer was washed with saturated brine, dried over anhydrous sodium sulfate and then concentrated under reduced pressure to obtain the title compound (372 mg) as a colorless crystal.

1H-NMRδ (CDCl$_3$): 1.43 (9H, s), 3.32 (3H, s), 3.99 (3H, s), 8.26 (1H, d, J=2.2 Hz), 8.32 (1H, d, J=22 Hz). MS (m/z): 285 (M-H)-.

(e) Synthesis of 3-t-butyl-4-methoxy-5-methylsulfonylbenzoyl chloride

To 3-t-butyl-4-methoxy-5-methylsulfonyl benzoic acid (200 mg), toluene (4 mL), N,N-dimethylformamide (1 droplet) and thionyl chloride (80 μL) were added to the solution, and then the mixture was stirred at 60° C. for 16 hours. The solvent was distilled off under reduced pressure and the obtained residue was azeotroped with toluene and used for the synthesis of (f).

(f) Synthesis of 3-(3-t-butyl-4-methoxy-5-methylsulfonylbenzoyl)-2,3-dihydro-1,3-benzothiazole 2,3-dihydro-1,3-benzothiazole synthesized from 2-aminobenzenethiol (182 mg) and 37% formalin (87 μL) in the same manner as in Example 1 was dissolved in chloroform (4 mL), and triethylamine (0.29 mL) and 3-t-butyl-4-methoxy-5-methanesulfonylbenzoyl chloride were added to the solution, and then the mixture was stirred at room temperature for 1 hour. The solvent was distilled off under reduced pressure, water was added and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was purified by silica gel column chromatography (n-hexane:ethyl acetate=4:1) to obtain the title compound (246 mg) as a pale yellow amorphous product.

(g) Synthesis of 3-(3-t-butyl-4-methoxy-5-methylsulfonylbenzoyl)-1,1-dioxo-2,3-dihydro-1,3-benzothiazole 3-(3-t-butyl-4-methoxy-5-methylsulfonylbenzoyl)-2,3-dihydro-1,3-benzothiazole (241 mg) was dissolved in chloroform (5 mL), and 70% metachloroperbenzoic acid (410 mg) was added to the solution, and then the mixture was stirred at room temperature for 16 hours and quenched with 10% sodium thiosulfate. After the solvent was distilled off under reduced pressure, 1N sodium hydroxide was added and the mixture was extracted with ethyl acetate. The organic layer was washed with 1N sodium hydroxide and saturated brine, and then dried over anhydrous sodium sulfate. The solvent was distilled off under reduced pressure to obtain the title compound (236 mg) as a colorless amorphous product.

(h) Synthesis of 3-(3-t-butyl-4-hydroxy-5-methylsulfonylbenzoyl)-1,1-dioxo-2,3-dihydro-1,3-benzothiazole 3-(3-t-butyl-4-methoxy-5-methylsulfonylbenzoyl)-1,1-dioxo-2,3-dihydro-1,3-benzothiazole (232 mg) was dissolved in N,N-dimethylformamide (5 mL), and lithium chloride (225 mg) was added to the solution, and then the mixture was stirred at 130° C. for 2 hours. To the reaction solution, 1N hydrochloric acid was added, and then the mixture was extracted with ethyl acetate. The organic layer was washed with water, 1N hydrochloric acid and saturated brine, and then dried over anhydrous sodium sulfate. The solvent was distilled off under reduced pressure and the obtained residue was purified by silica gel column chromatography (n-hexane: ethyl acetate=1:1) to obtain the title compound (201 mg) as a colorless amorphous product.

1H-NMRδ (DMSO-d6): 1.40 (9H, s), 3.42 (3H, s), 5.33 (2H, s), 7.43 (1H, dd, J=7.6, 7.6 Hz), 7.75 (1H, ddd, J=8.3, 7.6, 1.3 Hz), 7.80 (1H, d, J=2.2 Hz), 7.91 (1H, d, J=7.6 Hz), 7.97 (1H, d, J=8.3 Hz), 7.99 (1H, d, J=2.2 Hz), 10.06 (1H, brs). MS (m/z): 422 (M-H)-.

Example 26

3-(4-hydroxy-3-methoxy-5-trifluoromethylbenzoyl)-1,1-dioxo-2,3-dihydro-1,3-benzothiazole (a) Synthesis of ethyl 4-benzyloxy-3-methoxy-5-trifluoromethyl benzoate Ethyl 4-hydroxy-3-methoxy-5-trifluoromethyl benzoate (583 mg) was dissolved in N,N-dimethylformamide (5 mL), and 60% sodium hydride (132 mg) was added to the solution at 0° C. After stirring the mixture for 30 minutes, benzyl bromide (0.31 mL) was added to the solution and then the mixture was stirred for 14 hours. Water was added to the reaction solution, and then the reaction mixture was extracted with ethyl acetate. The organic layer was washed with water and saturated brine, and then dried over anhydrous sodium sulfate. The solvent was distilled off under reduced pressure and the obtained residue was purified by silica gel column chromatography (n-hexane:ethyl acetate=7:1) to obtain the title compound (704 mg) as a yellow oily substance.

(b) Synthesis of 4-benzyloxy-3-methoxy-5-trifluoromethylbenzoic acid

Ethyl 4-benzyloxy-3-methoxy-5-trifluoromethylbenzoate (704 mg) was dissolved in tetrahydrofuran (6 mL) and water (2 mL), and lithium hydroxide monohydrate (333 mg) was added to the solution, and then the mixture was stirred at 60° C. for 3 hours. After the organic solvent was distilled off, the mixture was acidified with 1N hydrochloric acid and then extracted with ethyl acetate. The organic layer was washed with saturated brine, and then dried over anhydrous sodium sulfate. The solvent was distilled off under reduced pressure to obtain the title compound (606 mg) as a colorless crystal.

1H-NMRδ (CDCl3): 4.00 (3H, s), 5.21 (2H, s), 7.33-7.54 (5H, m), 7.85 (1H, s), 8.00 (1H, s). MS (m/z): 325 (M-H)-.

(c) Synthesis of 4-benzyloxy-3-methoxy-5-trifluoromethylbenzoyl chloride

To 4-benzyloxy-3-methoxy-5-trifluoromethylbenzoic acid (601 mg), toluene (6 mL), N,N-dimethylformamide (1 droplet) and thionyl chloride (0.16 mL) were added, and then the mixture was stirred at 60° C. for 16 hours. The solvent was distilled off under reduced pressure and then azeotroped with toluene to obtain the title compound (657 mg) as a yellow oily substance.

(d) Synthesis of 3-(4-benzyloxy-3-methoxy-5-trifluoromethylbenzoyl)-2,3-dihydro-1,3-benzothiazole 2,3-dihydro-1,3-benzothiazole synthesized from 2-aminobenzenethiol (346 mg) and 37% formalin (0.23 mL) in the same manner as in Example 1 was dissolved in dichloromethane (3 mL), and diisopropylethylamine (0.63 mL) and 4-benzyloxy-3-methoxy-5-trifluoromethylbenzoyl chloride (657 mg) were added to the solution, and then the mixture was stirred at room temperature for 1 hour. The solvent was distilled off under reduced pressure and water was added, and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was purified by silica gel column chromatography (n-hexane:ethyl acetate=6:1) to obtain the title compound (578 mg) as a yellow oily substance.

(e) Synthesis of 3-(4-benzyloxy-3-methoxy-5-trifluoromethylbenzoyl)-1,1-dioxo-2,3-dihydro-1,3-benzothiazole 3-(4-benzyloxy-3-methoxy-5-trifluoromethylbenzoyl)-2,3-dihydro-1,3-benzothiazole (578 mg) was dissolved in dichloromethane (10 mL), and 70% metachloroperbenzoic acid (1.94 g) was added to the solution. After stirring the mixture at room temperature for 4 hours, 1N sodium hydroxide was added and then the mixture was extracted with ethyl acetate. The organic layer was washed with 1N sodium hydroxide and saturated brine, and then dried over anhydrous sodium sulfate. The solvent was distilled off under reduced pressure to obtain the title compound (574 mg) as a colorless oily substance.

(f) Synthesis of 3-(4-hydroxy-3-methoxy-5-trifluoromethylbenzoyl)-1,1-dioxo-2,3-dihydro-1,3-benzothiazole 3-(4-benzyloxy-3-methoxy-5-trifluoromethylbenzoyl)-1,1-dioxo-2,3-dihydro-1,3-benzothiazole (574 mg) was dissolved in tetrahydrofuran (6 mL), and 5% palladium-carbon (310 mg) was added to the solution, and then the mixture was stirred at room temperature for 22 hours under a hydrogen atmosphere. The reaction solution was filtered, and then the solvent was distilled off under reduced pressure and the obtained residue was crystallized from n-hexane-chloroform to obtain the title compound (353 mg) as a colorless crystal.

1H-NMRδ (DMSO-d6): 3.93 (3H, s), 5.35 (2H, s), 7.43 (1H, dd, J=8.1, 7.3 Hz), 7.47 (1H, s), 7.54 (1H, s), 7.76 (1H, dd, J=7.3, 7.3 Hz), 7.90 (1H, d, J=7.3 Hz), 8.02 (1H, d, J=8.1 Hz), 10.68 (1H, s). MS (m/z): 386 (M-H)-.

Example 27

3-(3-dimethylcarbamoyl-4-hydroxy-5-trifluoromethylbenzoyl)-1,1-dioxo-2,3-dihydro-1,3-benzothiazole (a) Synthesis of methyl 3-formyl-4-methoxy-5-trifluoromethyl benzoate 3-formyl-4-methoxy-5-trifluoromethylbenzoic acid (5.00 g) was dissolved in methanol (30 mL), and 1-ethyl-3-(3-dimethylaminopropyl) carbodiimide hydrochloride (4.25 g) was added to the solution, and then the mixture was stirred at mom temperature for 90 minutes. The solvent was distilled off under reduced pressure and water was added, and then the mixture was extracted with ethyl acetate. The organic layer was washed with 1N sodium hydroxide and saturated brine, and then dried over anhydrous sodium sulfate. The solvent was distilled off under reduced pressure and the obtained residue was purified by silica gel column chromatography (n-hexane:ethyl acetate=4:1) to obtain the title compound (2.98 g) as a colorless crystal.

(b) Synthesis of 4-methoxy-5-trifluoromethylisophthalic acid-1-methyl ester

Methyl 3-formyl-4-methoxy-5-trifluoromethyl benzoate (1.50 g) was dissolved in acetonitrile (15 mL) and an aqueous 5% citric acid solution, and 2-methyl-2-butene (2.00 g) and sodium chlorite (776 mg) were added to the solution, and then the mixture was stirred at room temperature for 1 hour. The solvent was distilled off under reduced pressure and 1N hydrochloric acid was added, and then the mixture was extracted with ethyl acetate. The organic layer was washed with 10% sodium thiosulfate and saturated brine, and then dried over anhydrous sodium sulfate. The solvent was distilled off under reduced pressure and the obtained crystal was washed with n-hexane to obtain the title compound (1.15 g) as a colorless crystal.

(c) Synthesis of methyl 3-dimethylcarbamoyl-4-methoxy-5-trifluoromethyl benzoate 4-methoxy-5-trifluoromethylisophthalic acid-1-methyl ester (500 mg) was dissolved in dichloromethane (10 mL), and dimethylamine hydrochloride (440 mg), 1-ethyl-3-(3-dimethylaminopropyl) carbodiimide hydrochloride (1.56 g) and triethylamine (3.00 mL) was added to the solution, and then the mixture was stirred at room temperature for 4 hours. The solvent was distilled off under reduced pressure and 1N hydrochloric acid was added, and then the mixture was extracted with ethyl acetate. The organic layer was washed with 1N sodium hydroxide and saturated brine, and then dried over anhydrous sodium sulfate. The solvent was distilled off under reduced pressure to obtain the title compound (356 mg) as a pale yellow crystal.

(d) Synthesis of 3-dimethylcarbamoyl-4-methoxy-5-trifluoromethylbenzoic acid

Methyl 3-dimethylcarbamoyl-4-methoxy-5-trifluoromethyl benzoate (348 mg) was dissolved in tetrahydrofuran (3 mL) and water (1.5 mL), and lithium hydroxide monohydrate (191 mg) was added to the solution, and then the mixture was stirred at room temperature for 1 hour. The organic solvent was distilled off under reduced pressure and acidified with 1N hydrochloric acid, and then the mixture was extracted with ethyl acetate. The organic layer was washed with saturated brine, and then dried over anhydrous sodium sulfate. The solvent was distilled off under reduced pressure to obtain the title compound (341 mg) as a colorless crystal.

1H-NMRδ (CDCl3): 2.91 (3H, s), 3.18 (3H, s), 3.96 (3H, s), 8.22 (1H, d, J=2.3 Hz), 8.35 (1H, dd, J=2.3, 0.6 Hz). MS (m/z): 290 (M-H)-.

(e) Synthesis of 3-dimethylcarbamoyl-4-methoxy-5-trifluoromethylbenzoyl chloride To 3-dimethylcarbamoyl-4-methoxy-5-trifluoromethylbenzoic acid (333 mg), toluene (3 mL), N,N-dimethylformamide (1 droplet) and thionyl chloride (0.13 mL) was added, and then the mixture was stirred at 60° C. for 6 hours. The solvent was distilled off under reduced pressure and the obtained residue was azeotroped with toluene and used for the synthesis of (f).

(f) Synthesis of 3-(3-dimethylcarbamoyl-4-methoxy-5-trifluoromethylbenzoyl)-2,3-dihydro-1,3-benzothiazole 2,3-dihydro-1,3-benzothiazole synthesized from 2-aminobenzenethiol (214 mg) and 37% formalin (0.14 mL) in the same manner as in Example 1 was dissolved in chloroform (4 mL), and triethylamine (0.47 mL) and 3-dimethylcarbamoyl-4-methoxy-5-trifluoromethylbenzoyl chloride were added to the solution, and then the mixture was stirred at room temperature for 1 hour. The solvent was distilled off under reduced pressure and water was added, and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was used for the synthesis of (g).

(g) Synthesis of 3-(3-dimethylcarbamoyl-4-methoxy-5-trifluoromethylbenzoyl)-1,1-dioxo-2,3-dihydro-1,3-benzothiazole 3-(3-dimethylcarbamoyl-4-methoxy-5-trifluoromethylbenzoyl)-2,3-dihydro-1,3-benzothiazole was dissolved in chloroform (8 mL), and 70% metachloroperbenzoic acid (718 mg) was added to the solution, and then the mixture was stirred at room temperature for 20 hours and quenched with 10% sodium thiosulfate. The solvent was distilled off under reduced pressure and 1N sodium hydroxide was added, and then the mixture was extracted with ethyl acetate. The organic layer was washed with 1N sodium hydroxide and saturated brine, and then dried over anhydrous sodium sulfate. The solvent was distilled off under reduced pressure and the obtained residue was purified by silica gel column chromatography (n-hexane:ethyl acetate=2:1) to obtain the title compound (298 mg) as a pale yellow amorphous product.

(h) Synthesis of 3-(3-dimethylcarbamoyl-4-hydroxy-5-trifluoromethylbenzoyl)-1,1-dioxo-2,3-dihydro-1,3-benzothiazole 3-(3-dimethylcarbamoyl-4-methoxy-5-trifluoromethylbenzoyl)-1,1-dioxo-2,3-dihydro-1,3-benzothiazole (291 mg) was dissolved in N,N-dimethylformamide (3 mL), and lithium chloride (279 mg) was added to the solution, and then the mixture was stirred at 120° C. for 2 hours. To the reaction solution, 1N hydrochloric acid was added, and then the mixture was extracted with ethyl acetate. The organic layer was washed with 1N hydrochloric acid and saturated brine, and then dried over anhydrous sodium sulfate. The solvent was distilled off under reduced pressure to obtain the title compound (257 mg) as a colorless crystal.

1H-NMRδ (DMSO-d6): 2.96 (6H, s), 5.39 (2H, s), 7.43 (1H, dd, J=7.6, 7.6 Hz), 7.55 (1H, ddd, J=8.4, 7.6, 1.3 Hz), 7.79 (1H, d, J=2.1 Hz), 7.90 (1H, d, J=7.6 Hz), 7.93 (1H, d, J=2.1 Hz), 8.02 (1H, d, J=8.4 Hz), 11.27 (1H, s). MS (m/z): 427 (M-H)-.

Example 28

3-(4-hydroxy-3-trifluoromethylbenzoyl)-1,1-dioxo-2,3-dihydro-1,3-benzothiazole

(a) Synthesis of acetic acid-2-trifluoromethylphenyl ester 2-trifluoromethylphenol (20.00 g) was dissolved in chloroform (160 mL), and triethylamine (34.0 mL) and acetic anhydride (12.4 mL) were added to the solution, and then the mixture was stirred at room temperature for 3 hours. The solvent was distilled off under reduced pressure and water was added, and then the mixture was extracted with ethyl acetate. The organic layer was washed with saturated brine, and then dried over anhydrous sodium sulfate. The solvent was distilled off under reduced pressure to obtain the title compound (23.76 g) as a pale yellow oily substance.

(b) Synthesis of 1-(4-hydroxy-3-trifluoromethylphenyl)ethanone

Acetic acid-2-trifluoromethylphenyl ester (10.00 g) was dissolved in trifluoromethanesulfonic acid (10.0 mL), and the solution was stirred at room temperature for 16 hours. The reaction solution was poured into ice water, and the reaction mixture was extracted with ethyl acetate. The organic layer was washed with water and saturated brine, and then dried over anhydrous sodium sulfate. The solvent was distilled off under reduced pressure and the obtained crystal was washed with n-hexane to obtain the title compound (4.47 g) as a colorless crystal.

(c) Synthesis of 1-(4-methoxymethoxy-3-trifluoromethylphenyl)ethanone 1-(4-hydroxy-3-trifluoromethylphenyl)ethanone (2.01 g) was dissolved in N,N-dimethylformamide (20 mL), and potassium carbonate (2.70 g) and chloromethyl methyl ether (1.10 mL) were added to the solution, and then the mixture was stirred at room temperature for 1 hour. Water was added to the reaction solution and the reaction mixture was extracted with ethyl acetate. The organic layer was washed with water and saturated brine, and then dried over anhydrous sodium sulfate. The solvent was distilled off under reduced pressure to obtain the title compound (2.33 g) as a pale yellow oily substance.

(d) Synthesis of methyl 4-hydroxy-3-trifluoromethoxybenzoate 1-(4-methoxymethoxy-3-trifluoromethylphenyl)ethanone (2.33 g) was dissolved in methanol (20 mL), and a 5M sodium methoxide-methanol solution (9.40 mL) and N-bromosuccinimide (5.10 g) were added to the solution, and then the mixture was stirred at room temperature for 30 minutes. The solvent was distilled off under reduced pressure and water was added, and then the mixture was extracted with ethyl acetate. The organic layer was washed with 10% sodium thiosulfate and saturated brine, and then dried over anhydrous sodium sulfate. The solvent was distilled off under reduced pressure and 4N hydrochloric acid-ethyl acetate (20 mL) was added, and then the mixture was stirred at room temperature for 30 minutes. The reaction solution was washed with water and saturated brine, and then dried over anhydrous sodium sulfate. The solvent was distilled off under reduced pressure to obtain the title compound (1.42 g) as a colorless crystal.

(e) Synthesis of methyl 4-benzyloxy-3-trifluoromethyl benzoate

Methyl 4-hydroxy-3-trifluoromethoxybenzoate (936 mg) was dissolved in N,N-dimethylformamide (10 mL), and potassium carbonate (1.29 g) and benzyl bromide (0.58 mL) were added to the solution, and then the mixture was stirred at room temperature for 24 hours. Water was added to the reaction solution and the reaction mixture was extracted with ethyl acetate. The organic layer was washed with water and saturated brine, and then dried over anhydrous sodium sulfate. The solvent was distilled off under reduced pressure and the obtained residue was purified by silica gel column chromatography (n-hexane:ethyl acetate=4:1) to obtain the title compound (1.70 g) as a yellow crystal.

(f) Synthesis of 4-benzyloxy-3-trifluoromethylbenzoic acid

Methyl 4-benzyloxy-3-trifluoromethyl benzoate (1.38 g) was dissolved in tetrahydrofuran (10 mL) and water (5 mL), and lithium hydroxide monohydrate (1.49 g) was added to the solution, and then the mixture was stirred at room temperature for 20 hours. The solvent was distilled off under reduced pressure and 1N hydrochloric acid was added, and then the mixture was extracted with ethyl acetate. The organic layer was washed with saturated brine, and then dried over anhydrous sodium sulfate. The solvent was distilled off under reduced pressure to obtain the title compound (1.25 g) as a pale yellow crystal.

1H-NMRδ (DMSO-d6): 5.38 (2H, s), 7.31-7.51 (6H, m), 8.12 (1H, d, J=2.1 Hz), 8.19 (1H, d, J=8.6, 2.1 Hz), 13.12 (1H, brs). MS (m/z): 269 (M-H)-.

(g) Synthesis of 4-benzyloxy-3-trifluoromethylbenzoyl chloride

To 4-benzyloxy-3-trifluoromethylbenzoic acid (444 mg), toluene (5 mL), N,N-dimethylformamide (2 droplets) and thionyl chloride (0.16 mL) were added, and then the mixture was stirred at 60° C. for 20 hours. The solvent was distilled off under reduced pressure and then azeotroped with toluene, and the obtained product was used for the synthesis of (h).

(h) Synthesis of 3-(4-benzyloxy-3-trifluoromethylbenzoyl)-2,3-dihydro-1,3-benzothiazole 2,3-dihydro-1,3-benzothiazole synthesized from 2-aminobenzenethiol (282 mg) and 37% formalin (0.19 mL) in the same manner as in Example 1 was dissolved in chloroform (6 mL), and triethylamine (0.62 mL) and 4-benzyloxy-3-trifluoromethylbenzoyl chloride were added to the solution, and then the mixture was stirred at mom temperature for 1.5 hours. The solvent was distilled off under reduced pressure and water was added, and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was purified by silica gel column chromatography (n-hexane:ethyl acetate=4:1) to obtain the title compound (356 mg) as a pale yellow oily substance.

(i) Synthesis of 3-(4-benzyloxy-3-trifluoromethylbenzoyl)-1,1-dioxo-2,3-dihydro-1,3-benzothiazole 3-(4-benzyloxy-3-trifluoromethylbenzoyl)-2,3-dihydro-1,3-benzothiazole (600 mg) was dissolved in chloroform (10 mL), and 70% metachloroperbenzoic acid (1.04 g) was added to the solution, and then the mixture was stirred at room temperature for 20 hours and quenched with 10% sodium thiosulfate. The solvent was distilled off under reduced pressure and 1N sodium hydroxide was added, and then the mixture was extracted with ethyl acetate. The organic layer was washed with 1N sodium hydroxide and saturated brine, and then dried over anhydrous sodium sulfate. The solvent was distilled off under reduced pressure and the obtained residue was purified by silica gel column chromatography (n-hexane:ethyl acetate=2:1) to obtain the title compound (495 mg) as a colorless crystal.

(j) Synthesis of 3-(4-hydroxy-3-trifluoromethylbenzoyl)-1,1-dioxo-2,3-dihydro-1,3-benzothiazole 3-(4-benzyloxy-3-trifluoromethylbenzoyl)-1,1-dioxo-2,3-dihydro-1,3-benzothiazole (490 mg) was dissolved in tetrahydrofuran (5 mL) and methanol (5 mL), and 20% palladium hydroxide-carbon (100 mg) was added to the solution, and then the mixture was stirred at room temperature for 6 hours under a hydrogen atmosphere. After the reaction solution was filtered, the solvent was distilled off under reduced pressure and then the obtained residue was crystallized from diethylether to obtain the title compound (397 mg) as a colorless crystal.

1H-NMRδ (DMSO-d6): 5.29 (2H, s), 7.14 (1H, d, J=8.4 Hz), 7.41 (1H, ddd, J=8.2, 7.8, 0.9 Hz), 7.72 (1H, ddd, J=8.5, 7.3, 1.3 Hz), 7.80 (1H, dd, J=8.4, 2.2 Hz), 7.84-7.88 (2H, m), 7.91 (1H, d, J=8.2 Hz), 11.35 (1H, brs). MS (m/z): 356 (M-H)-.

Example 29

3-(3-chloro-4-hydroxy-5-methoxybenzoyl)-1,1-dioxo-2,3-dihydro-1,3-benzothiazole

(a) Synthesis of 4-benzyloxy-3-chloro-5-methoxybenzoyl chloride

To 4-benzyloxy-3-chloro-5-methoxybenzoic acid (541 mg), toluene (5.4 mL), N,N-dimethylformamide (1 droplet) and thionyl chloride (0.16 mL) were added, and then the mixture was stirred at 60° C. for 16 hours. The solvent was distilled off under reduced pressure and then azeotroped with toluene to obtain the title compound (578 mg) as a yellow solid.

(b) Synthesis of 3-(4-benzyloxy-3-chloro-5-methoxybenzoyl)-2,3-dihydro-1,3-benzothiazole 2,3-dihydro-1,3-benzothiazole synthesized from 2-aminobenzenethiol (347 mg) and 37% formalin (0.23 mL) in the same manner as in Example 1 was dissolved in dichloromethane (3 mL), and diisopropylethylamine (0.63 mL) and 4-benzyloxy-3-chloro-5-methoxybenzoyl chloride (578 mg) were added to the solution, and then the mixture was stirred at room temperature for 1.5 hours. The solvent was distilled off under reduced pressure and water was added, and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was purified by silica gel column chromatography (n-hexane:ethyl acetate=6:1) to obtain the title compound (498 mg) as a pale yellow oily substance.

(c) Synthesis of 3-(4-benzyloxy-3-chloro-5-methoxybenzoyl)-1,1-dioxo-2,3-dihydro-1,3-benzothiazole 3-(4-benzyloxy-3-chloro-5-methoxybenzoyl)-2,3-dihydro-1,3-benzothiazole (498 mg) was dissolved in dichloromethane (10 mL), and 70% metachloroperbenzoic acid (1.22 g) was added to the solution. After stirring the mixture at room temperature for 16 hours, 1N sodium hydroxide was added, and then the mixture was extracted with ethyl acetate. The organic layer was washed with 1N sodium hydroxide and saturated brine, and then dried over anhydrous sodium sulfate. The solvent was distilled off under reduced pressure to obtain the title compound (521 mg) as a pale yellow oily substance.

(d) Synthesis of 3-(3-chloro-4-hydroxy-5-methoxybenzoyl)-1,1-dioxo-2,3-dihydro-1,3-benzothiazole 3-(4-benzyloxy-3-chloro-5-methoxybenzoyl)-1,1-dioxo-2,3-dihydro-1,3-benzothiazole (519 mg) was dissolved in tetrahydrofuran (5 mL), and 20% palladium hydroxide-carbon (101 mg) was added to the solution, and then the mixture was stirred at room temperature for 21 hours under a hydrogen atmosphere. After the reaction solution was filtered, the solvent was distilled off under reduced pressure and then the obtained residue was crystallized from chloroform to obtain the title compound (185 mg) as a colorless crystal.

1H-NMRδ (DMSO-d6): 3.88 (3H, s), 5.34 (2H, s), 7.27 (1H, s), 7.35 (1H, s), 7.43 (1H, dd, J=7.6 Hz, 7.6 Hz), 7.75 (1H, dd, J=8.4, 7.6 Hz), 7.90 (1H, d, J=7.6 Hz), 7.99 (1H, d, J=8.4 Hz). MS (m/z): 352 (M-H)-.

Example 30

3-[4-hydroxy-3-(pyrrolidine-1-carbonyl)-5-trifluoromethylbenzoyl]-1,1-dioxo-2,3-dihydro-1,3-benzothiazole

(a) Synthesis of methyl 4-methoxy-3-(pyrrolidine-1-carbonyl)-5-trifluoromethyl benzoate 4-methoxy-5-trifluoromethylisophthalic acid-1-methyl ester (4.35 g) was dissolved in dichloromethane (50 mL), and pyrrolidine (1.10 g) and 1-ethyl-3-(3-dimethylaminopropyl)carbodiimide hydrochloride (2.99 g) were added to the solution, and then the mixture was stirred at room temperature for 16 hours. The solvent was distilled off under reduced pressure and 1N hydrochloric acid was added, and then the mixture was extracted with ethyl acetate. The organic layer was washed with 1N sodium hydroxide and saturated brine, and then dried over anhydrous sodium sulfate. The solvent was distilled off under reduced pressure and the obtained residue was purified by silica gel column chromatography (n-hexane:ethyl acetate=2:3) to obtain the title compound (1.33 g) as a brown oily substance.

(b) Synthesis of 4-methoxy-3-(pyrrolidine-1-carbonyl)-5-trifluoromethylbenzoic acid Methyl 4-methoxy-3-(pyrrolidine-1-carbonyl)-5-trifluoromethyl benzoate (1.33 g) was dissolved in tetrahydrofuran (8 mL) and water (4 mL), and lithium hydroxide monohydrate (708 mg) was added to the solution, and then the mixture was stirred at room temperature for 1 hour. The organic solvent was distilled off under reduced pressure and the aqueous layer was washed with diisopropylether. The aqueous layer was acidified with 1N hydrochloric acid and then extracted with ethyl acetate. The organic layer was washed with saturated brine, and then dried over anhydrous sodium sulfate. The solvent was distilled off under reduced pressure to obtain the title compound (790 mg) as a colorless amorphous product.

(c) Synthesis of 4-methoxy-3-(pyrrolidine-1-carbonyl)-5-trifluoromethylbenzoyl chloride To 4-methoxy-3-(pyrrolidine-1-carbonyl)-5-trifluoromethylbenzoic acid (785 mg), toluene (8 mL) and oxalyl chloride (0.64 mL) were added, and then the mixture was stirred at room temperature for 22 hours. The solvent was distilled off under reduced pressure and the obtained product was used for the synthesis of (d).

(d) Synthesis of 3-[4-methoxy-3-(pyrrolidine-1-carbonyl)-5-trifluoromethylbenzoyl]-2,3-dihydro-1,3-benzothiazole 2,3-dihydro-1,3-benzothiazole synthesized from 2-aminobenzenethiol (464 mg) and 37% formalin (0.31 mL) in the same manner as in Example 1 was dissolved in chloroform (10 mL), and triethylamine (1.03 mL) and 4-methoxy-3-(pyrrolidine-1-carbonyl)-5-trifluoromethylbenzoyl chloride were added to the solution, and then the mixture was stirred at room temperature for 2 hours. The solvent was distilled off under reduced pressure and water was added, and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was purified by silica gel column chromatography (n-hexane:ethyl acetate=1:2) to obtain the title compound (778 mg) as a pale yellow amorphous product.

(e) Synthesis of 3-[4-methoxy-3-(pyrrolidine-1-carbonyl)-5-trifluoromethylbenzoyl]-1,1-dioxo-2,3-dihydro-1,3-benzothiazole 3-[4-methoxy-3-(pyrrolidine-1-carbonyl)-5-trifluoromethylbenzoyl]-2,3-dihydro-1,3-benzothiazole (773 mg) was dissolved in chloroform (15 mL), and 70% metachloroperbenzoic acid (1.22 g) was added to the solution, and then the mixture was stirred at room temperature for 16 hours and quenched with 10% sodium thiosulfate. After the solvent was distilled off under reduced pressure, 1N sodium hydroxide was added, and then the mixture was extracted with ethyl acetate. The organic layer was washed with 1N sodium hydroxide and saturated brine, and then dried over anhydrous sodium sulfate. The solvent was distilled off under reduced pressure to obtain the title compound (720 mg) as a white amorphous product.

(f) Synthesis of 3-[4-hydroxy-3-(pyrrolidine-1-carbonyl)-5-trifluoromethylbenzoyl]-1,1-dioxo-2,3-dihydro-1,3-benzothiazole 3-[4-methoxy-3-(pyrrolidine-1-carbonyl)-5-trifluoromethylbenzoyl]-1,1-dioxo-2,3-dihydro-1,3-benzothiazole (715 mg) was dissolved in N,N-dimethylformamide (7 mL), and lithium chloride (649 mg) was added to the solution, and then the mixture was stirred at 120° C. for 2 hours. To the reaction solution, 1N hydrochloric acid was added, and then the mixture was extracted with ethyl acetate. The organic layer was washed with 1N hydrochloric acid and saturated brine, and then dried over anhydrous sodium sulfate. The solvent was distilled off under reduced pressure to obtain the title compound (654 mg) as a colorless amorphous product.

1H-NMRδ (DMSO-d6): 1.86 (4H, br), 3.45-3.60 (4H, t, J=6.5 Hz), 5.37 (2H, s), 7.43 (1H, ddd, J=7.8, 7.8, 0.8 Hz), 7.76 (1H, ddd, J=8.4, 7.8, 1.3 Hz), 7.90 (2H, br), 8.03 (1H, d, J=8.4 Hz), 12.29 (1H, s). MS (m/z): 453 (M-H)-.

Example 31

3-[4-hydroxy-3-(1,3-thiazolidine-3-carbonyl)-5-trifluoromethylbenzoyl]-1,1-dioxo-2,3-dihydro-1,3-benzothiazole (a) Synthesis of 3-formyl-4-methoxy-5-trifluoromethylbenzoyl chloride To 3-formyl-4-methoxy-5-trifluoromethylbenzoic acid (2.05 g), toluene (20 mL), N,N-dimethylformamide (2 droplets) and thionyl chloride (0.70 mL) were added, and then the mixture was stirred at 60° C. for 6.5 hours. The solvent was distilled off under reduced pressure and then azeotroped with toluene to obtain the title compound (2.42 g) as a brown oily substance.

(b) Synthesis of 3-(3-formyl-4-methoxy-5-trifluoromethylbenzoyl)-2,3-dihydro-1,3-benzothiazole 2,3-dihydro-1,3-benzothiazole synthesized from 2-aminobenzenethiol (1.55 g) and 37% formalin (1.0 mL) in the same manner as in Example 1 was dissolved in dichloromethane (15 mL), and diisopropylethylamine (2.7 mL) and 3-formyl-4-methoxy-5-trifluoromethylbenzoyl chloride (2.42 g) were added to the solution, and then the mixture was stirred at room temperature for 14 hours. The solvent was distilled off under reduced pressure and water was added, and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was purified by silica gel column chromatography (n-hexane:ethyl acetate=5:1) to obtain the title compound (1.44 g) as a yellow oily substance.

(c) Synthesis of 3-(3-diethoxymethyl-4-methoxy-5-trifluoromethylbenzoyl)-2,3-dihydro-1,3-benzothiazole 3-(3-formyl-4-methoxy-5-trifluoromethylbenzoyl)-2,3-dihydro-1,3-benzothiazole (277 mg) was dissolved in ethanol (1.5 mL) and triethyl orthoformate (0.16 mL), Amberlyst-15 (27 mg) was added to the solution, and then the mixture was refluxed for 3.5 hours. The reaction solution was filtered, and then the solvent was distilled off under reduced pressure to obtain the title compound (326 mg) as a yellow oily substance.

(d) Synthesis of 3-(3-formyl-4-methoxy-5-trifluoromethylbenzoyl)-1,1-dioxo-2,3-dihydro-1,3-benzothiazole 3-(3-formyl-4-methoxy-5-trifluoromethylbenzoyl)-2,3-dihydro-1,3-benzothiazole (326 mg) was dissolved in dichloromethane (6 mL), and 70% metachloroperbenzoic acid (754 mg) was added to the solution: After stirring the mixture at mom temperature for 2 hours, 1N sodium hydroxide was added and then the mixture was extracted with ethyl acetate. The organic layer was washed with 1N sodium hydroxide and saturated brine, and then dried over anhydrous sodium sulfate. The solvent was distilled off under reduced pressure and the obtained residue was dissolved in ethyl acetate (3 mL), and 4N hydrochloric acid-ethyl acetate (0.74 mL) was added to the solution, and then the mixture was stirred at room temperature for 2 hours. The reaction solution was washed with water and saturated brine, and then dried over anhydrous sodium sulfate. The solvent was distilled off under reduced pressure to obtain the title compound (248 mg) as a pale yellow oily substance.

(e) Synthesis of 5-(1,1-dioxo-2,3-dihydro-1,3-benzothiazole-3-carbonyl)-2-methoxy-3-trifluoromethylbenzoic acid 3-(3-formyl-4-methoxy-5-trifluoromethylbenzoyl)-1,1-dioxo-2,3-dihydro-1,3-benzothiazole (248 mg) was dissolved in methanol (2.5 mL) and an aqueous 10% citric acid solution (2.5 mL), and 2-methyl-2-butene (0.33 mL) and sodium chlorite (84 mg) were added to the solution, and then the mixture was stirred at room temperature for 1 hour. The solvent was distilled off under reduced pressure and 1N hydrochloric acid was added, and then the mixture was extracted with ethyl acetate. The organic layer was washed with an aqueous 10% sodium thiosulfate solution and saturated brine, and then dried over anhydrous sodium sulfate. The solvent was distilled off under reduced pressure to obtain the title compound (277 mg) as a pale yellow oily substance.

(f) Synthesis of 3-[4-methoxy-3-(1,3-thiazolidine-3-carbonyl)-5-trifluoromethylbenzoyl]-1,1-dioxo-2,3-dihydro-1,3-benzothiazole 5-(1,1-dioxo-2,3-dihydro-1,3-benzothiazole-3-carbonyl)-2-methoxy-3-trifluoromethylbenzoic acid (277 mg) was dissolved in dichloromethane (3 mL), thiazolidine (0.10 mL) and 1-ethyl-3-(3-dimethylaminopropyl)carbodiimide hydrochloride (238 mg) were added to the solution, and then the mixture was stirred at room temperature for 19 hours. The solvent was distilled off under reduced pressure and 1N hydrochloric acid was added and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was purified by silica gel column chromatography (n-hexane:ethyl acetate=1:1) to obtain the title compound (138 mg) as a colorless oily substance.

(g) Synthesis of 3-[4-hydroxy-3-(1,3-thiazolidine-3-carbonyl)-5-trifluoromethylbenzoyl]-1,1-dioxo-2,3-dihydro-1,3-benzothiazole 3-[4-methoxy-3-(1,3-thiazolidine-3-carbonyl)-5-trifluoromethylbenzoyl]-1,1-dioxo-2,3-dihydro-1,3-benzothiazole (138 mg) was dissolved in N,N-dimethylformamide (2 mL), and lithium chloride (118 mg) was added to the solution, and then the mixture was stirred at 120° C. for 1.5 hours. To the reaction solution, 1N hydrochloric acid was added, and then the mixture was extracted with ethyl acetate. The organic layer was washed with water and saturated brine, and then dried over anhydrous sodium sulfate. The solvent was distilled off under reduced pressure and the obtained residue was crystallized from n-hexane-chloroform to obtain the title compound (47 mg) as a pale yellow crystal.

1H-NMRδ (DMSO-d6): 3.06 (2H, brs), 3.77 (2H, brs), 4.58 (2H, brs), 5.38 (2H, s), 7.43 (1H, dd, J=7.6, 7.3 Hz), 7.76 (1H, dd, J=8.4, 7.3 Hz), 7.82-8.00 (2H, m), 7.97 (1H, s), 8.04 (1H, d, J=8.4 Hz), 11.52 (1H, brs). MS (m/z): 471 (M-H)-.

Example 32

3-[4-hydroxy-3-(1-oxo-1,3-thiazolidine-3-carbonyl)-5-trifluoromethylbenzoyl]-1,1-dioxo-2,3-dihydro-1,3-benzothiazole 3-[4-hydroxy-3-(1,3-thiazolidine-3-carbonyl)-5-trifluoromethylbenzoyl]-1,1-dioxo-2,3-dihydro-1,3-benzothiazole (67 mg) was dissolved in tetrahydrofuran (0.5 mL) and water (0.5 mL), and oxone (45 mg) was added to the solution, and then the mixture was stirred at room temperature for 1 hour. To the reaction solution, 1N hydrochloric acid was added, and then the mixture was extracted with ethyl acetate. The organic layer was washed with water and saturated brine, and then dried over anhydrous sodium sulfate. The solvent was distilled off under reduced pressure and the obtained residue was crystallized from n-hexane-chloroform to obtain the title compound (46 mg) as a colorless crystal.

1H-NMRδ (DMSO-d6): 2.98-3.15 (2H, m), 3.94-4.06 (1H, m), 4.22 (1H, brs), 4.61 (2H, s), 5.32 (2H, s), 7.42 (1H, dd, J=7.6, 7.6 Hz), 7.74 (1H, dd, J=8.4, 7.6 Hz), 7.86 (1H, d, J=7.6 Hz), 7.88 (1H, d, J=2.2 Hz), 7.98 (1H, d, J=2.2 Hz), 8.01 (1H, d, J=8.4 Hz). MS (m/z): 487 (M-H)-.

Example 33

1,1-dioxo-3-[3-(1,1-dioxo-1,3-thiazolidine-3-carbonyl)-4-hydroxy-5-trifluoromethylbenzoyl]-2,3-dihydro-1,3-benzothiazole (a) Synthesis of 1,1-dioxo-3-[3-(1,1-dioxo-1,3-thiazolidine-3-carbonyl)-4-methoxy-5-trifluoromethylbenzoyl]-2,3-dihydro-1,3-benzothiazole 3-[4-methoxy-3-(1,3-thiazolidine-3-carbonyl)-5-trifluoromethylbenzoyl]-1,1-dioxo-2,3-dihydro-1,3-benzothiazole (300 mg) was dissolved in chloroform (10 mL), and 70% metachloroperbenzoic acid (1.21 g) was added to the solution. After stirring the mixture at room temperature for 20 hours, 1N sodium hydroxide was added and the mixture was extracted with ethyl acetate. The organic layer was washed with 1N sodium hydroxide and saturated brine, and then dried over anhydrous sodium sulfate. The solvent was distilled off under reduced pressure to obtain the title compound (266 mg) as a colorless oily substance.

(b) Synthesis of 1,1-dioxo-3-[3-(1,1-dioxo-1,3-thiazolidine-3-carbonyl)-4-hydroxy-5-trifluoromethylbenzoyl]-2,3-dihydro-1,3-benzothiazole 1,1-dioxo-3-[3-(1,1-dioxo-1,3-thiazolidine-3-carbonyl)-4-methoxy-5-trifluoromethylbenzoyl]-2,3-dihydro-1,3-benzothiazole (260 mg) was dissolved in N,N-dimethylformamide (2.5 mL), and lithium chloride (200 mg) was added to the solution, and then the mixture was stirred at 120° C. for 1.5 hours. To the reaction solution, 1N hydrochloric acid was added, and then the mixture was extracted with ethyl acetate. The organic layer was washed with water and saturated brine, and then dried over anhydrous sodium sulfate. The solvent was distilled off under reduced pressure and the obtained residue was crystallized from n-hexane-chloroform to obtain the title compound (120 mg) as a pale yellow crystal.

1H-NMRδ (DMSO-d6): 3.50 (2H, t, J=6.8 Hz), 3.86-4.14 (2H, m), 4.64 (2H, s), 5.39 (2H, s), 7.44 (1H, dd, J=8.1, 7.6 Hz), 7.77 (1H, dd, J=8.1, 7.6 Hz), 7.88 (1H, s), 7.91 (1H, d, J=8.1 Hz), 8.01 (1H, s), 8.06 (1H, d, J=8.1 Hz). MS (m/z): 503 (M-H)-.

Example 34

3-(3-cyano-5-ethylsulfanyl-4-hydroxybenzoyl)-1,1-dioxo-2,3-dihydro-1,3-benzothiazole (a) Synthesis of methyl 3-cyano-4-methoxybenzoate Methyl 3-cyano-4-hydroxybenzoate (1.00 g) was dissolved in N,N-dimethylformamide (5 mL), and potassium carbonate (1.56 g) and dimethylsulfuric acid (0.70 mL) were added to the solution, and then the mixture was stirred at room temperature for 1 hour. After the reaction solution was filtered, water was added and the reaction mixture was extracted with ethyl acetate. The organic layer was washed with saturated brine, and then dried over anhydrous sodium sulfate. The solvent was distilled off under reduced pressure to obtain the title compound (923 mg) as a yellow solid.

(b) Synthesis of 3-cyano-4-methoxybenzoic acid

Methyl 3-cyano-4-methoxybenzoate (879 mg) was dissolved in tetrahydrofuran (8 mL) and water (4 mL), and lithium hydroxide monohydrate (772 mg) was added to the solution, and then the mixture was stirred at mom temperature for 1 hour. The organic solvent was distilled off under reduced pressure and acidified with 2N hydrochloric acid, and then the precipitated crystal was collected by filtration to obtain the title compound (754 mg) as a colorless crystal.

1H-NMRδ (DMSO-d6): 4.00 (3H, s), 7.36 (1H, dd, J=6.6, 3.0 Hz), 8.18 (1H, d, J=3.0 Hz), 8.20 (1H, dd, 2.1 Hz), 13.17 (1H, brs). MS (m/z): 176 (M-H)-.

(c) Synthesis of 3-cyano-4-methoxybenzoyl chloride

To 3-cyano-4-methoxybenzoic acid (1.78 g), toluene (20 mL), N,N-dimethylformamide (3 droplets) and thionyl chloride (1.14 mL) were added, and then the mixture was stirred at 60° C. for 16 hours. The solvent was distilled off under reduced pressure and the obtained residue was azeotroped with toluene and used for the synthesis of (d).

(d) Synthesis of 3-(3-cyano-4-methoxybenzoyl)-2,3-dihydro-1,3-benzothiazole 2,3-dihydro-1,3-benzothiazole synthesized from 2-aminobenzenethiol (1.89 g) and 37% formalin (1.25 mL) in the same manner as in Example 1 was dissolved in chloroform (20 mL), and triethylamine (2.08 mL) and 3-cyano-4-methoxybenzoyl chloride were added to the solution, and then the mixture was stirred at room temperature for 2 hours. The organic solvent was distilled off under reduced pressure and extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was used for the synthesis of (e).

(e) Synthesis of 3-(3-cyano-4-methoxybenzoyl)-1,1-dioxo-2,3-dihydro-1,3-benzothiazole 3-(3-cyano-4-methoxybenzoyl)-2,3-dihydro-1,3-benzothiazole was dissolved in chloroform (50 mL), and 70% metachloroperbenzoic acid (9.19 g) was added to the solution, and then the mixture was stirred at room temperature for 20 hours and quenched with 10% sodium thiosulfate. The solvent was distilled off under reduced pressure and 1N sodium hydroxide was added, and then the mixture was extracted with ethyl acetate. The organic layer was washed with 1N sodium hydroxide and saturated brine, and then dried over anhydrous sodium sulfate. The solvent was distilled off under reduced pressure to obtain the title compound (2.30 g) as a pale yellow solid.

(f) Synthesis of 3-(3-cyano-4-hydroxybenzoyl)-1,1-dioxo-2,3-dihydro-1,3-benzothiazole 3-(3-cyano-4-methoxybenzoyl)-1,1-dioxo-2,3-dihydro-1,3-benzothiazole (2.30 g) was dissolved in N,N-dimethylformamide (25 mL), and lithium chloride (2.97 g) was added to the solution, and then the mixture was stirred at 130° C. for 12 hours. To the reaction solution, 1N hydrochloric acid was added, and then the mixture was extracted with ethyl acetate. The organic layer was washed with 1N hydrochloric acid and saturated brine, and then dried over anhydrous sodium sulfate. The solvent was distilled off under reduced pressure and the obtained residue was used for the synthesis of (g).

(g) Synthesis of 3-(3-cyano-4-hydroxy-5-iodobenzoyl)-1,1-dioxo-2,3-dihydro-1,3-benzothiazole 3-(3-cyano-4-hydroxybenzoyl)-1,1-dioxo-2,3-dihydro-1,3-benzothiazole was dissolved in dichloromethane (27 mL) and methanol (3 mL), and N-iodosuccinimide (1.79 g) and trifluoromethanesulfonic acid (5 droplets) was added to the solution, and then the mixture was stirred at room temperature for 15 hours. The solvent was distilled off under reduced pressure and water was added, and then the mixture was extracted with ethyl acetate. The organic layer was washed with water and saturated brine, and then dried over anhydrous sodium sulfate. The solvent was distilled off under reduced pressure and the obtained residue was crystallized from n-hexane-ethyl acetate to obtain the title compound (1.30 g) as a colorless crystal.

(h) Synthesis of 3-(3-cyano-5-ethylsulfanyl-4-hydroxybenzoyl)-1,1-dioxo-2,3-dihydro-1,3-benzothiazole 3-(3-cyano-4-hydroxy-5-iodobenzoyl)-1,1-dioxo-2,3-dihydro-1,3-benzothiazole (500 mg) was dissolved in N,N-dimethylformamide (5 mL), and 2,2'-bipyridine (18 mg), zinc powder (149 mg), nickel bromide (25 mg) and diethyl disulfide (70 mg) were added to the solution, and then the mixture was stirred at 110° C. for 1 hour. After the reaction solution was filtered, 1N hydrochloric acid was added and the reaction mixture was extracted with ethyl acetate. The organic layer was washed with saturated brine, and then dried over anhydrous sodium sulfate. The solvent was distilled off under reduced pressure and the obtained residue was purified by silica gel column chromatography (n-hexane:ethyl acetate=2:1) and then crystallized from diethylether-ethyl acetate to obtain the title compound (63 mg) as a colorless crystal.

1H-NMRδ (DMSO-d6): 1.22 (3H, t, J=7.3 Hz), 2.96 (2H, q, J=7.3 Hz), 5.35 (2H, s), 7.44 (1H, dd, J=7.6, 7.6 Hz), 7.77

(1H, ddd, J=8.3, 3.6, 1.3 Hz), 7.79 (1H, d, J=1.8 Hz), 7.88-7.94 (2H, m), 8.07 (1H, d, J=8.3 Hz). MS (m/z): 373 (M-H)-.

Example 35

3-(3-cyano-4-hydroxy-5-isopropylsulfanylbenzoyl)-1,1-dioxo-2,3-dihydro-1,3-benzothiazole 3-(3-cyano-4-hydroxy-5-iodobenzoyl)-1,1-dioxo-2,3-dihydro-1,3-benzothiazole (1.03 mg) was dissolved in N,N-dimethylformamide (10 mL), 2,2'-bipyridine (37 mg), zinc powder (306 mg), nickel bromide (52 mg) and diisopropyl disulfide (176 mg) were added to the solution, and then the mixture was stirred at 110° C. for 1 hour. After the reaction solution was filtered, 1N hydrochloric acid was added and the reaction mixture was extracted with ethyl acetate. The organic layer was washed with saturated brine, and then dried over anhydrous sodium sulfate. The solvent was distilled off under reduced pressure and the obtained residue was purified by silica gel column chromatography (n-hexane:ethyl acetate=2:1) to obtain the title compound (153 mg) as a colorless crystal.

1H-NMRδ (DMSO-d6): 1.23 (6H, d, J=6.6 Hz), 3.46 (1H, sevent, J=6.6 Hz), 5.35 (2H, s), 7.44 (1H, dd, J=7.4, 7.4 Hz), 7.76 (1H, ddd, J=8.4, 7.4, 1.3 Hz), 7.90 (1H, d, J=2.1 Hz), 7.91 (1H, d, J=7.4 Hz), 7.98 (1H, d, J=2.1 Hz), 8.04 (1H, d, J=8.4 Hz), 11.32 (1H, brs). MS (m/z): 387 (M-H)-.

Example 36

3-(3-cyano-4-hydroxy-5-trifluoromethoxybenzoyl)-1,1-dioxo-2,3-dihydro-1,3-benzothiazole (a) Synthesis of 1-methoxymethoxy-2-trifluoromethoxybenzene 2-trifluoromethoxyphenol (10.00 g) was dissolved in N,N-dimethylformamide (50 mL), and potassium carbonate (15.52 g) and chloromethyl methyl ether (4.70 mL) were added to the solution, and then the mixture was stirred at room temperature for 1 hour. Water was added to the reaction solution and then the mixture was extracted with n-hexane. The organic layer was washed with saturated brine, and then dried over anhydrous sodium sulfate. The solvent was distilled off under reduced pressure to obtain the title compound (12.21 g) as a colorless oily substance.

(b) Synthesis of 2-hydroxy-3-trifluoromethoxybenzaldehyde 1-methoxymethoxy-2-trifluoromethoxybenzene (12.21 g) was dissolved in tetrahydrofuran (120 mL), and a 1.59M n-butyllithium-n-cyclohexane solution (40 mL) was added to the solution at −60° C. over 15 minutes under an argon gas flow, and then the mixture was stirred for 1 hour. N,N-dimethylformamide (6.30 mL) was added to the solution, and then the mixture was stirred at room temperature for 30 minutes. 2N hydrochloric acid (100 mL) was added to the solution, and then the mixture was stirred at 60° C. for 15 hours. The organic solvent was distilled off under reduced pressure, and then the mixture was extracted with ethyl acetate. The organic layer was washed with saturated brine, and then dried over anhydrous sodium sulfate. The solvent was distilled off under reduced pressure to obtain the title compound (10.38 g) as a colorless crystal.

(c) Synthesis of 5-bromo-2-hydroxy-3-trifluoromethoxybenzaldehyde 2-hydroxy-3-trifluoromethoxybenzaldehyde (10.38 g) was dissolved in dichloromethane (100 mL), and N-bromosuccinimide (9.41 g) was added to the solution, and then the mixture was stirred at room temperature for 30 minutes. The solvent was distilled off under reduced pressure and water was added, and then the mixture was extracted with ethyl acetate. The organic layer was washed with 1N hydrochloric acid, 10% sodium thiosulfate and saturated brine, and then dried over anhydrous sodium sulfate. The solvent was distilled off under reduced pressure to obtain the title compound (14.27 g) as a brown solid.

(d) Synthesis of 5-bromo-2-methoxy-3-trifluoromethoxybenzaldehyde 5-bromo-2-hydroxy-3-trifluoromethoxyaldehyde (5.00 g) was dissolved in N,N-dimethylformamide (25 mL), and potassium carbonate (4.85 g) and dimethylsulfuric acid (2.5 mL) was added to the solution, and then the mixture was stirred at room temperature for 16 hours. Water was added to the reaction solution and the reaction mixture was extracted with ethyl acetate. The organic layer was washed with water and saturated brine, and then dried over anhydrous sodium sulfate. The solvent was distilled off under reduced pressure to obtain the title compound (5.22 g) as a brown oily substance.

(e) Synthesis of 5-bromo-1-diethoxymethyl-2-methoxy-3-trifluoromethoxybenzene 5-bromo-2-methoxy-3-trifluoromethoxybenzaldehyde (5.22 g) was dissolved in n-hexane (15 mL) and triethyl orthoformate (4.4 mL), and Amberlyst-15 (522 mg) was added to the solution, and then the mixture was refluxed for 3 hours. The reaction solution was filtered, and then the solvent was distilled off under reduced pressure to obtain the title compound (6.19 g) as a brown oily substance.

(f) Synthesis of 3-formyl-4-methoxy-5-trifluoromethoxybenzoic acid

To magnesium (403 mg), tetrahydrofuran (16 mL), 5-bromo-1-diethoxymethyl-2-methoxy-3-trifluoromethoxybenzene (6.19 g) and a 0.97M methylmagnesium bromide-tetrahydrofuran solution (0.42 mL) were added to the solution, and then the mixture was stirred at room temperature for 1 hour. The reaction solution was cooled to 0° C. and stirred for 45 minutes under a carbon dioxide atmosphere. 4N hydrochloric acid (25 mL) was added and then the mixture was stirred at room temperature for 30 minutes. The organic solvent was distilled off under reduced pressure and the mixture was extracted with diisopropylether. The organic layer was extracted with 1N sodium hydroxide (100 mL) added thereto and the aqueous layer was washed twice with diisopropylether. The aqueous layer was acidified with 4N hydrochloric acid and then extracted with ethyl acetate. The organic layer was washed with saturated brine, and then dried over anhydrous sodium sulfate. The solvent was distilled off under reduced pressure to obtain the title compound (4.22 g) as a brown solid.

(g) Synthesis of 3-cyano-4-methoxy-5-trifluoromethoxybenzoic acid 3-formyl-4-methoxy-5-trifluoromethoxybenzoic acid (4.22 g) was dissolved in formic acid (20 mL), and hydroxylamine hydrochloride (1.22 g) was added to the solution, and then the mixture was refluxed for 16 hours. The solvent was distilled off under reduced pressure and 1N hydrochloric acid was added, and then the mixture was extracted with ethyl acetate. The organic layer was washed with saturated brine, and then dried over anhydrous sodium sulfate. The solvent was distilled off under reduced pressure to obtain the title compound (3.97 g) as a brown solid.

1H-NMRδ (DMSO-d6): 4.17 (3H, s), 8.10-8.14 (1H, m), 828 (1H, d, J=2.0 Hz), 13.73 (1H, brs). MS (m/z): 260 (M-H)-.

(h) Synthesis of 3-cyano-4-methoxy-5-trifluoromethoxybenzoyl chloride

To 3-cyano-4-methoxy-5-trifluoromethoxybenzoic acid (500 mg), toluene (10 mL), N,N-dimethylformamide (3 droplets) and thionyl chloride (0.28 mL) were added, and then the mixture was stirred at 60° C. for 6 hours. The solvent was distilled off under reduced pressure and the obtained residue was azeotroped with toluene and used for the synthesis of (i).

(i) Synthesis of 3-(3-cyano-4-methoxy-5-trifluoromethoxybenzoyl)-2,3-dihydro-1,3-benzothiazole 2,3-dihydro-1,3-benzothiazole synthesized from 2-aminobenzenethiol (359 mg) and 37% formalin (0.24 mL) in the same manner as in Example 1 was dissolved in chloroform (10 mL), and triethylamine (0.80 mL) and 3-cyano-4-methoxy-5-trifluoromethoxybenzoyl chloride were added to the solution, and then the mixture was stirred at room temperature for 17 hours. The solvent was distilled off under reduced pressure and water was added, and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was used for the synthesis of (j).

(j) Synthesis of 3-(3-cyano-4-methoxy-5-trifluoromethoxybenzoyl)-1,1-dioxo-2,3-dihydro-1,3-benzothiazole 3-(3-cyano-4-methoxy-5-trifluoromethoxybenzoyl)-2,3-dihydro-1,3-benzothiazole was dissolved in chloroform (15 mL), and 70% metachloroperbenzoic acid (1.98 g) was added to the solution, and then the mixture was stirred at room temperature for 6 hours and quenched with 10% sodium thio sulfate. The solvent was distilled off under reduced pressure and 1N sodium hydroxide was added, and then the mixture was extracted with ethyl acetate. The organic layer was washed with 1N sodium hydroxide and saturated brine, and then dried over anhydrous sodium sulfate. The solvent was distilled off under reduced pressure to obtain the title compound (631 mg) as a pale yellow solid.

(k) Synthesis of 3-(3-cyano-4-hydroxy-5-trifluoromethoxybenzoyl)-1,1-dioxo-2,3-dihydro-1,3-benzothiazole 3-(3-cyano-4-methoxy-5-trifluoromethoxybenzoyl)-1,1-dioxo-2,3-dihydro-1,3-benzothiazole (300 mg) was dissolved in N,N-dimethylformamide (4 mL), and lithium chloride (309 mg) was added to the solution, and then the mixture was stirred at 100° C. for 1 hour. To the reaction solution, 1N hydrochloric acid was added, and then the mixture was extracted with ethyl acetate. The organic layer was washed with 1N hydrochloric acid and saturated brine, and then dried over anhydrous sodium sulfate. The solvent was distilled off under reduced pressure and the obtained residue was crystallized from n-hexane-ethyl acetate to obtain the title compound (184 mg) as a colorless crystal.

1H-NMRδ (DMSO-d6): 5.37 (2H, s), 7.42 (1H, ddd, J=7.3, 7.3, 0.7 Hz), 7.77 (1H, ddd, J=8.4, 7.3, 1.3 Hz), 7.88-7.96 (2H, m), 8.04-8.11 (2H, m). MS (m/z): 397 (M-H)-.

Example 37

3-(3-chloro-4-hydroxy-5-trifluoromethoxybenzoyl)-1,1-dioxo-2,3-dihydro-1,3-benzothiazole

(a) Synthesis of acetic acid-2-trifluoromethoxyphenyl ester 2-trifluoromethoxyphenol (10.00 g) was dissolved in chloroform (30 mL), and triethylamine (6.11 mL) and acetic anhydride (6.37 mL) was added to the solution, and then the mixture was stirred at room temperature for 2 hours. To the reaction solution, 10% potassium carbonate was added, and then the mixture was extracted with chloroform. The organic layer was washed with an aqueous 5% citric acid solution and saturated brine, and then dried over anhydrous sodium sulfate. The solvent was distilled off under reduced pressure to obtain the title compound (11.39 g) as a colorless oily substance.

(b) Synthesis of 1-(4-hydroxy-3-trifluoromethoxyphenyl)ethanone

An acetic acid-2-trifluoromethoxyphenyl ester (11.39 g) was dissolved in trifluoromethanesulfonic acid (10 mL), and then the solution was stirred at room temperature for 2.5 hours. The reaction solution was poured into ice water and the reaction mixture was extracted with ethyl acetate. The organic layer was washed with water and saturated brine, and then dried over anhydrous sodium sulfate. The solvent was distilled off under reduced pressure and the obtained residue was purified by silica gel column chromatography (n-hexane:ethyl acetate=3:1) to obtain the title compound (4.55 g) as a colorless crystal.

(c) Synthesis of 1-(4-methoxymethoxy-3-trifluoromethoxyphenyl)ethanone 1-(4-hydroxy-3-trifluoromethoxyphenyl)ethanone (1.55 g) was dissolved in N,N-dimethylformamide (20 mL), and potassium carbonate (1.46 g) and chloromethyl methyl ether (0.64 mL) were added to the solution, and then the mixture was stirred at room temperature for 1 hour. Water was added to the reaction solution and the reaction mixture was extracted with ethyl acetate. The organic layer was washed with water and saturated brine, and then dried over anhydrous sodium sulfate. The solvent was distilled off under reduced pressure to obtain the title compound (1.54 g) as a colorless oily substance.

(d) Synthesis of methyl 4-methoxymethoxy-3-trifluoromethoxybenzoate 1-(4-methoxymethoxy-3-trifluoromethoxyphenyl)ethanone (540 mg) was dissolved in methanol (30 mL), and sodium methoxide (1.10 g) and N-bromosuccinimide (1.09 g) were added to the solution, and then the mixture was stirred at room temperature for 30 minutes. Water was added to the reaction solution and the reaction mixture was extracted with ethyl acetate. The organic layer was washed with saturated brine, and then dried over anhydrous sodium sulfate. The solvent was distilled off under reduced pressure to obtain the title compound (590 mg) as a yellow crystal.

(e) Synthesis of methyl 4-hydroxy-3-trifluoromethoxybenzoate

Methyl 4-methoxymethoxy-3-trifluoromethoxybenzoate (590 mg) was dissolved in chloroform (10 mL), and trifluoroacetic acid (5 mL) was added to the solution, and then the mixture was stirred at room temperature for 1 hour. Water was added to the solution, and then the mixture was extracted with chloroform. The organic layer was washed with saturated brine, and then dried over anhydrous sodium sulfate. The solvent was distilled off under reduced pressure and the obtained residue was washed with n-hexane to obtain the title compound (346 mg) as a colorless crystal.

(f) Synthesis of methyl 3-chloro-4-hydroxy-5-trifluoromethoxybenzoate

Methyl 4-hydroxy-3-trifluoromethoxybenzoate (2.05 g) was dissolved in chloroform (20 mL) and methanol (3 mL), and N-chlorosuccinimide (1.39 g) and trifluoromethanesulfonic acid (0.05 mL) were added to the solution, and then the mixture was stirred at 50° C. for 19 hours. The solvent was distilled off under reduced pressure and 1N hydrochloric acid was added, and then the mixture was extracted with ethyl acetate. The organic layer was washed with water and saturated brine, and then dried over anhydrous sodium sulfate. The solvent was distilled off under reduced pressure to obtain the title compound (2.64 g) as a yellow solid.

(g) Synthesis of methyl 3-chloro-4-methoxy-5-trifluoromethoxybenzoate

Methyl 3-chloro-4-hydroxy-5-trifluoromethoxybenzoate (2.64 g) was dissolved in N,N-dimethylformamide (15 mL), and potassium carbonate (3.60 g) and dimethylsulfuric acid (1.64 mL) were added to the solution, and then the mixture was stirred at room temperature for 1 hour. Water was added to the reaction solution and the reaction mixture was extracted with ethyl acetate. The organic layer was washed with water and saturated brine, and then dried over anhydrous sodium sulfate. The solvent was distilled off under reduced pressure and the obtained residue was purified by silica gel column chromatography (n-hexane:ethyl acetate=9:1) to obtain the title compound (1.70 g) as a colorless oily substance.

(h) Synthesis of 3-chloro-4-methoxy-5-trifluoromethoxybenzoic acid

Methyl 3-chloro-4-methoxy-5-trifluoromethoxybenzoate (1.70 g) was dissolved in tetrahydrofuran (12 mL) and water (6 mL), and lithium hydroxide monohydrate (1.00 g) was added to the solution, and the mixture was stirred at room temperature for 2 hours. The solvent was distilled off under reduced pressure and 1N hydrochloric acid was added, and then the mixture was extracted with ethyl acetate. The organic layer was washed with water and saturated brine, and then dried over anhydrous sodium sulfate. The solvent was distilled off under reduced pressure to obtain the title compound (1.51 g) as a colorless crystal.

1H-NMRδ (CDCl3): 4.04 (3H, s), 7.93 (1H, s), 8.10 (1H, d, J=1.9 Hz). MS (m/z): 269 (M-H)-.

(i) Synthesis of 3-chloro-4-methoxy-5-trifluoromethoxybenzoyl chloride

To 3-chloro-4-methoxy-5-trifluoromethoxybenzoic acid (401 mg), toluene (4 mL), N,N-dimethylformamide (1 droplet) and thionyl chloride (0.13 mL) were added, and then the mixture was stirred at 60° C. for 13 hours. The solvent was distilled off under reduced pressure and then azeotroped with toluene to obtain the title compound (436 mg) as a brown oily substance.

(j) Synthesis of 3-(3-chloro-4-methoxy-5-trifluoromethoxybenzoyl)-2,3-dihydro-1,3-benzothiazole 2,3-dihydro-1,3-benzothiazole synthesized from 2-aminobenzenethiol (278 mg) and 37% formalin (0.18 mL) in the same manner as in Example 1 was dissolved in dichloromethane (6.5 mL), and diisopropylethylamine (0.50 mL) and 3-chloro-4-methoxy-5-trifluoromethoxybenzoyl chloride (436 mg) were added to the solution, and then the mixture was stirred at room temperature for 1 hour. The solvent was distilled off under reduced pressure and water was added, and then the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was used for the synthesis of (k).

(k) Synthesis of 3-(3-chloro-4-methoxy-5-trifluoromethoxybenzoyl)-1,1-dioxo-2,3-dihydro-1,3-benzothiazole 3-(3-chloro-4-methoxy-5-trifluoromethoxybenzoyl)-2,3-dihydro-1,3-benzothiazole was dissolved in chloroform (10 mL), and 70% metachloroperbenzoic acid (2.57 g) was added to the solution, and then the mixture was stirred at room temperature for 22 hours. 1N sodium hydroxide was added, and then the mixture was extracted with ethyl acetate. The organic layer was washed with 1N sodium hydroxide and saturated brine, and then dried over anhydrous sodium sulfate. The solvent was distilled off under reduced pressure and the obtained residue was purified by silica gel column chromatography (n-hexane:ethyl acetate=4:1) to obtain the title compound (420 mg) as a colorless oily substance.

(l) Synthesis of 3-(3-chloro-4-hydroxy-5-trifluoromethoxybenzoyl)-1,1-dioxo-2,3-dihydro-1,3-benzothiazole 3-(3-chloro-4-methoxy-5-trifluoromethoxybenzoyl)-1,1-dioxo-2,3-dihydro-1,3-benzothiazole (420 mg) was dissolved in N,N-dimethylformamide (5 mL), and lithium chloride (421 mg) was added to the solution, and then the mixture was stirred at 120° C. for 14 hours. To the reaction solution, 1N hydrochloric acid was added, and then the mixture was extracted with ethyl acetate. The organic layer was washed with 1N hydrochloric acid and saturated brine, and then dried over anhydrous sodium sulfate. The solvent was distilled off under reduced pressure and the obtained residue was crystallized from n-hexane-ethyl acetate to obtain the title compound (182 mg) as a colorless crystal.

1H-NMRδ (DMSO-d6): 5.36 (2H, s), 7.44 (1H, dd, J=7.6, 7.0 Hz), 7.67 (1H, brs), 7.76 (1H, dd, J=8.1, 7.6 Hz), 7.82 (1H, d, J=2.2 Hz), 7.91 (1H, d, J=7.0 Hz), 8.03 (1H, d, J=8.1 Hz), 11.52 (1H, brs). MS (m/z): 406 (M-H)-.

Example 38

3-(3-cyano-4-hydroxy-5-trifluoromethylbenzoyl)-1,1-dioxo-5-trifluoromethyl-2,3-dihydro-1,3-benzothiazole (a) Synthesis of 5-trifluoromethyl-2,3-dihydro-1,3-benzothiazole 37% formalin (0.22 mL) was diluted with water (6 mL), and diethylether (6 mL), triethylamine (0.37 mL) and 2-amino-4-trifluoromethylbenzenethiol hydrochloride (611 mg) were added to the solution, and then the mixture was stirred at room temperature for 30 minutes. The organic layer was separated and the aqueous layer was extracted with diethylether. The organic layers were combined, washed with saturated brine, and then dried over anhydrous sodium sulfate. The solvent was distilled off under reduced pressure and the obtained residue was used for the synthesis of (b).

(b) Synthesis of 3-(3-cyano-4-methoxy-5-trifluoromethylbenzoyl)-5-trifluoromethyl-2,3-dihydro-1,3-benzothiazole 5-trifluoromethyl-2,3-dihydro-1,3-benzothiazole was dissolved in dichloromethane (5 mL), and triethylamine (0.56 mL) and 3-cyano-4-methoxy-5-trifluoromethylbenzoyl chloride (839 mg) were added to the solution, and then the mixture was stirred at room temperature for 1.5 hours. Water was added and the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was purified by silica gel column chromatography (n-hexane:ethyl acetate=8:1) to obtain the title compound (479 mg) as a pale yellow amorphous product.

(c) Synthesis of 3-(3-cyano-4-methoxy-5-trifluoromethylbenzoyl)-1,1-dioxo-5-trifluoromethyl-2,3-dihydro-1,3-benzothiazole 3-(3-cyano-4-methoxy-5-trifluoromethylbenzoyl)-5-trifluoromethyl-2,3-dihydro-1,3-benzothiazole (520 mg) was dissolved in chloroform (8 mL), and 70% metachloroperbenzoic acid (2.37 g) was added to the solution at 0° C. After stirring the mixture at room temperature for 40 hours, 1N sodium hydroxide was added, and then the precipitated crystal was collected by filtration and washed with 1N sodium hydroxide and water. Furthermore, the filtrate was extracted with ethyl acetate, and the organic layer was washed with 1N sodium hydroxide and saturated brine, and then dried over anhydrous sodium sulfate. The solvent was distilled off under reduced pressure and the obtained product was combined with the crystal collected by filtration, and then the mixture was washed with a mixture of n-hexane and ethyl acetate in a mixing ratio of 1:1 to obtain the title compound (459 mg) as a colorless crystal.

(d) Synthesis of 3-(3-cyano-4-hydroxy-5-trifluoromethylbenzoyl)-1,1-dioxo-5-trifluoromethyl-2,3-dihydro-1,3-benzothiazole 3-(3-cyano-4-methoxy-5-trifluoromethylbenzoyl)-1,1-dioxo-5-trifluoromethyl-2,3-dihydro-1,3-benzothiazole (459 mg) was dissolved in N,N-dimethylformamide (4.5 mL), and lithium chloride (169 mg) was added to the solution, and then the mixture was stirred at 70° C. for 1 hour. To the reaction solution, 1N hydrochloric acid was added, and then the mixture was extracted with ethyl acetate. The organic layer was washed with 1N hydrochloric acid and saturated brine, and then dried over anhydrous sodium sulfate. The solvent was distilled off under reduced pressure and the obtained residue was crystallized from n-hexane-chloroform to obtain the title compound (411 mg) as a colorless crystal.

1H-NMRδ (DMSO-d6): 5.47 (2H, s), 7.81 (1H, d, J=8.1 Hz), 8.10 (1H, s), 8.21 (1H, d, J=8.1 Hz), 8.28 (1H, s), 8.43 (1H, s). MS (m/z): 449 (M-H)-.

Example 39

3-(3,5-dichloro-4-hydroxybenzoyl)-1,1-dioxo-5-trifluoromethyl-2,3-dihydro-1,3-benzothiazole (a) Synthesis of 3-(3,5-dichloro-4-methoxybenzoyl)-5-trifluoromethyl-2,3-dihydro-1,3-benzothiazole 2-amino-4-trifluoromethylbenzenethiol hydrochloride (502 mg), and 5-trifluoromethyl-2,3-dihydro-1,3-benzothiazole synthesized from 37% formalin (0.18 mL) and triethylamine (0.30 mL) in the same manner as in Example 38 were dissolved in dichloromethane (5 mL), and triethylamine (0.30 mL) and 3,5-dichloro-4-methoxybenzoyl chloride (354 mg) were added to the solution, and then the mixture was stirred at room temperature for 2 hours. Water was added and the mixture was extracted with ethyl acetate. The organic layer was washed with 1N hydrochloric acid, 1N sodium hydroxide and saturated brine, and then dried over anhydrous sodium sulfate. The solvent was distilled off under reduced pressure and the obtained residue was purified by silica gel column chromatography (n-hexane:ethyl acetate=8:1) to obtain the title compound (223 mg) as a colorless oily substance.

(b) Synthesis of 3-(3,5-dichloro-4-methoxybenzoyl)-1,1-dioxo-5-trifluoromethyl-2,3-dihydro-1,3-benzothiazole 3-(3,5-dichloro-4-methoxybenzoyl)-5-trifluoromethyl-2,3-dihydro-1,3-benzothiazole (223 mg) was dissolved in chloroform (5 mL), and 70% metachloroperbenzoic acid (805 mg) was added to the solution at 0° C. After stirring the mixture at room temperature for 20 hours, 1N sodium hydroxide was added, and then the mixture was extracted with ethyl acetate. The organic layer was washed with 1N sodium hydroxide and saturated brine, and then dried over anhydrous sodium sulfate. The solvent was distilled off under reduced pressure to obtain the title compound (211 mg) as a pale yellow crystal.

(c) Synthesis of 3-(3,5-dichloro-4-hydroxybenzoyl)-1,1-dioxo-5-trifluoromethyl-2,3-dihydro-1,3-benzothiazole 3-(3,5-dichloro-4-methoxybenzoyl)-1,1-dioxo-5-trifluoromethyl-2,3-dihydro-1,3-benzothiazole (209 mg) was dissolved in N,N-dimethylformamide (2 mL), lithium chloride (106 mg) was added to the solution, and then the mixture was stirred at 120° C. for 2 hours. To the reaction solution, 1N hydrochloric acid was added, and then the mixture was extracted with ethyl acetate. The organic layer was washed with 1N hydrochloric acid and saturated brine, and then dried over anhydrous sodium sulfate. The solvent was distilled off under reduced pressure and the obtained residue was crystallized from n-hexane-chloroform to obtain the title compound (167 mg) as a pale yellow crystal.

1H-NMRδ (DMSO-d6): 5.46 (2H, s), 7.76 (2H, s), 7.80 (1H, d, J=8.1 Hz), 8.20 (1H, d, J=8.1 Hz), 8.41 (1H, s), 11.11 (1H, brs). MS (m/z): 424 (M-H)-, 426 (M+2-H)-.

Example 40

3-(3-chloro-4-hydroxy-5-trifluoromethylbenzoyl)-5 or 6-hydroxy-1,1-dioxo-2,3-dihydro-1,3-benzothiazole 3-(3-chloro-4-hydroxy-5-trifluoromethylbenzoyl)-1,1-dioxo-2,3-dihydro-1,3-benzothiazole (941 mg) obtained in Example 18 was suspended in 15.7 mL of a 0.5% methyl cellulose solution (0.5% MC) and the suspension was administered to eight male Wistar/ST rats in each amount of 1.8 mL and urine was collected for 6.5 hours immediately after administration. The obtained urine (28 mL) was acidified with hydrochloric acid and then extracted with ethyl acetate. The obtained organic layer was washed with brine, and d then dried over anhydrous sodium sulfate. The solvent was distilled off under reduced pressure and the obtained residue was purified by silica gel column chromatography (n-hexane:ethyl acetate=1:1) and then crystallized from n-hexane:ethyl acetate to obtain the title compound (36 mg).

1H-NMRδ (DMSO-d6): 5.34 (2H, s), 7.09 (1H, d, Hz), 7.15 (1H dd, J=9.0, 2.6 Hz), 7.82 (1H, d, J=1.9 Hz), 7.90 (1H, d, J=9.0 Hz), 8.02 (1H, d, J=1.9 Hz), 10.34 (1H, s), 11.38 (1H, brs). MS (m/z): 406 (M-H)-, 408 (M+2-H)-.

In the following Table 1, R1, R2, R3 and X in the above respective Examples are listed with respect to the compound represented by the general formula (1).

TABLE 1

| Examples | R$^1$ | R$^2$ | R$^3$ | X |
|---|---|---|---|---|
| Example 1 | Cl | Cl | — | SO$_2$ |
| Example 2 | Cl | Cl | — | S |
| Example 3 | Cl | Cl | — | SO |
| Example 4 | CF$_3$ | CN | — | SO$_2$ |
| Example 5 | CF$_3$ | CN | — | S |
| Example 6 | CF$_3$ | CN | — | SO |
| Example 7 | Cl | CN | — | SO$_2$ |
| Example 8 | Cl | CN | — | S |
| Example 9 | tBu | CN | — | SO$_2$ |
| Example 10 | iPr | CN | — | SO$_2$ |
| Example 11 | cBu | CN | — | SO$_2$ |
| Example 12 | Et | CN | — | SO$_2$ |
| Example 13 | cPr | CN | — | SO$_2$ |
| Example 14 | C≡CH | CN | — | SO$_2$ |
| Example 15 | S—Me | CN | — | SO$_2$ |
| Example 16 | SO$_2$Me | CN | — | SO$_2$ |
| Example 17 | SOMe | CN | — | SO$_2$ |
| Example 18 | CF$_3$ | Cl | — | SO$_2$ |
| Example 19 | F | Cl | — | SO$_2$ |
| Example 20 | F | F | — | SO$_2$ |
| Example 21 | S—Me | Cl | — | SO$_2$ |
| Example 22 | SO$_2$Me | Cl | — | SO$_2$ |
| Example 23 | SOMe | Cl | — | SO$_2$ |
| Example 24 | SO$_2$Me | CF$_3$ | — | SO$_2$ |
| Example 25 | SO$_2$Me | tBu | — | SO$_2$ |
| Example 26 | CF$_3$ | OMe | — | SO$_2$ |
| Example 27 | CF$_3$ | CONMe$_2$ | — | SO$_2$ |
| Example 28 | CF$_3$ | — | — | SO$_2$ |
| Example 29 | OMe | Cl | — | SO$_2$ |

TABLE 1-continued

| Examples | R$^1$ | R$^2$ | R$^3$ | X |
|---|---|---|---|---|
| Example 30 | CF$_3$ | (C(=O)-pyrrolidinyl) | — | SO$_2$ |
| Example 31 | CF$_3$ | (C(=O)-thiazolidinyl) | — | SO$_2$ |
| Example 32 | CF$_3$ | (C(=O)-thiazolidinyl S-oxide) | — | SO$_2$ |
| Example 33 | CF$_3$ | (C(=O)-thiazolidinyl S,S-dioxide) | — | SO$_2$ |
| Example 34 | S—Et | CN | — | SO$_2$ |
| Example 35 | S—iPr | CN | — | SO$_2$ |
| Example 36 | OCF$_3$ | CN | — | SO$_2$ |
| Example 37 | OCF$_3$ | Cl | — | SO$_2$ |
| Example 38 | CF$_3$ | CN | 5-CF$_3$ | SO$_2$ |
| Example 39 | Cl | Cl | 5-CF$_3$ | SO$_2$ |
| Example 40 | CF$_3$ | Cl | 5 or 6-OH | SO$_2$ |

Test Example 1

Uricosuric Action in Rat Pyrazinamide Model

Pyrazinamide suspended in a 0.5% methyl cellulose solution (0.5% MC) was orally administered to 7- and 8-week-old male Wistar/ST rats (4 rats per group) fasted for about 16 hours in a dose of 400 mg/kg. After 30 minutes, a test substance suspended in 0.5% MC was orally administered in a dose of 30 mg/kg, and urine was collected for 1 hour in a range from 2 to 3 hours after administration. At the beginning of collection of urine and after completion of collection of urine, rats were forced to urinate by pressing the abdomen of the rat. The concentration of uric acid and that of creatinine in urine were measured by a kit, and a ratio of the concentration of uric acid to that of creatinine was used as an indicator of a uricosuric action. The action of each test substance was expressed by percentage to control.

Test Example 2

Concentration of Unchanged Compound in Urine in Rat

A test substance suspended in 0.5% MC was orally administered to two male Wistar/ST rats fasted for about 16 hours in a dose of 3 mg/kg. Immediately after administration, urine was collected for 4 hours. After completion of collection of urine, urine remaining in the bladder was completely excreted by pressing the abdomen of the rat. The concentration of an unchanged compound in urine was measured by HPLC and expressed by a molar concentration (μM).

The above test results are shown in Table 2 below.

TABLE 2

| Examples | Uricosuric action (control = 100) | Concentration of unchanged compound in urine (μM) |
|---|---|---|
| Example 1 | 169 | 9.8 |
| Example 4 | 201 | 51.8 |
| Example 5 | 136 | 1.1 |
| Example 7 | 178 | 125 |
| Example 12 | 187 | 15.8 |
| Example 13 | 172 | 3.9 |
| Example 14 | 164 | 119 |
| Example 15 | 204 | 68.6 |
| Example 18 | 202 | 1 |
| Example 19 | 129 | 55.2 |
| Example 21 | 120 | 1.9 |
| Example 27 | 146 | 30.6 |
| Example 34 | 208 | 23.5 |
| Example 35 | 140 | 1.5 |
| Example 38 | 180 | 16.4 |
| Benzbromarone | 114 | 0 |
| Probenecid | 111 | 0 |
|  | 171 (100 mg/kg) |  |

As described above, a novel phenol derivative represented by the general formula (1), a pharmaceutically acceptable salt thereof, and a hydrate thereof and a solvate thereof exhibit a uricosuric action of 20% to 108%, and also have excellent drug effectiveness as compared with an existing drug which exhibits a uricosuric action of 11% to 14%. A novel phenol derivative represented by the general formula (1), a pharmaceutically acceptable salt thereof, and a hydrate thereof and a solvate thereof are excellent in that an unchanged compound exert drug effectiveness, as compared with an existing drug in which excretion of an unchanged compound in urine is not recognized, since an unchanged compound is clearly excreted in urine. Accordingly, a novel phenol derivative represented by the general formula (1), a pharmaceutically acceptable salt thereof, and a hydrate thereof and a solvate thereof exhibit high concentration of an unchanged compound in urine, and also have excellent uricosuric action and are excellent in safety, and are therefore useful as a pharmaceutical for the acceleration of excretion of uric acid; a pharmaceutical for the reduction of the amount of uric acid and/or concentration of uric acid in blood and/or in tissue; a pharmaceutical for use in the prevention and/or treatment of a disease associated with uric acid in blood and/or in tissue; a pharmaceutical for use in the prevention and/or treatment of hyperuricaemia; and a pharmaceutical for use in the prevention and/or treatment of a disease associated with hyperuricaemia and/or a disease accompanied by hyperuricaemia.

Formulation Example

Tablets

| Compound of Example 1 | 5 mg |
|---|---|
| Lactose | 70 mg |
| Corn starch | 21 mg |
| Hydroxypropyl cellulose | 3 mg |
| Magnesium stearate | 1 mg |
| Total | 100 mg |

After weighing the above components in a ratio according to the formulation, a powder for compression is produced by a wet granulation method. To obtain tablets, this powder was compressed so as to contain 5 mg of the compound of Example 1 in one tablet.

The compounds of the present invention exhibit high concentration of an unchanged compound in urine, and also have excellent uricosuric action and are excellent in safety, and are therefore useful as a pharmaceutical for the acceleration of excretion of uric acid; a pharmaceutical for the reduction of the amount of uric acid and/or concentration of uric acid in blood and/or in tissue; a pharmaceutical for use in the prevention and/or treatment of a disease associated with uric acid in blood and/or in tissue; a pharmaceutical for use in the prevention and/or treatment of hyperuricaemia; and a pharmaceutical for use in the prevention and/or treatment of a disease associated with hyperuricaemia and/or a disease accompanied by hyperuricaemia.

The invention claimed is:

1. A phenol derivative represented by the following formula (1)

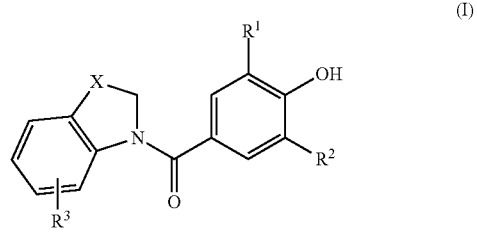

wherein $R^1$ and $R^2$ are the same or different and represent a lower alkyl group, a lower alkenyl group, a lower alkynyl group, a lower alkoxy group, a haloalkyl group, a haloalkoxy group, an alkylsulfanyl group, an alkylsulfinyl group, an alkylsulfonyl group, a lower alkyl-substituted carbamoyl group, a saturated nitrogen-containing heterocyclic N-carbonyl group, a halogen atom, a cyano group or a hydrogen atom, $R^3$ represents a lower alkyl group, a haloalkyl group, a halogen atom, a hydroxyl group or a hydrogen atom, and X represents a sulfur atom, —S(=O)— or —S(=O)$_2$—, a pharmaceutically acceptable salt thereof, a hydrate thereof or a solvate thereof.

2. The compound according to claim 1, wherein $R^1$ represents a lower alkyl group, a lower alkenyl group, a lower alkynyl group, a lower alkoxy group, a haloalkyl group, a haloalkoxy group, an alkylsulfanyl group, a lower alkyl-substituted carbamoyl group, a saturated nitrogen-containing heterocyclic N-carbonyl group or a halogen atom, $R^2$ represents a cyano group, a haloalkyl group or a halogen atom, $R^3$ represents a haloalkyl group, a hydroxyl group or a hydrogen atom, and X represents a sulfur atom or —S(=O)$_2$—, a pharmaceutically acceptable salt thereof, a hydrate thereof or a solvate thereof.

3. The compound according to claim 1, wherein $R^1$ represents a haloalkyl group or a halogen atom, $R^2$ represents a cyano group or a halogen atom, $R^3$ represents a hydrogen atom, and X represents —S(=O)$_2$—, a pharmaceutically acceptable salt thereof, and a hydrate thereof and a solvate thereof.

4. A pharmaceutical composition comprising, as an active ingredient, one or more substances selected from the group consisting of the compound according to claim 1, a pharmaceutically acceptable salt thereof, a hydrate thereof, and a solvate thereof.

5. The pharmaceutical composition on according to claim 4 which is in the form of a pharmaceutical composition containing one, or two, or more additives for formulation.

6. A method of acceleration of excretion of uric acid, comprising the step of administering the pharmaceutical composition of claim 5 to a patient.

7. A method of acceleration of excretion of uric acid, comprising the step of administering the pharmaceutical composition of claim 4 to a patient.

8. A method of reducing uric acid in blood or tissue comprising the step of administering the pharmaceutical composition of claim 4 to a patient.

9. A method of reducing uric acid in blood or tissue comprising the step of administering the pharmaceutical composition of claim 5 to a patient.

10. A method for or treating hyperuricaemia comprising the step of administering the pharmaceutical composition of claim 4 to a patient.

11. A method for or treating hyperuricaemia comprising the step of administering the pharmaceutical composition of claim 5 to a patient.

12. A pharmaceutical composition comprising, as an active ingredient, one or more substances selected from the group consisting of the compound according to claim 2, a pharmaceutically acceptable salt thereof, a hydrate thereof, and a solvate thereof.

13. A pharmaceutical composition comprising, as an active ingredient, one or more substances selected from the group consisting of the compound according to claim 3, a pharmaceutically acceptable salt thereof, a hydrate thereof, and a solvate thereof.

* * * * *

UNITED STATES PATENT AND TRADEMARK OFFICE
CERTIFICATE OF CORRECTION

PATENT NO. : 8,367,843 B2
APPLICATION NO. : 13/499190
DATED : February 5, 2013
INVENTOR(S) : Kobashi et al.

It is certified that error appears in the above-identified patent and that said Letters Patent is hereby corrected as shown below:

In the Specifications:

Column 2
Line 10, "factor" should be -- factors --.
Line 26, "Hide" should be -- rule --.
Line 66, "transporters" should be -- transporter --.

Column 3
Line 22, "[So," should be -- So, --.

Column 4
Line 2, "(2003)" should be -- (2004) --.
Line 25, "are" should be -- is --.
Line 51, "—S(O)$_2$—" should be -- —S(=O)2- --.

Column 5
Line 45, "—S(O)$_2$—" should be -- —S(=O)2- --.
Line 48, "—S(O)$_2$—" should be -- —S(=O)2- --.

Column 7
Fifth Step, "R$^2$" should be -- R$_2$ --.

Column 10
Line 11, "R$^6$=I, Br, C1" should be -- R$^6$=I, Br, Cl --.

Column 11
Line 45, "organoithium" should be -- organolithium --.
Line 46, "formylated" should be -- formulated --.

Signed and Sealed this
Seventh Day of May, 2013

Teresa Stanek Rea
*Acting Director of the United States Patent and Trademark Office*

CERTIFICATE OF CORRECTION (continued)
U.S. Pat. No. 8,367,843 B2

Column 15
Line 22, "dose" should be -- doses --.
Line 64, "mom" should be -- room --.

Column 20
Line 45, "(222 g)" should be -- (2.22 g) --.

Column 23
Line 33, "stiffed" should be -- stirred --.

Column 24
Line 50, "(20 ml)" should be -- (20 mL) --.

Column 27
Lines 52-53, "thio sulfate" should be -- thiosulfate --.

Column 29
Line 46, "mom" should be -- room --.

Column 33
Line 31, "mom" should be -- room --.
Line 52, "resiue" should be -- residue --.

Column 35
Line 20, "mom" should be -- room --.

Column 41
Line 23, "dthydro" should be -- dihydro --.

Column 42
Lines 29-30, "thio sulfate" should be -- thiosulfate --.
Line 53, "3.59" should be -- 7.59 --.

Column 44
Line 5, "was'washed" should be -- was washed --.

Column 47
Line 34, "(126)" should be -- (1.26) --.

Column 49
Line 11, "825" should be -- 8.25 --.

Column 50
Line 9, "(CDCl$_3$)" should be -- (CDC13) --.
Line 10, "J=22" should be -- J=2.2 --.

Column 52
Line 67, "mom" should be -- room --.

Column 56
Line 58, "mom" should be -- room --.

Column 61
Line 3, "mom" should be -- room --.

Column 63
Line 40, after "dd," insert -- J=6.6, --.

Column 65
Line 1, "3.6" should be -- 7.6 --.

Column 67
Line 10, "828" should be -- 8.28 --.
Lines 49-50, "thio sulfate" should be -- thiosulfate --.

Column 73
Line 24, "and d then" should be -- and then --.
Lines 29-30, "n-hexane:ethyl acetate" should be -- n-hexane-ethyl acetate --.
Lines 31-32, "d, Hz), 7.15 (1H dd," should be -- d, J=2.6 Hz), 7.15 (1H, dd, --.
Line 35, "R1, R2, R3" should be -- $R^1, R^2, R^3$ --.

Column 75
Line 34, "exert" should be -- exerts --.

In the Claims:

Column 77
Claim 5, Line 1, "composition on according" should be -- composition according --.

Column 78
Claim 10, Line 1, "for or treating" should be -- for treating --.
Claim 11, Line 4, "for or treating" should be -- for treating --.